(12) United States Patent
Haines

(10) Patent No.: US 7,662,183 B2
(45) Date of Patent: Feb. 16, 2010

(54) DYNAMIC SPINAL IMPLANTS INCORPORATING CARTILAGE BEARING GRAFT MATERIAL

(76) Inventor: Timothy Haines, 401 Jay St., Lacrosse, WI (US) 54601

( * ) Notice: Subject to any disclaimer, the term of this patent is extended or adjusted under 35 U.S.C. 154(b) by 145 days.

(21) Appl. No.: 11/626,634

(22) Filed: Jan. 24, 2007

(65) Prior Publication Data

US 2007/0225813 A1   Sep. 27, 2007

Related U.S. Application Data

(60) Provisional application No. 60/761,540, filed on Jan. 24, 2006.

(51) Int. Cl.
*A61F 2/44* (2006.01)
(52) U.S. Cl. .................................. 623/17.11
(58) Field of Classification Search .................. 606/61; 623/17.11–17.16
See application file for complete search history.

(56) References Cited

U.S. PATENT DOCUMENTS

| | | | |
|---|---|---|---|
| 4,772,287 A | 9/1988 | Ray et al. | |
| 4,911,718 A | 3/1990 | Lee et al. | |
| 4,959,064 A | 9/1990 | Engelhardt | |
| 5,458,643 A * | 10/1995 | Oka et al. ................. | 623/17.16 |
| 5,514,139 A | 5/1996 | Goldstein et al. | |
| 5,545,229 A | 8/1996 | Parsons et al. | |
| 5,549,679 A | 8/1996 | Kuslich | |
| 5,597,379 A | 1/1997 | Haines et al. | |
| 5,643,272 A | 7/1997 | Haines et al. | |
| 5,799,055 A | 8/1998 | Peshkin et al. | |
| 5,810,827 A | 9/1998 | Haines et al. | |
| 5,919,235 A | 7/1999 | Husson et al. | |
| 6,099,529 A | 8/2000 | Gertzman et al. | |
| 6,162,225 A | 12/2000 | Gertzman et al. | |
| 6,236,875 B1 | 5/2001 | Bucholz et al. | |
| 6,264,695 B1 * | 7/2001 | Stoy ......................... | 623/17.16 |
| 6,277,149 B1 * | 8/2001 | Boyle et al. .............. | 623/17.16 |
| 6,285,902 B1 | 9/2001 | Kienzle, III et al. | |
| 6,290,724 B1 * | 9/2001 | Marino ..................... | 623/17.11 |
| 6,340,363 B1 | 1/2002 | Bolger et al. | |
| 6,348,058 B1 | 2/2002 | Melkent et al. | |
| 6,430,434 B1 | 8/2002 | Mittelstadt | |
| 6,443,988 B2 * | 9/2002 | Felt et al. ................. | 623/17.12 |

(Continued)

FOREIGN PATENT DOCUMENTS

JP        02274214 A      8/1990

(Continued)

OTHER PUBLICATIONS

P.M. Buechner, Size Effects in the Elasticity and Viscoelasticity of Bone, Biomechan Model Mechanobiol 2003, pp. 295-301.

*Primary Examiner*—Pedro Philogene
(74) *Attorney, Agent, or Firm*—Patterson, Thuente, Skaar & Christensen, P.A.

(57) ABSTRACT

A dynamic spinal implant utilizes cartilage bearing graft material in dynamic disc replacement and/or facet arthroplasty. Methods and apparatus for dynamic spinal implants incorporate bulk articular graft tissues derived from donor joint sources in human (allograft or autograft) or non-human (xenograft) tissue. The donor joint is preferably prepared as a biological dynamic spinal implant with articular cartilage as a bearing interface between adjacent bone surfaces that naturally articulate with respect to one another.

5 Claims, 45 Drawing Sheets

U.S. PATENT DOCUMENTS

| | | | |
|---|---|---|---|
| 6,470,207 | B1 | 10/2002 | Simon et al. |
| 6,477,400 | B1 | 11/2002 | Barrick |
| 6,491,699 | B1 | 12/2002 | Henderson et al. |
| 6,506,192 | B1 | 1/2003 | Gertzman et al. |
| 6,533,818 | B1 | 3/2003 | Weber et al. |
| 6,595,997 | B2 | 7/2003 | Axelson, Jr. et al. |
| 6,685,711 | B2 | 2/2004 | Axelson, Jr. et al. |
| 6,694,168 | B2 | 2/2004 | Traxel et al. |
| 6,695,848 | B2 | 2/2004 | Haines |
| 6,697,664 | B2 | 2/2004 | Kienzle, III et al. |
| 6,701,174 | B1 | 3/2004 | Krause et al. |
| 6,711,432 | B1 | 3/2004 | Krause et al. |
| 6,725,080 | B2 | 4/2004 | Melkent et al. |
| 6,726,721 | B2 | 4/2004 | Stoy et al. |
| 6,827,723 | B2 | 12/2004 | Carson |
| 7,052,514 | B2 * | 5/2006 | Kellner et al. ............ 623/11.11 |
| 2002/0029038 | A1 | 3/2002 | Haines |
| 2003/0028196 | A1 | 2/2003 | Bonutti |
| 2003/0069585 | A1 | 4/2003 | Axelson, Jr. et al. |
| 2003/0069591 | A1 | 4/2003 | Carson et al. |
| 2003/0069639 | A1 | 4/2003 | Sander et al. |
| 2003/0208122 | A1 | 11/2003 | Melkent et al. |
| 2004/0010317 | A1 * | 1/2004 | Lambrecht et al. ........ 623/17.16 |
| 2004/0039396 | A1 | 2/2004 | Couture et al. |
| 2004/0122305 | A1 | 6/2004 | Grimm et al. |
| 2004/0122436 | A1 | 6/2004 | Grimm |
| 2004/0152970 | A1 | 8/2004 | Hunter et al. |
| 2004/0153083 | A1 | 8/2004 | Nemec et al. |
| 2004/0153085 | A1 | 8/2004 | Farling et al. |
| 2004/0253219 | A1 * | 12/2004 | Hedman .................... 424/94.4 |
| 2006/0015109 | A1 | 1/2006 | Haines |
| 2006/0015115 | A1 | 1/2006 | Haines |
| 2006/0015116 | A1 | 1/2006 | Haines |
| 2006/0015117 | A1 | 1/2006 | Haines |
| 2006/0173542 | A1 * | 8/2006 | Shikinami ................ 623/14.12 |

FOREIGN PATENT DOCUMENTS

| | | |
|---|---|---|
| WO | WO 2004/069036 A2 | 8/2004 |
| WO | WO 2004/069036 A3 | 8/2004 |
| WO | WO 2004/070580 A2 | 8/2004 |
| WO | WO 2004/070580 A3 | 8/2004 |
| WO | WO 2004/100758 A2 | 11/2004 |
| WO | WO 2004/100758 A3 | 11/2004 |

* cited by examiner

FIG. 16
Prior Art - Fusion
Sofamor Danek Threaded Bone Dowels
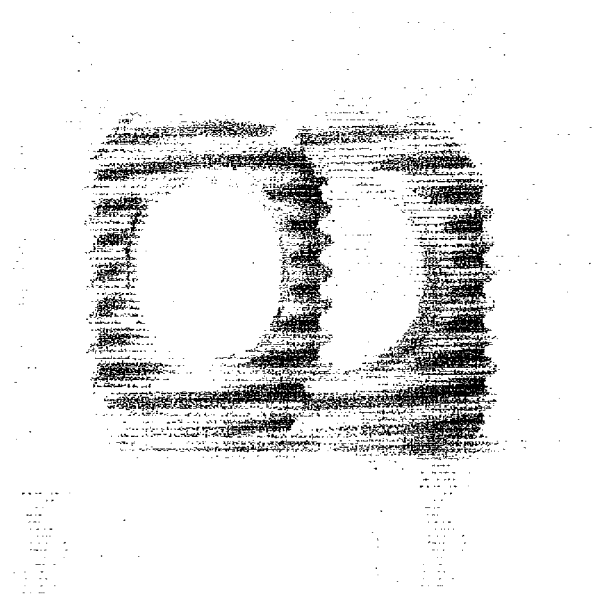
MSD Interfix™ Cage
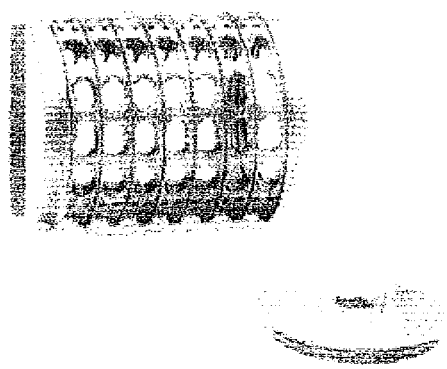
MSD Interfix™ Cage & Pedicle Screws
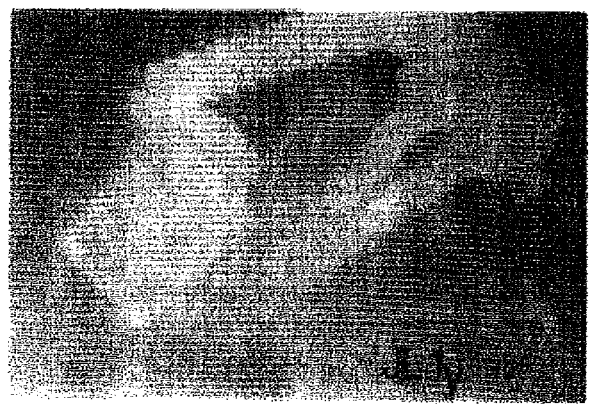

FIG. 26
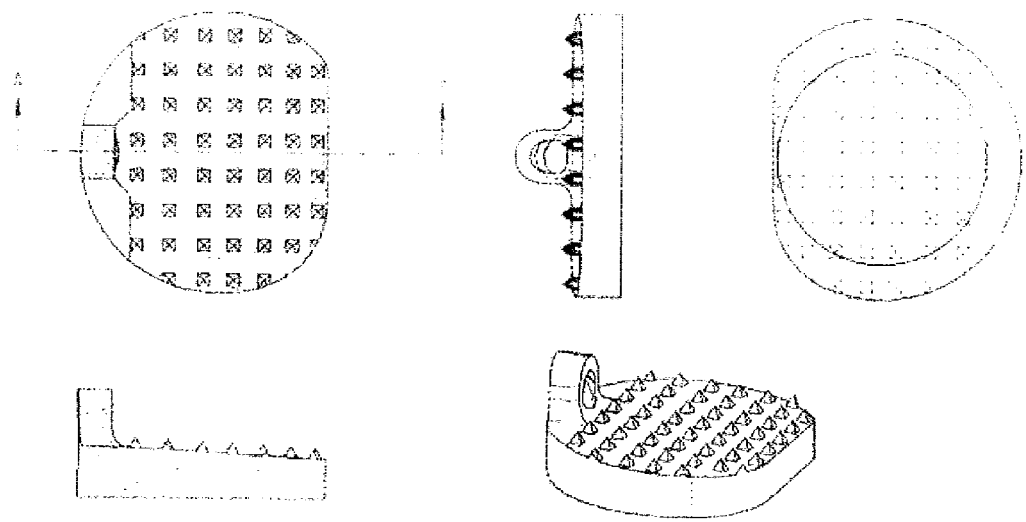
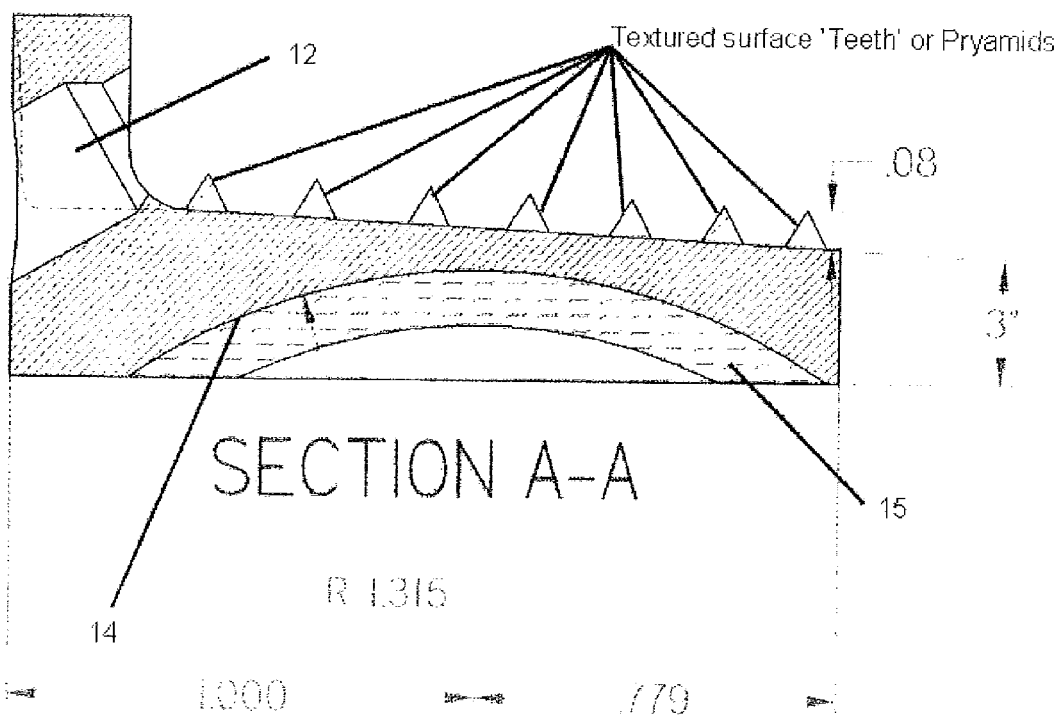
SECTION A-A

FIG. 28
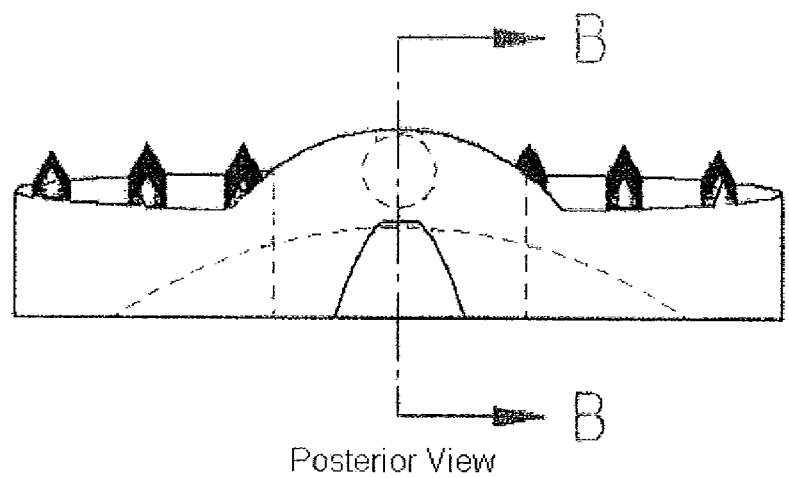
Posterior View
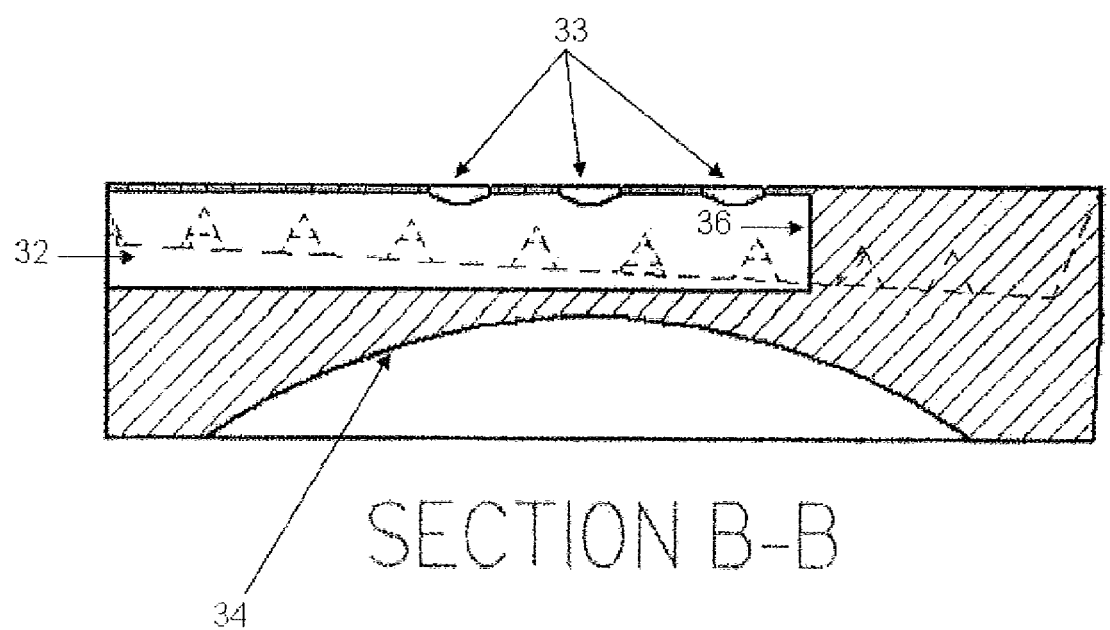
SECTION B-B

FIG. 32
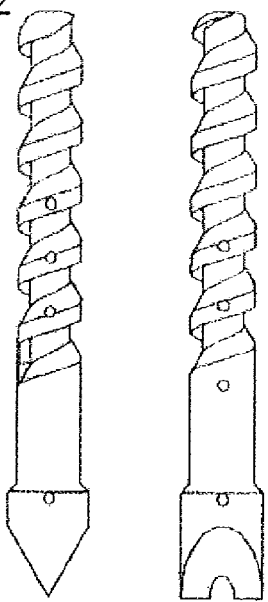
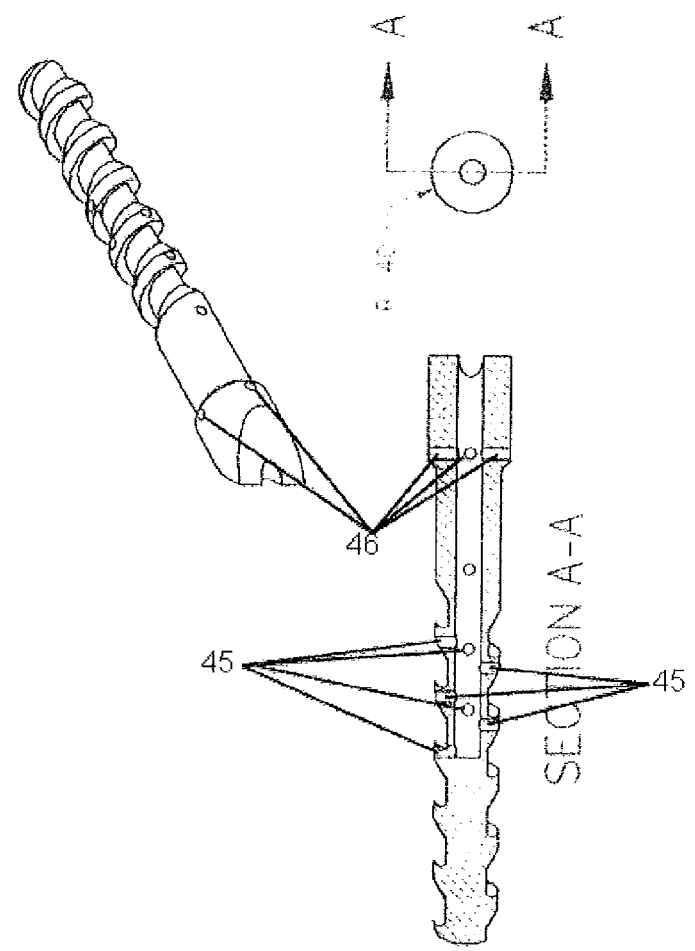

FIG. 33
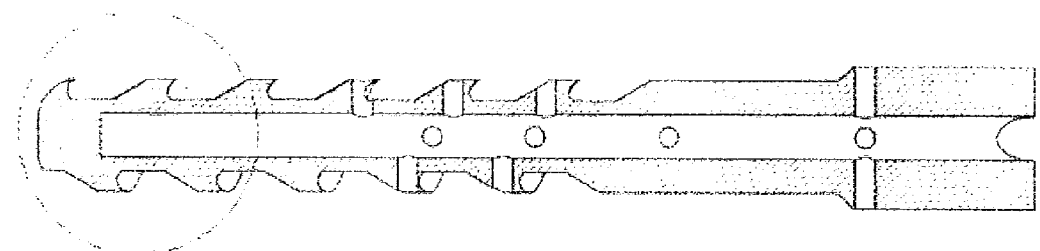
B  SECTION A-A
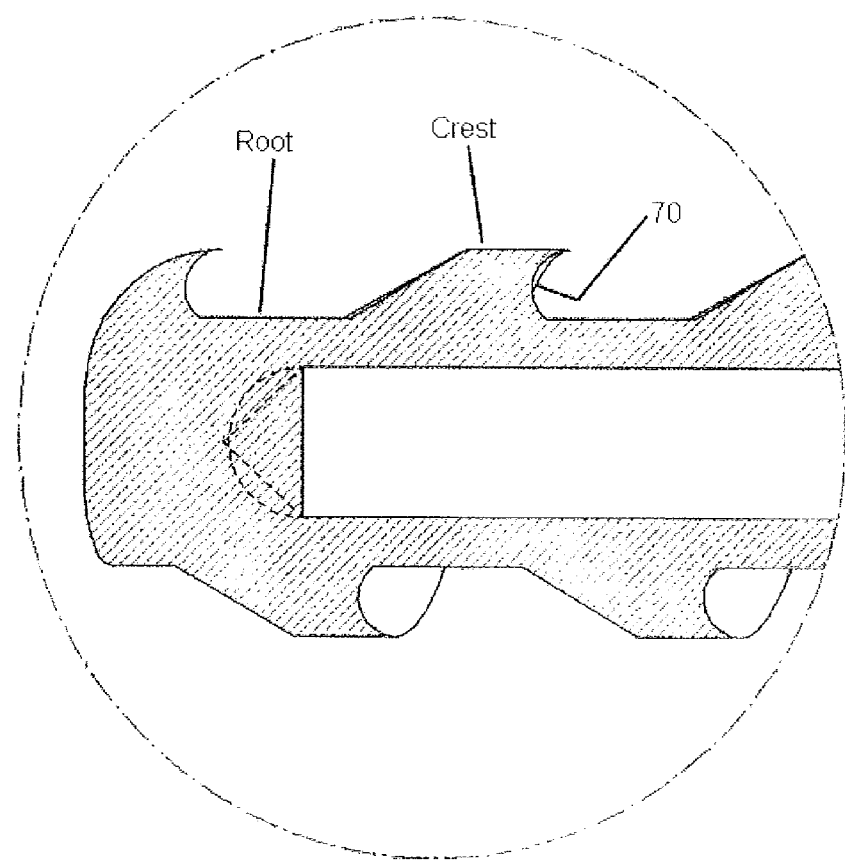
DETAIL B

FIG. 42
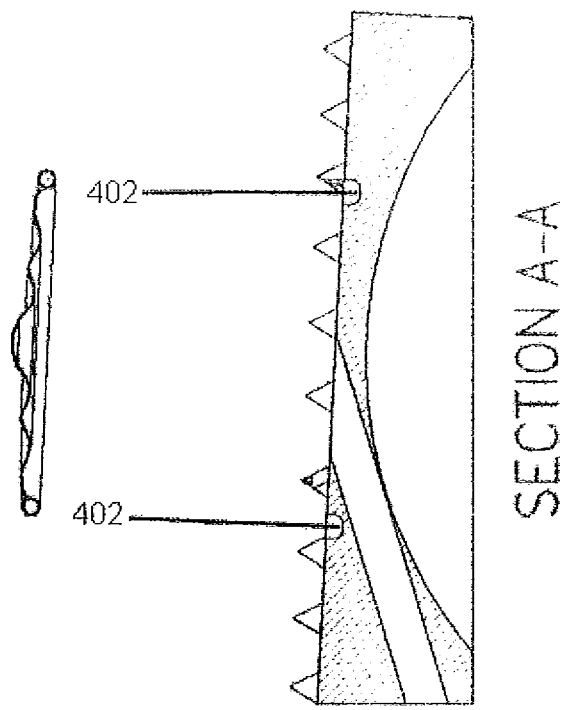
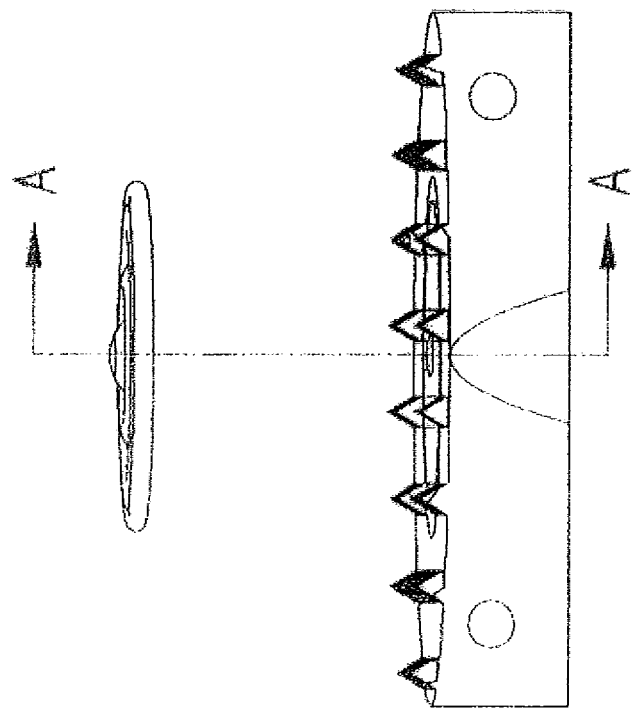

FIG. 45
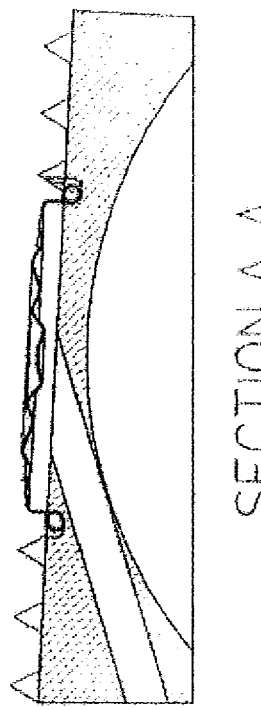
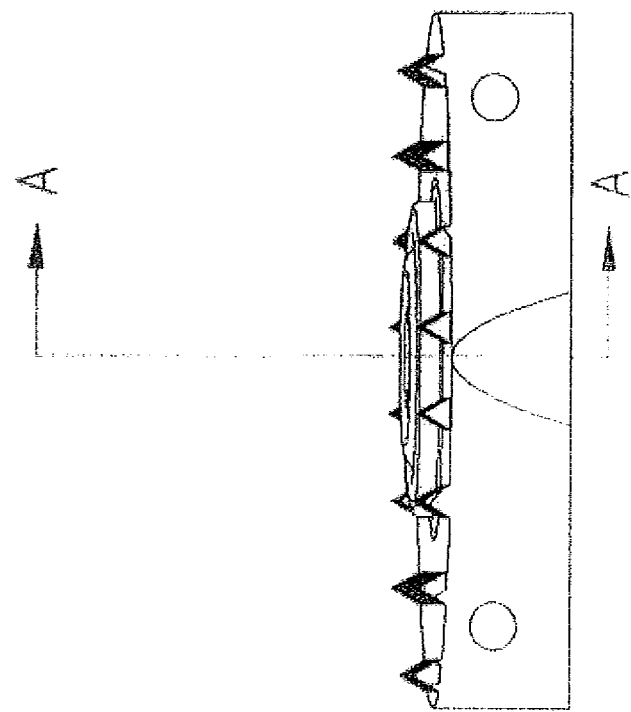
SECTION A-A

DYNAMIC SPINAL IMPLANTS INCORPORATING CARTILAGE BEARING GRAFT MATERIAL

RELATED APPLICATION

The present application claims priority to U.S. Provisional Application Ser. No. 60/761,540, entitled "DYNAMIC SPINAL IMPLANTS INCORPORATING CARTILAGE BEARING GRAFT MATERIAL," filed Jan. 24, 2006, the disclosure of which is hereby incorporated by reference.

FIELD OF THE INVENTION

The invention relates generally to methods and apparatus for the treatment of degenerative disc disease and associated conditions. More particularly, the present invention relates to the use of cartilage bearing graft material (allograft, autograft or xenograft) in dynamic disc replacement and/or facet arthroplasty.

BACKGROUND OF THE INVENTION

The spinal motion segment consists of a unit of spinal anatomy bounded by two vertebral bodies, including the two vertebral bodies, the interposed intervertebral disc, as well as the attached ligaments, muscles, and the facet joints. The disc consists of the end plates at the top and bottom of the vertebral bones, the soft inner core, called the nucleus and the annulus fibrosis running circumferentially around the nucleus. In normal discs, the nucleus cushions applied loads, thus protecting the other elements of the spinal motion segment. A normal disc responds to compression forces by bulging outward against the vertebral end plates and the annulus fibrosis. The annulus consists of collagen fibers and a smaller amount of elastic fibers, both of which are effective in resisting tension forces. However, the annulus is not very effective in withstanding compression and shear forces.

As people age the intervertebral discs often degenerate. This degeneration of the intervertebral discs may lead to degenerative disc disease. Degenerative disc disease of the spine is one of the most common conditions causing pain and disability in our population. When a disc degenerates, the nucleus dehydrates. When a nucleus dehydrates, its ability to act as a cushion is reduced. Because the dehydrated nucleus is no longer able to bear loads, the loads are transferred to the annulus and to the facet joints. The annulus and facet joints are not capable of withstanding the applied compression and torsional loads, and as such, they gradually deteriorate. As the annulus and facet joints deteriorate, many other effects ensue, including the narrowing of the interspace, bony spur formation, fragmentation of the annulus, fracture and deterioration of the cartilaginous end plates, and deterioration of the cartilage of the facet joints. The annulus and facet joints lose their structural stability and subtle but pathologic motions occur between the spinal bones.

As the annulus loses stability it tends to bow out and may develop a tear allowing nuclear material to extrude. Breakdown products of the disc and facet joint, including macroscopic chunks, microscopic particles, and noxious biochemical substances build up. These breakdown products stimulate sensitive nerve endings in and around the disc, producing low back pain and sometimes, sciatica. Affected individuals experience muscle spasms, reduced flexibility of the low back, and pain when ordinary movements of the trunk are attempted.

Degenerative disc disease is irreversible. In some cases, the body will eventually stiffen the joints of the motion segment, effectively re-stabilizing the discs. Even in the cases where re-stabilization occurs, the process can take many years and patients often continue to experience disabling pain. Extended painful episodes of longer than three months often leads patients to seek a surgical solution for their pain.

Several surgical techniques have been devised to attempt to stabilize the spinal motion segment. Some of these methods include: heating the annular region to destroy nerve endings and strengthen the annulus; applying rigid or semi-rigid support members on the sides of the motion segment or within the disc space; removing and replacing the entire disc with a non-flexible, articulating artificial device; removing and replacing the nucleus; and spinal fusion involving permanently fusing the vertebra adjacent the affected disc.

Until recently, spinal fusion has generally been regarded as the most widely used treatment to alleviate back pain due to degenerative disc disease. Most spinal fusion techniques utilize some form of rigid metal stabilizing mechanism, such as the BAK spinal cage, that fixes the mechanical relationship between the adjacent vertebra. Some investigational fusion devices similar to metal fusion cages are being manufactured from cortical bone. Two of these biological fusion devices are the PLIF Spacer, for posterior lumbar interbody fusion, and the FRA Spacer, for anterior lumbar interbody fusion.

While spinal fusion treatment is effective at relieving back pain, all discal motion is lost in the fused spinal motion segment. The loss of motion in the affected spinal segment necessarily limits the overall spinal mobility of the patient. Ultimately, the spinal fusion places greater stress on the discs adjacent the fused segment as these segments attempt to compensate for lack of motion in the fused segment, often leading to early degeneration of these adjacent spinal segments.

Current developments are focusing on treatments that can preserve some or all of the motion of the affected spinal segment. One of these methods to stabilize the spinal motion segment without the disadvantages of spinal fusion is total disc replacement. Total disc replacement involves removing the cartilaginous end plates between the vertebral bone and the disc, large portions of the outer annulus and the complete inner nucleus. If the entire disc is removed, typically an artificial prosthesis is placed in the disc space. Many of the artificial disc prosthesis currently available consist of a soft polymer to act as the nucleus. The soft polymer is interposed between two metal plates that are anchored or attached to the vertebral endplates. Examples of these layered total disc replacement devices are shown, for example, in U.S. Pat. Nos. 4,911,718, 5,458,643, 5,545,229 and 6,533,818, which are herein incorporated by reference.

An alternative to total disc replacement is nuclear replacement. Like the artificial disc prosthetics, these nuclear replacements are also inert, somewhat flexible, non-biological prosthetics. The procedure for implanting a nuclear replacement is less invasive than the procedure for a total disc replacement and generally includes the removal of only the nucleus and replacement of the nucleus with a prosthetic that may be malleable and provide cushioning that mimics a natural disc nucleus. Several of this disc replacement prosthetics utilize a hydrogel material because of the similarity of hydrogel to certain of the properties of a natural disc nucleus. Examples of the prosthetics used for nuclear replacement are shown, for example, in U.S. Pat. Nos. 4,772,287, 5,192,326, 5,919,235 and 6,726,721, which are herein incorporated by reference.

Although prosthetic devices have provided significant advances in the treatment of degenerative disc disease, almost all of these prosthetic devices suffer from the challenges of being non-biological devices. It would be desirable to provide for devices and techniques that can advance the treatment of degenerative disc disease without incurring the problems inherent in implanting a non-biological device.

SUMMARY OF THE INVENTION

The present invention incorporates a dynamic spinal implant that utilizes cartilage bearing graft material in dynamic disc replacement and/or facet arthroplasty. Methods and apparatus for dynamic spinal implants incorporate bulk articular graft tissues derived from donor joint sources in human (allograft or autograft) or non-human (xenograft) tissue. The donor joint is preferably prepared as a biological dynamic spinal implant with articular cartilage as a bearing interface between adjacent bone surfaces that naturally articulate with respect to one another.

In one embodiment, a generally cylindrically shaped section is taken from both the femoral head and acetabulum (and/or pelvis) of a donor to form the cartilage bearing graft material. Preferably, the teres ligament and/or its attachments to the acetabulum and/or femur may be preserved (and/or separated and subsequently re-fixed or re-attached to bone) to serve as a constraint feature of this embodiment to mitigate or eliminate the potential for dislocation and/or excessive translation and/or rotation of these embodiments of the present invention. While this embodiment utilizes a hip joint as the donor joint, it will be understood that other joints may also be used in conjunction with the methods and apparatus of the present invention, including the knee, hip, ankle, vertebra, wrist, elbow or shoulder.

In another embodiment, the biological dynamic spinal implant with articular cartilage includes a keying feature that may be generally seated against the anterior cortex of the vertebral body or within an aperture or opening formed in the anterior cortex of the anterior corpus of the vertebral body. This keying feature preferably allows for the inclusion and additional fixation by a secondary fixation element. Preferably, the biological dynamic spinal implant is provided with textured features on one or more of the exterior surfaces opposite the cartilage bearing bone surface for mitigation of migration, subsidence, expulsion, and/or micromotion of the implant.

In another embodiment, dynamic disc replacement and facet arthroplasty enabling correction of spondylothysthesis or other spinal pathology is accomplished by first implanting the dynamic disc replacement in a preliminary position through a more anterior approach and then implanting a facet arthroplasty device through a more posterior approach. Second, balancing out the relative locations and orientations of the implants is performed by way of dynamic balancing or static balancing of the adjacent vertebrae and adjacent soft tissue structures. Third, fixing the relative positions of the facet arthroplasty implants and dynamic disc replacement implants attached to a single vertebrae or adjacent vertebrae is performed with respect to each other.

The present invention provides methods and apparatus for dynamic spinal implants with a bone implant interface comprised of materials whose modulus of elasticity closes matches that of living bone tissue and with shock absorption characteristics mimicking or approaching that of the natural, healthy disc.

BRIEF DESCRIPTION OF THE DRAWINGS

Other important objects and features of the invention will be apparent from the following detailed description of the invention taken in connection with the accompanying drawings in which:

FIGS. 1-16 are pictorial representations of dynamic disc systems and spinal fusion systems of the prior art.

FIGS. 17-50 show various depictions of dynamic disc and/or facet arthroplasty methods and apparatus in accordance with preferred and alternate embodiments of the present invention.

DETAILED DESCRIPTION OF THE PREFERRED EMBODIMENTS

Figure 1:
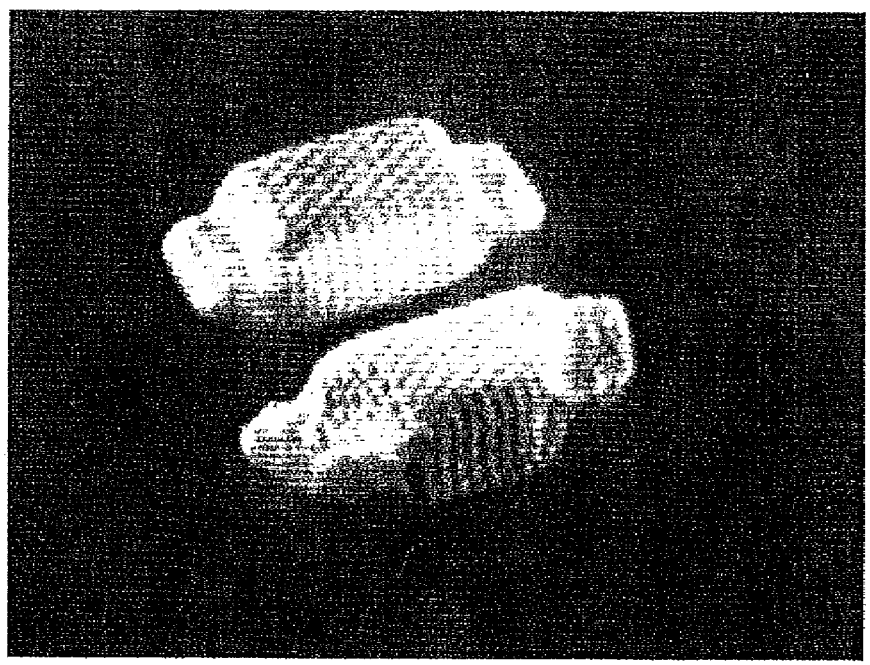

The intervertebral disc constitutes a major component of the functional spinal unit. Aging results in deterioration of the biological and mechanical integrity of the intervertebral discs. Disc degeneration may produce pain directly or perturb the functional spinal unit in such a way as to produce a number of painful entities. Whether through direct or indirect pathways, intervertebral disc degeneration is a leading cause of pain and disability in adults. Approximately 80% of Americans experience at least a single episode of significant back pain in their lifetime, and for many individuals, spinal disorders become a lifelong malady. The morbidity associated with disc degeneration and its spectrum of associated spinal disorders is responsible for significant economic and social costs. The treatment of this disease entity in the United States is estimated to exceed $60 billion annually in health care costs. The indirect economic losses associated with lost wages and decreased productivity are staggering.

Age-related disc changes occur early and are progressive. Almost all individuals experience diminished nuclear water content and increased collagen content by the time they are forty. This desiccation and fibrosis of the disc blur the nuclear/annular boundary. These senescent changes allow repeated minor rotational trauma to produce circumferential tears between annular layers. These defects, usually in the posterior or posterolateral portions of the annulus, may enlarge and combine to form one or more radial tears through which nuclear material may herniate. Pain and dysfunction due to compression of neural structures by herniated disc fragments are widely recognized phenomena. It should be noted, however, that annular injuries may be responsible for axial pain with or without the presence of a frank disc herniation.

Progression of the degenerative process alters intradiscal pressures, causing a relative shift of axial load-bearing to the peripheral regions of the endplates and facets. This transfer of biomechanical loads appears to be associated with the development of both facet and ligament hypertrophy. There is a direct relation between disc degeneration and osteophyte formation. In particular, deterioration of the intervertebral disc leads to increased traction on the attachment of the outermost annular fibers, thereby predisposing to the growth of laterally situated osteophytes. Disc degeneration also results in a significant shift of the instantaneous axis of rotation of the functional spinal unit. The exact long-term consequences of such a perturbation of spinal biomechanics are unknown, but it has been postulated that this change promotes abnormal loading of adjacent segments and an alteration in spinal balance.

Nonoperative therapeutic options for individuals with neck and back pain include rest, heat, analgesics, physical therapy, and manipulation. Unfortunately, these treatments fail in a significant number of patients. Current surgical management options for spinal disease include decompressive surgery, decompression with fusion, and fusion (arthrodesis) alone.

Greater than 200,000 discectomies are performed annually in the United States. Although discectomy is exceptionally effective in promptly relieving significant radicular pain, the overall success rates for these procedures range from 48% to 89%. In general, the return of pain increases with the length of time from surgery. Ten years following lumbar discectomy, 50-60% of patients will experience significant back pain and 20-30% will suffer from recurrent sciatica. In general, the reasons for these less than optimal results are probably related to continued degenerative processes, recurrent disc rupture, instability, and spinal stenosis.

There are several specific reasons for failure of surgical discectomy. The actual disc herniation may not have been the primary pain generator in some patients. A number of relapses are due to disc space collapse. Although the disc height is often decreased in the preoperative patient with a herniated nucleus pulposus, it is an exceedingly common occurrence following surgical discectomy. Disc space narrowing is very important in terms of decreasing the size of the neural foramina and altering facet loading and function. Disc space narrowing increases intra-articular pressure, and abnormal loading patterns have been shown to produce biochemical changes in the intra-articular cartilage at both the level of the affected disc and the adjacent level. The entire process predisposes to the development of hypertrophic changes of the articular processes. Disc space narrowing also allows for rostral and anterior displacement of the superior facet. This displacement of the superior facet becomes significant when it impinges upon the exiting nerve root which is traversing an already compromised foramen. Destabilization of the functional spinal unit is another potential source of continued pain. A partial disc excision is associated with significant increases in flexion, rotation, lateral bending, and extension across the affected segment. As the amount of nuclear material which is removed increases, stiffness across the level decreases accordingly. Disc excision has also been demonstrated to lead to instability at the level above the injured segment in cadaver studies. This situation has been documented to occur clinically as well.

Arthrodesis or spinal fusion, with or without decompression, is another means of surgically treating symptomatic spondylosis in all regions of the mobile spine. Fusion has the capability of eliminating segmental instability, maintaining normal disc space height, preserving sagittal balance, and halting further degeneration at the operated level. Discectomy with fusion has been the major surgical treatment for symptomatic cervical spondylosis for over 40 years. The major rationale for spinal arthrodesis is that pain can be relieved by eliminating motion across a destabilized or degenerated segment. Good to excellent results have been reported in 52-100% of anterior lumbar interbody fusions and 50-95% of posterior lumbar interbody fusions.

Spinal fusion is not, however, a benign procedure. In numerous patients, recurrent symptoms develop years after the original procedure. Fusion perturbs the biomechanics of adjacent levels. Hypertrophic facet arthropathy, spinal stenosis, disc degeneration, and osteophyte formation have all been reported to occur at levels adjacent to a fusion, and these pathological processes are responsible for pain in many patients. In at least one study, the long-term results of lumbar fusions have shown that roughly half of patients had lumbar pain requiring medication at last follow-up, and about 15% had been treated with further surgery. Finally, there are a number of other drawbacks to fusion as a treatment for spinal pain, including loss of spinal mobility, graft collapse resulting in alterations of sagittal balance, autograft harvest site pain, and the possibility of alteration of muscular synergy.

Instead of spinal fusion, various approaches have been proposed for an artificial or prosthetic disc. The idea of spinal disc replacement is not new. One of the first attempts to perform disc arthroplasty was undertaken by Nachemson 40 years ago. Fernstrom attempted to reconstruct intervertebral discs by implanting stainless steel balls in the disc space. These pioneering efforts were followed by more than a decade of research on the degenerative processes of the spine, spinal biomechanics, and biomaterials before serious efforts to produce a prosthetic disc resumed.

There are a number of factors that must be considered in the design and implantation of effective disc prostheses. The device must maintain the proper intervertebral spacing, allow for motion, and provide stability. Natural discs also act as shock absorbers, and this may be an important quality to incorporate into replacement disc design, particularly when considered for multilevel lumbar reconstruction. The replacement disc must not shift significant axial load to the facets. Placement of the replacement disc must be done in such a way as to avoid the destruction of important spinal elements such as the facets and ligaments. The importance of these structures cannot be overemphasized. Facets not only contribute strength and stability to the spine, but they could be a source of pain. This may be especially important to determine prior to disc arthroplasty because it is currently believed that disc replacement will probably be ineffective as a treatment for facet pain. Excessive ligamentous laxity may adversely affect disc replacement outcome by predisposing to implant migration or spinal instability.

A replacement disc must exhibit tremendous endurance. The average age of a patient needing a lumbar disc replacement has been estimated to be 35 years. This means that to avoid the need for revision surgery, the replacement disc must last 50 years. It has been estimated that an individual will take 2 million strides per year and perform 125,000 significant bends; therefore, over the 50-year life expectancy of the artificial disc, there would be over 106 million cycles. This estimate discounts the subtle disc motion which may occur with the 6 million breaths taken per year. A number of factors in addition to endurance must be considered when choosing the materials with which to construct an intervertebral disc prosthesis. The materials must be biocompatible and display no corrosion. They must not incite any significant inflammatory response. The fatigue strength must be high and the wear debris minimal. Finally, it would be ideal if the implant were imaging "friendly."

All currently proposed intervertebral disc prostheses are contained within the disc space; therefore, allowance must be made for variations in patient size, level, and height. There may be a need for instrumentation to restore collapsed disc space height prior to placement of the prosthesis. The intervertebral disc replacement ideally would replicate normal range of motion in all planes. At the same time it must constrain motion. A disc replacement must reproduce physiologic stiffness in all planes of motion plus axial compression. Furthermore, it must accurately transmit physiologic stress. For example, if the global stiffness of a device is physiologic but a significant non-physiologic mismatch is present at the bone-implant interface, there may be bone resorption, abnormal bone deposition (likely leading to osteophyte overgrowth, impingement of the spinal cord and subsequent stenosis), and endplate or implant failure.

The disc replacement preferably must have immediate and long-term fixation to bone. Immediate fixation may be accomplished with screws, staples, or "teeth" which are integral to the implant. While these techniques may offer long-term stability, other options include porous or macrotexture surfaces which allow for bone ingrowth. Regardless of how fixation is achieved, there must also be the capability for revision. Finally, the implant must be designed and constructed such that failure of any individual component will not result in a catastrophic event. Furthermore, neural, vascular, and spinal structures must be protected and spinal stability maintained in the event of an accident or unexpected loading.

Existing prosthetic discs have been constructed based on the utilization of one of the following primary properties: hydraulic, elastic, mechanical, and composite.

PDN Prosthetic Disc Nucleus—Hydrogel disc replacements primarily have hydraulic properties. Hydrogel prostheses are used to replace the nucleus while retaining the annulus fibrosis. One potential advantage is that such a prosthesis may have the capability of percutaneous placement. The PDN implant is a nucleus replacement which consists of a hydrogel core constrained in a woven polyethylene jacket (Raymedica, Inc., Bloomington, Minn.) (FIG. 1). The pellet-shaped hydrogel core is compressed and dehydrated to minimize its size prior to placement. Upon implantation, the hydrogel immediately begins to absorb fluid and expand. The tightly woven ultrahigh molecular weight polyethylene allows fluid to pass through to the hydrogel. This flexible but inelastic jacket permits the hydrogel core to deform and reform in response to changes in compressive forces yet constrains horizontal and vertical expansion upon hydration. Although most hydration takes place in the first 24 hours after implant, it takes approximately 4-5 days for the hydrogel to reach maximum expansion. Placement of two PDN implants within the disc space provides the lift that is necessary to restore and maintain disc space height. This device has been extensively assessed with mechanical and in vitro testing, and the results have been good. Schönmayr et al. reported on 10 patients treated with the PDN with a minimum of 2 years follow-up. Significant improvement was seen in both the Prolo and Oswestry scores, and segmental motion was preserved. Overall, 8 patients were considered to have an excellent result. Migration of the implant was noted in 3 patients, but only 1 required reoperation. One patient, a professional golfer, responded favorably for 4 months until his pain returned. He had marked degeneration of his facets, and his pain was relieved by facet injections. He underwent a fusion procedure and since has done well. The devices have been primarily inserted via a posterior route. Bertagnoli recently reported placing the PDN via an anterolateral transpsoatic route. The PDN is undergoing clinical evaluation in Europe, South Africa, and the United States.

Figure 2:
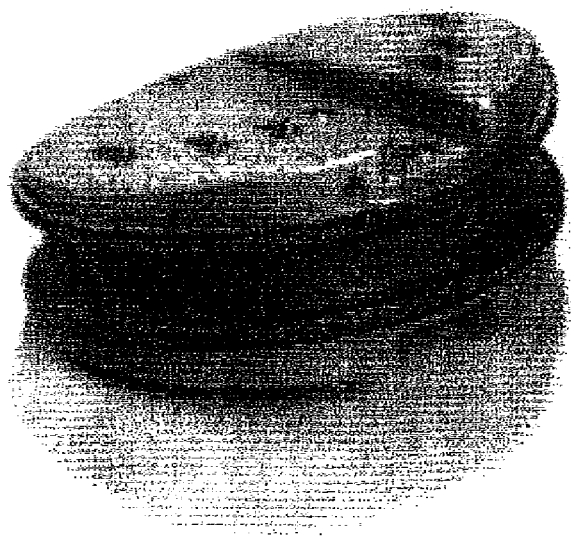

Acroflex Disc—Two elastic type disc prostheses are the Acroflex prosthesis proposed by Steffee and the thermoplastic composite of Lee. The first Acroflex disc consisted of a hexene-based polyolefin rubber core vulcanized to two titanium endplates. The endplates had 7 mm posts for immediate fixation and were coated with sintered 250 micron titanium beads on each surface to provide an increased surface area for bony ingrowth and adhesion of the rubber. The disc was manufactured in several sizes and underwent extensive fatigue testing prior to implantation. Only 6 patients were implanted before the clinical trial was stopped due to a report that 2-mercaptobenzothiazole, a chemical used in the vulcanization process of the rubber core, was possibly carcinogenic in rats. The 6 patients were evaluated after a minimum of 3 years, at which time the results were graded as follows: 2 excellent, 1 good, 1 fair, and 2 poor. One of the prostheses in a patient with a poor result developed a tear in the rubber at the junction of vulcanization. The second generation Acroflex-100 consists of an HP-100 silicone elastomer core bonded to two titanium endplates (DePuy Acromed, Raynham, Mass.) (FIG. 2).

Articulating Discs—Several articulating pivot or ball type disc prostheses have been developed for the lumbar spine. Hedman and Kostuik developed a set of cobalt-Chromium-molybdenum alloy hinged plates with an interposed spring. These devices have been tested in sheep. At 3 and 6 months post-implantation there was no inflammatory reaction noted and none of the prostheses migrated. Two of the three 6-month implants had significant bony ingrowth. It is not clear whether motion was preserved across the operated segments. Dr. Thierry Marnay of France developed an articulating disc prosthesis with a polyethylene core (Aesculap AG & Co. KG., Tuttlingen, Germany). The metal endplates have two vertical wings and the surfaces which contact the endplates are plasma-sprayed with titanium. Good to excellent results were reported in the majority of patients receiving this implant.

Figure 3:
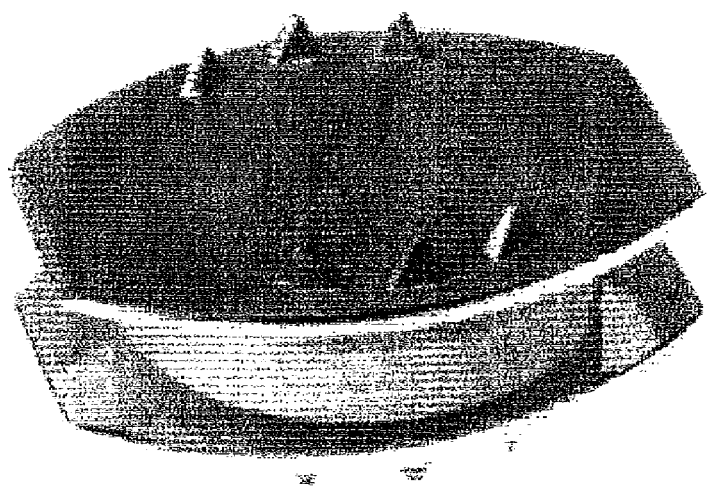

Link SB Charité Disc—The most widely implanted disc to date is the Link SB Charité disc (Waldemar Link GmbH & Co, Hamburg, Germany). The Charité III consists of a biconvex ultra high molecular weight polyethylene (UHMWPE) spacer. There is a radiopaque ring around the spacer for x-ray localization. The spacers are available in different sizes. This core spacer interfaces with two separate endplates. The endplates are made of casted cobalt-chromium-molybdenum alloy, each with three ventral and dorsal teeth. The endplates are coated with titanium and hydroxyapatite to promote bone bonding (FIG. 3).

Although there is great concern regarding wear debris in hip prostheses in which woven ultrahigh molecular weight polyethylene articulates with metal, this does not appear to occur in the Charité III. This prosthesis has been implanted in over a thousand European patients with relatively good results. In 1994 Griffith et al. reported the results in 93 patients with 1-year follow-up. Significant improvements in pain, walking distance, and mobility were noted. 6.5% of patients experienced a device failure, dislocation, or migration. There were 3 ring deformations, and 3 patients required reoperation. Lemaire et al. described the results of implantation of the SB Charité III disc in 105 patients with a mean of 51 months of follow-up. There was no displacement of any of the implants, but 3 settled. The failures were felt to be secondary to facet pain. David described a cohort of 85 patients reviewed after a minimum of at least 5 years post-implantation of the Charité prosthesis. 97% of the patients were available for follow-up. 68% had good or better results. 14 patients reported the result as poor. Eleven of these patients underwent secondary arthrodesis at the prosthesis level. Clinical trials using the Charité III prosthesis are ongoing in Europe, the United States, Argentina, China, Korea, and Australia.

Figure 4:
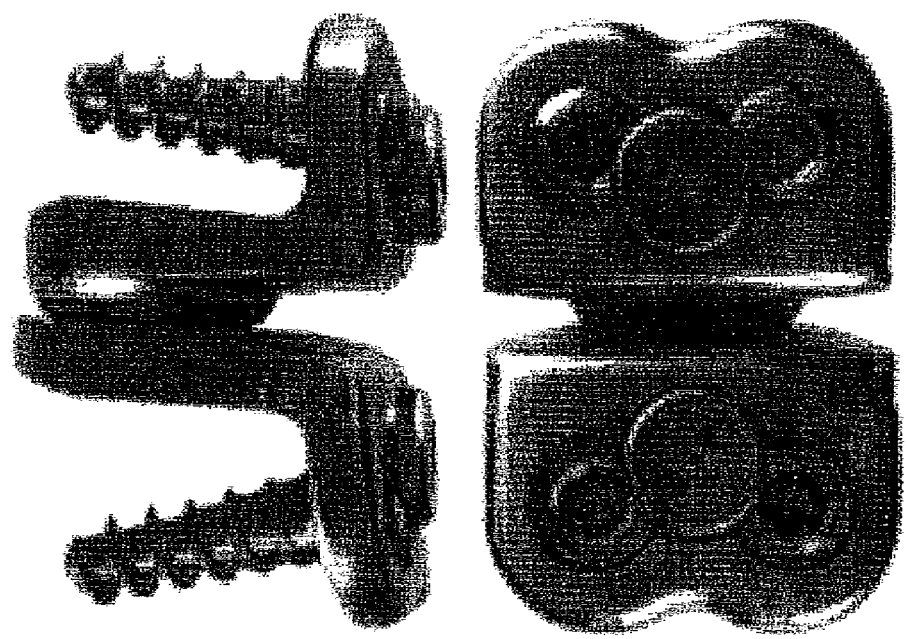
Figure 9:
Figure 10:
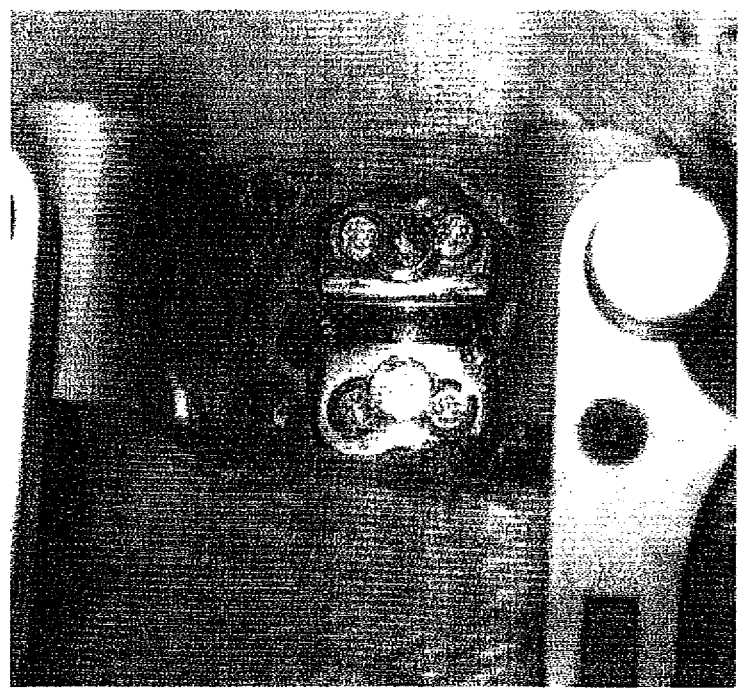

The Bristol Disc—There have been several reports on results from a cervical disc prosthesis that was originally developed in Bristol, England. This device was designed by Cummins. The original design has been modified. The second generation of the Cummins disc is a ball and socket type device constructed of stainless steel. It is secured to the vertebral bodies with screws. Cummins et al. described 20 patients who were followed for an average of 2.4 years. Patients with radiculopathy improved, and those with myelopathy either improved or were stabilized. Of this group, only 3 experienced continued axial pain. Two screws broke, and there were two partial screw back-outs. These did not require removal of the implant. One joint was removed because it was "loose." The failure was due to a manufacturing error. At the time of removal, the joint was firmly imbedded in the bone and was covered by a smooth scar anteriorly. Detailed examination revealed that the ball and socket fit was asymmetric. It is important to note that the surrounding tissues did not contain any significant wear debris. Joint motion was preserved in all but 2 patients (FIGS. 4, 9, and 10). Both of these patients had implants at the C6-7 level which were so large that the facets were completely separated. This size mismatch was felt to be the reason motion was not maintained. Subsidence did not occur. This disc prosthesis is currently being evaluated in additional clinical studies in Europe and Australia.

Figure 5:
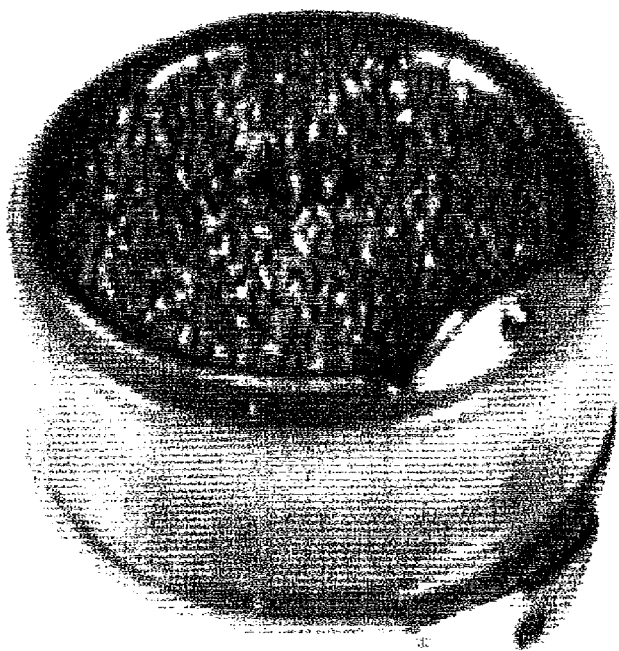
Figure 6:
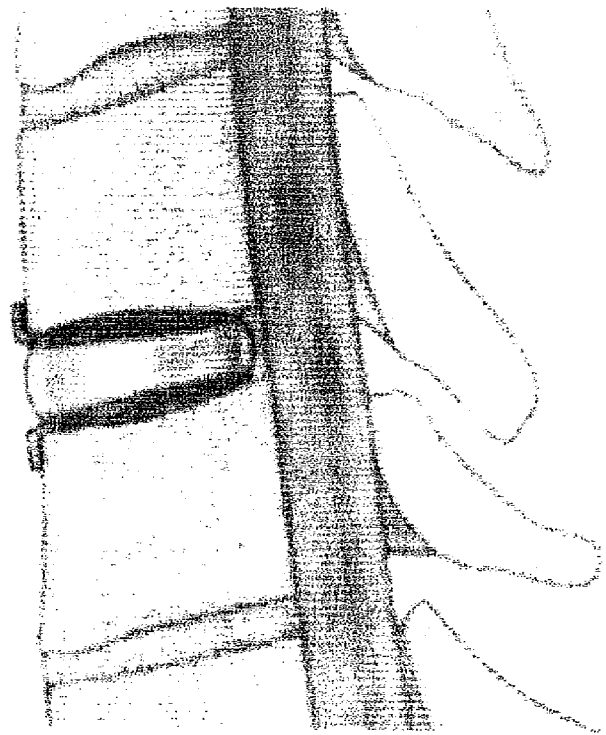
Figure 7:
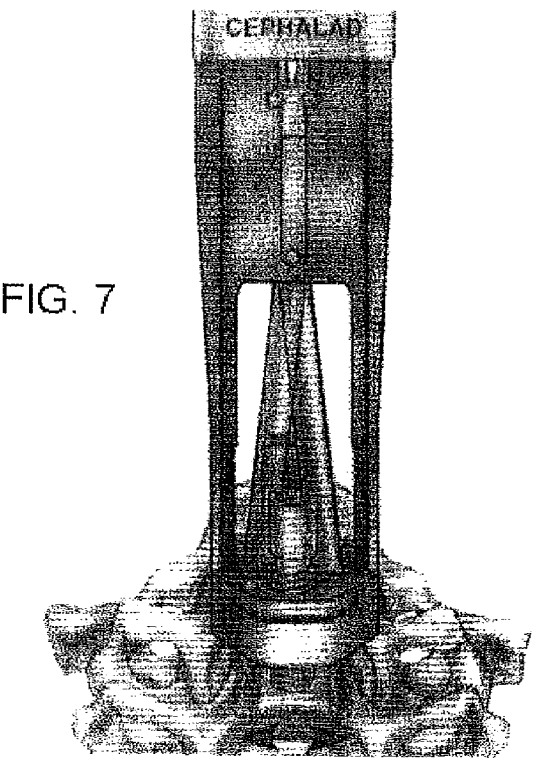
Figure 8:
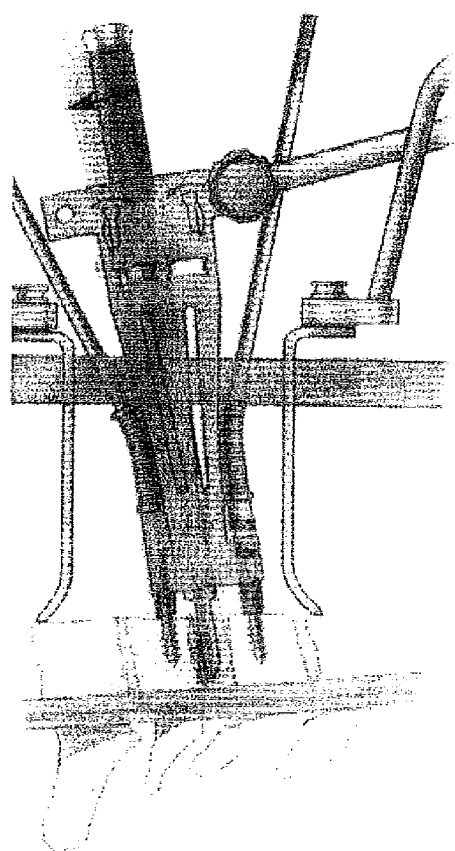

Bryan Cervical Disc Prosthesis—The Bryan Cervical Disc System (Spinal Dynamics Corporation, Seattle) is designed based on a proprietary, low friction, wear resistant, elastic nucleus. This nucleus is located between and articulates with anatomically shaped titanium plates (shells) that are fitted to the vertebral body endplates (FIGS. 5 and 6). The shells are covered with a rough porous coating. A flexible membrane that surrounds the articulation forms a sealed space containing a lubricant to reduce friction and prevent migration of any wear debris that may be generated. It also serves to prevent the intrusion of connective tissue. The implant allows for normal range of motion in flexion/extension, lateral bending, axial rotation, and translation. The implant is manufactured in five sizes ranging from 14 mm to 18 mm in diameter. The initial clinical experience with the Bryan Total Cervical Disc Prosthesis has been promising. 52 devices were implanted in 51 patients by 8 surgeons in 6 centers in Belgium, France, Sweden, Germany, and Italy. There were no serious operative or postoperative complications. Twenty-six of the patients have been followed for 6 months, and complete clinical and radiographic data is available on 23 patients. 92% of the patients were classified as excellent or good outcomes at last follow-up. Flexion/extension motion was preserved in all patients, and there was no significant subsidence or migration of the devices. FIGS. 7 and 8 demonstrate the endplate preparation technique used to prepare the spine to receive the Bryan Cervical Disc Implant. This technique and others for endplate preparation are herein included by reference in their entirety and are to be relied upon as support in this specification for claims.

Figure 11:
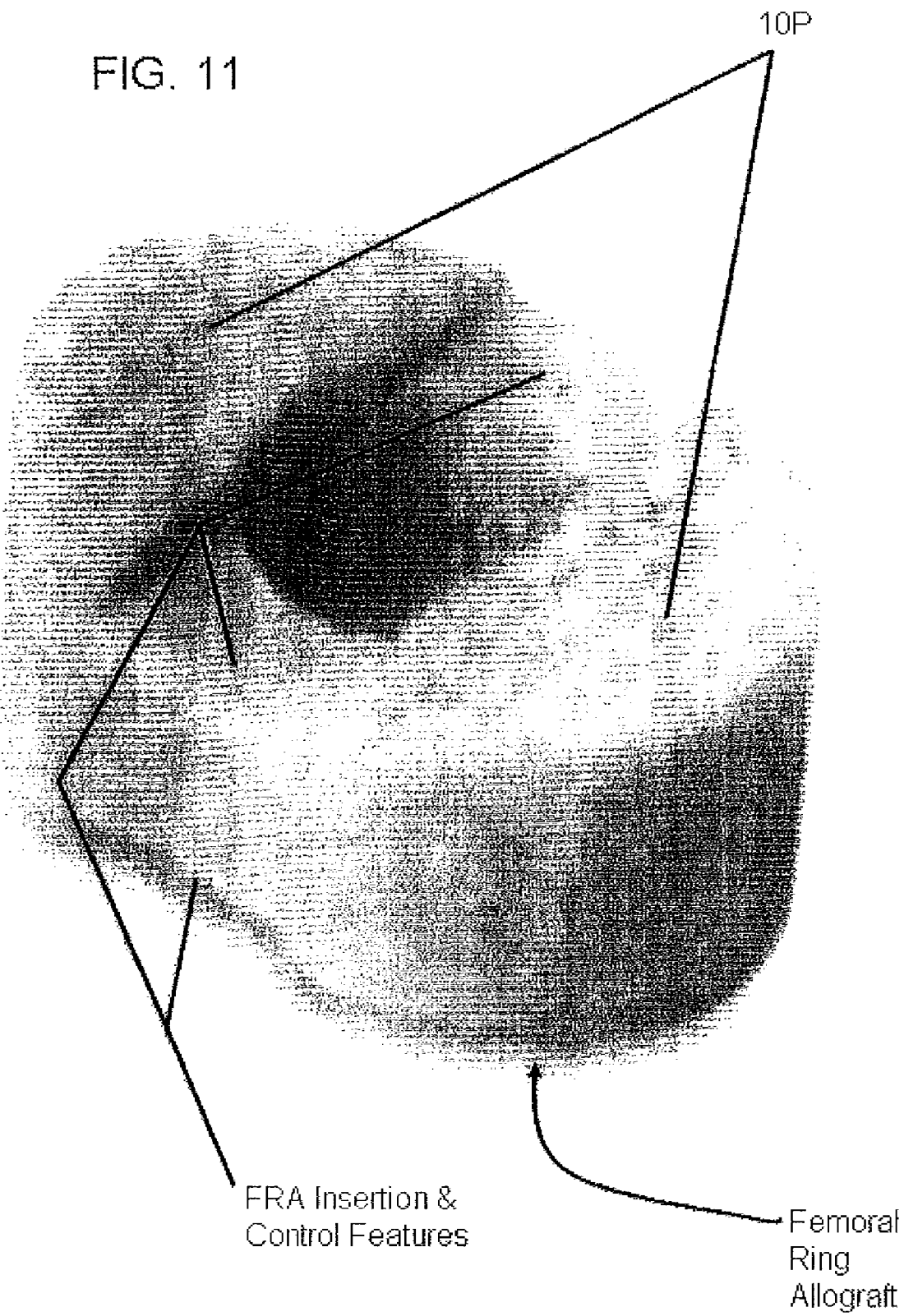
Figure 12:
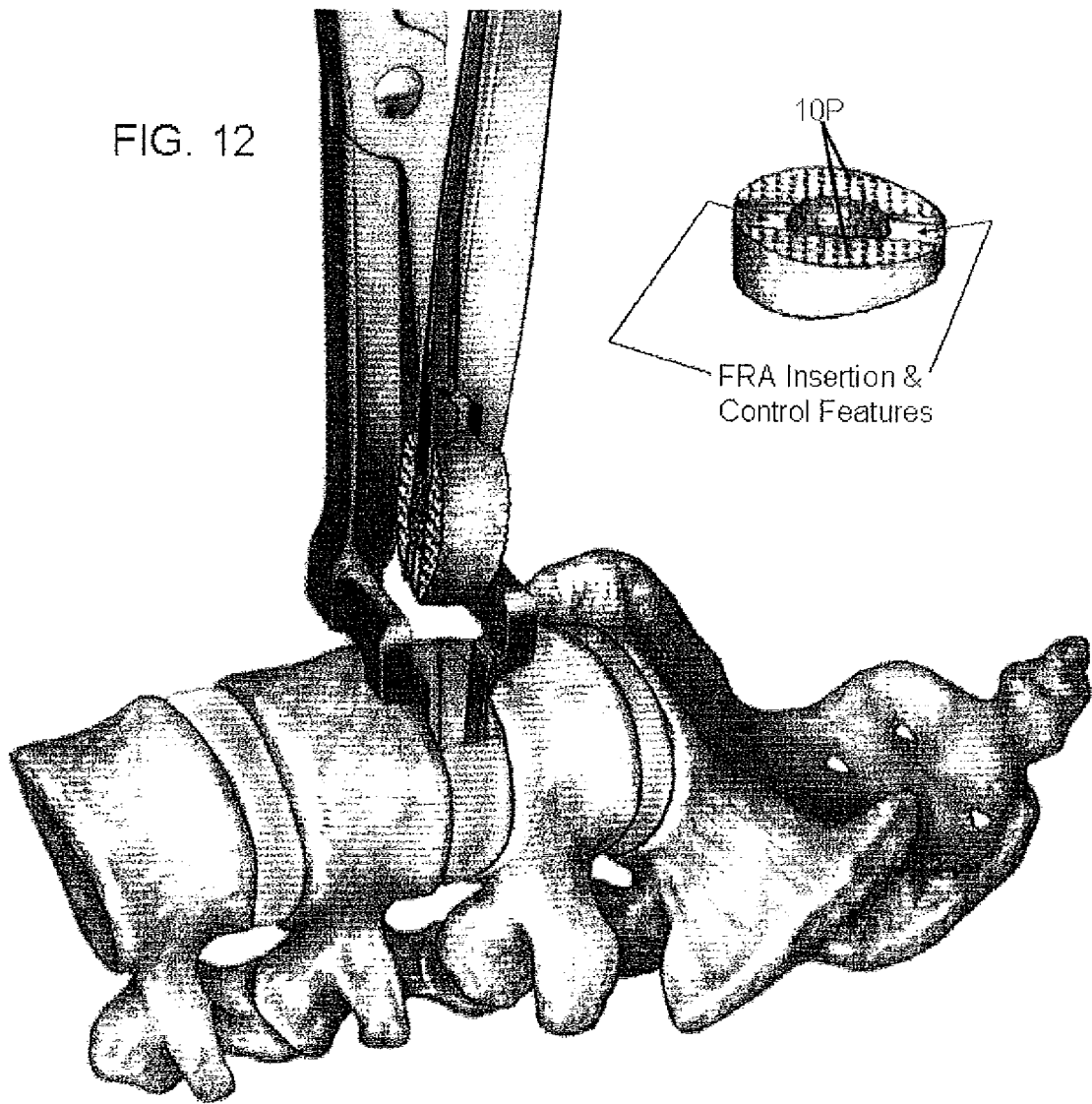
Figure 13:
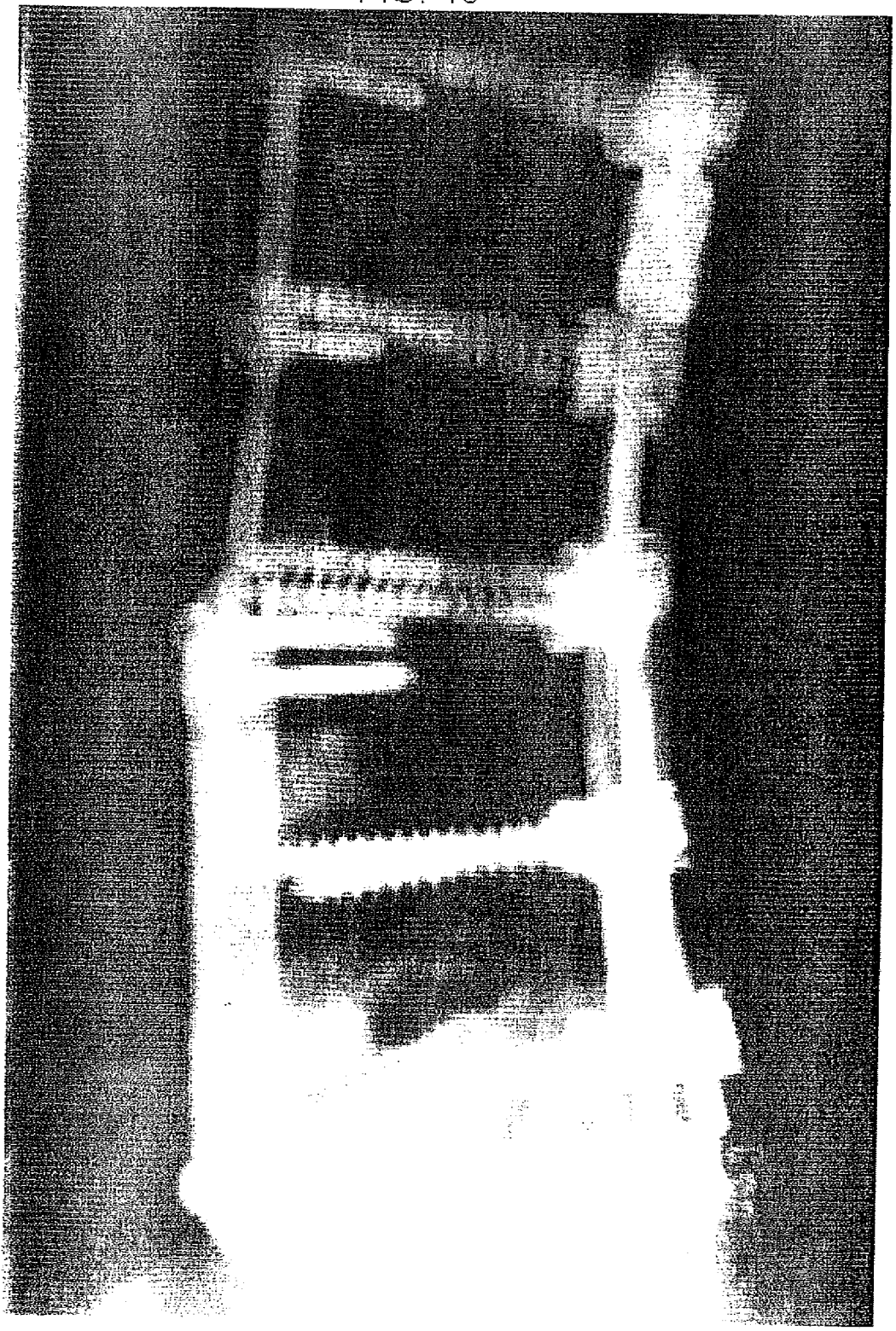

Interbody Fusion with Allograft—Two newly developed biological cages have been developed for posterior lumbar interbody fusion and anterior interbody fusion: the FRA Spacer (FIGS. 11, 12, and 13) and the PLIF Spacer (not shown) that are used for anterior lumbar interbody fusion and posterior lumbar interbody fusion, respectively. It should be noted that FIG. 13 shows a series of FRAs placed in multiple levels with both posterior and anterior instrumentation.

One of the early supporters and leading figures in posterior lumbar interbody fusion using bone grafts was Ralph Cloward. Cloward's innovative ideas contributed to the rectangular bone grafts and certain instruments used even today to insert bone grafts. Over the years, many variations of the posterior lumbar interbody fusion have been invented to facilitate the fusion process while maintaining stability to the spine. Capener first described anterior lumbar interbody fusions for spondylolisthesis in 1932. The year 1933 represented a pivotal year for anterior interbody fusion when Burns inserted an autologous tibial peg anteriorly into the L5-S1 intervertebral space. Today, spinal fusion can be accomplished by various techniques such as posterior procedures with and without internal fixation, anterior procedures with and without internal fixation, combined anterior and posterior column procedures which may include a posterior lumbar interbody fusion (PLIF) or anterior lumbar interbody fusion (ALIF) for anterior column support.

During the last decade, an increasing number of studies have looked toward the morphology, physiology, biomechanics, and immunology of the various components of the spine. Today, there are several options available to spinal surgeons for correcting spinal instabilities to regain physiological anterior column support. Among these are autograft, allograft, synthetics and metallic fusion cages. Fresh autologous cancellous bone is considered the best choice for osseous reconstruction because of its optimal biologic behavior and histocompatibility. However, autologous bone has inadequate initial mechanical strength for interbody loading and may collapse and/or extrude. Significant morbidity is also associated with anterior structural graft harvesting of the ilium and may result in infection, chronic pain, incisional hernias, vascular injuries, neurologic injuries and iliac wing fracture. The use of allograft is a safe, simple and inexpensive method of harvesting bone. Total operative time and blood loss can be reduced, and possible complications associated with the donor site can be avoided. Through continued clinical research devices are being manufactured from cortical bone, similar to metal fusion cages, providing built-in lordosis and end-plate gripping "teeth" for additional stability. Two of these biological devices are the PLIF Spacer, for posterior lumbar interbody fusion, and the FRA Spacer, for anterior lumbar interbody fusion.

Even when subjected under an axial load of 8,000N, the spine is capable of moving in flexion, extension, and rotation. In order to maintain stability under demanding conditions, the spine is dependent upon the articulating processes of the intervertebral and the facet joints. Similar to the cervical spine, the lumbar spine has a lordotic curvature that is essential to its function. Because of its location and shape, the lumbar spine often fails under axial compression. For these reasons, a successful biological cage needs to address both the lordosis of the lumbar spine while providing stability to the spine.

Figure 14:
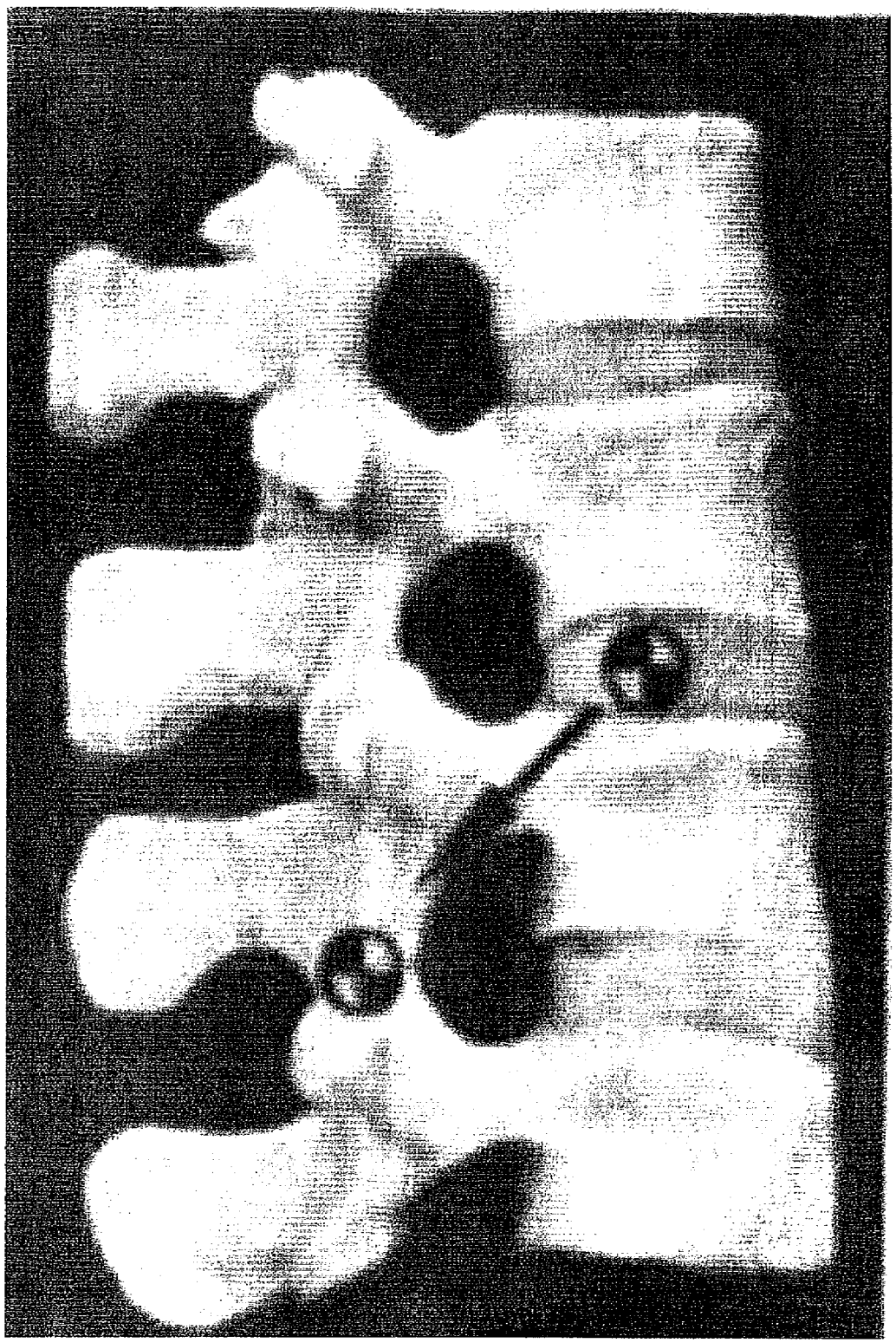
Figure 15:
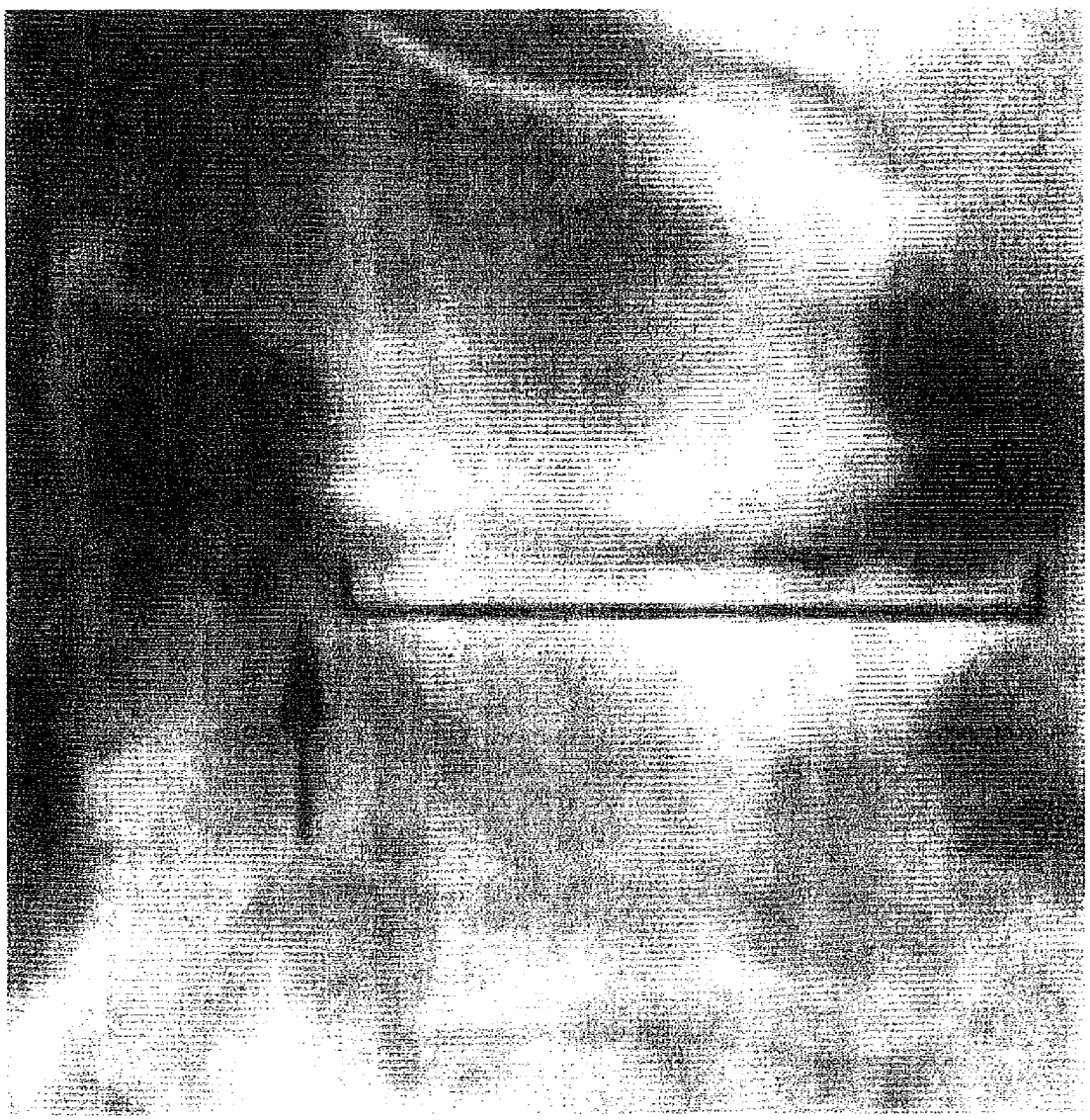

The anterior column of the spine absorbs 80% of an axial compressive force while the posterior structures absorb the remaining 20%. A study by Brown and colleagues of motion segments of the lumbar region with static compressive loads indicated that the first component to fail was the vertebral body. This occurred as a result of the fractured end-plates. These findings suggest that the vertebral body's strength is dependent on intact end-plates. FIGS. 14 and 15 are included herein to generally illustrate the morphological changes induced by deterioration of the disc. FIG. 14 is a plastic model showing "plump and healthy" discs and vertebral bodies in their "natural and healthy" state (the center points and arrow shown demonstrate the change that occurs in the center of rotation of adjacent vertebrae with respect to each other as the disc and facets degenerate from their healthy state to a degenerated state, respectively). FIG. 15 is a radiograph of a completely collapsed disc space showing the changes in shape undergone by the vertebral bodies, the formation of osteophyte overgrowth in response to excessive bone on bone contact between the vertebral bodies (indicated by the horizontally oriented bracket), and the impingement of the vertebral bodies upon the spinal cord (the arrow indicating the impingement site) leading to a relatively classic case of stenosis.

The facet joints and the pars interarticularis control the movement of the posterior elements of the spine. According to Nachemsom, the facets carry about 18% of the total compressive load of a motioned segment. When the body is in flexion, the facet serves to provide stability to the spine. Farfan and Sullivan established a correlation between facet joints asymmetry and the level of disc pathology. An ideal implant must be capable of withstanding the axial compressive force of the body. In addition, it must be able to displace the compressive force without inducing a great deal of motion in the adjacent segment while also promoting arthrodesis. The quality of the bone graft both biologically and as a load-bearing device is essential in achieving a solid fusion. Biological cages have been recently developed to address the criteria for both anterior and posterior interbody fusion.

Tests had been conducted by third parties on the PLIF and FRA Spacers to ensure that they could withstand the loads in the lumbar spine. The ultimate compressive strength of a vertebral body is 8000 N. Test results show that the PLIF and FRA Spacers have a compressive strength over 25,000 N. A successful interbody fusion will restore every mechanical function of the functional spinal unit except motion. The bone graft must bear substantially all of the body's weight above the fusion level(s) while it is being incorporated. The goal for any spinal fusion is to maintain the correction, avoid hardware or graft failure and obtain a solid fusion.

In addition to compressive strength, resistance to implant expulsion is a major factor in the design of intervertebral spacers. The PLIF Spacer is designed with saw-tooth-shaped teeth to increase resistance to pullout. Pullout testing was conducted to ensure that the spacer was able to resist expulsion. The maximum shear force that a human disc can withstand is about 150N. An axial preload (450 N) and a shear load were applied to the implant to determine the pullout strength. Test results show that the PLIF Spacer has a pullout strength of (1053 N±80 N), more than three times the pullout strength of a comparable design without teeth (234 N±38 N). Testing was conducted on the FRA Spacer to ensure that it was capable of resisting expulsion at clinically relevant loads. The resistance of the implant to being expelled from the disc space was determined by pushout testing. A clinically relevant load (450N) and side load was applied to the implant to determine the pushout strength. Pyramid shaped teeth are machined on the upper and lower surfaces of the implant to increase resistance to pushout. Test results show that the FRA Spacer has a pushout strength (1236N±132N) three times the pushout strength of a comparable femoral wedge (405N±65N).

In the past 40 years spine instrumentation and techniques have increased dramatically. Accompanying the rise is the demand for bone allograft. In many aspects, bone autograft is more advantageous than allografts; however, the clinical demand for bone allograft in limb salvage, fractures, and joint replacements necessitate its use. In order to understand how allografts are utilized, one must examine the biology and the screening process of allografts. An inflammatory process occurs within hours after the graft has been implanted. There are five processes involved in the incorporation of the graft. The first stage of the graft is the inflammatory process, which is followed by revascularization, osteogenesis, remodeling, and finally mechanical stability. During the inflammatory stage the body's defenses elicit an immune response causing inflammatory cells such as neutrophils and fibroblasts to invade the graft. Rejection of the graft often occurs during revascularization where the host is highly sensitive to the graft's antigen. During revascularization, possible complications may occur, including graft necrosis and occlusion of the host vessels. Osteogenesis refers to the synthesis of new bone by the host and begins shortly after the immediate postoperative period. This process involves the mesenchymal cells proliferating, and eventually differentiating into chondrocytes and later into osteoblasts. Osteoconduction refers to the graft's ability to induce osteogenesis, which can persist for several months following surgery. Remodeling and mechanical stability follows, producing a functional and efficient graft. Because allografts are capable of eliciting a more aggressive immune response, freeze drying, cryopreservation, and other preservation techniques are used to delay the inflammatory and revascularization process.

The PLIF and FRA Spacers are harvested and processed by the musculoskeletal transplant foundation (MTF) which is a national consortium of medical schools, academic institutions and recovery organizations involved in the aseptic recovery, processing and distribution of bone and related soft tissue for use in transplant surgery. Its quality and safety standards consistently meet or exceed the requirements of the American Association of Tissue Banks (AATB) and the guidelines for screening and testing of tissue donors set forth by the FDA. MTF is AATB accredited and uses the most complete and technically advanced testing available to assure the safety of its allografts. MTF was the first tissue bank to utilize HIV DNA by Polymerase Chain Reaction (PCR) testing on every donor. In independent testing, PCR has been found to be 99.6% sensitive and 99.9% specific. MTF continues to require this testing in its routine screening of donors. Since its inception, MTF has recovered and processed over 15,000 donors. It has distributed more than 700,000 tissues without a confirmed disease transmission, including HIV.

To maintain biological integrity, MTF processes all tissue by using aseptic techniques in class 10 (certified) clean rooms. This eliminates the need for terminal sterilization by high-dose gamma irradiation or ethylene oxide gas, which have been shown to compromise the biological and biomechanical integrity of allograft tissue. All tissue undergoes a total of 27 separate quality assurance checks prior to release. All tissue is computer tracked from recovery through testing, processing, packaging and distribution. The age criteria for donors are 15-60 for males and 15-55 for females. This allows the selection of tissue with denser construction. All potential donors must pass through a comprehensive quality assurance process. Screening begins at the site of recovery, with a comprehensive medical and social history that includes the cause of death. Tissue and blood samples are tested for infectious diseases that include hepatitis, HIV, and syphilis. The MTF's testing requirements exceed current AATB and FDA guidelines. A team of medical/technical specialists from the infectious disease and tissue banking fields evaluates all information, including test results. The PLIF and FRA Spacers are preserved between −40° C. and −90° C. until time of shipping, and are shipped on dry ice. The grafts are stored in a −40° C. to −90° C. freezer until the time of surgery.

A successful posterior lumbar interbody fusion using a biological disc cage restores the disc height, opens the neural foramen, stabilizes the spinal segment, and provides anterior column support. Distracting the segment in a posterior lumbar interbody fusion is essential to the prosperity of the surgery. There are two major surgical techniques that may be used to distract, size, and insert the PLIF Spacer; distraction with the PLIF Distractor and distraction with the PLIF Trial Spacer. The surgical technique used depends upon the patient's local anatomy, the pathology, and the surgeon's preference. The PLIF Distractor distracts the vertebrae to ensure maximum implant height and neural foraminal decompression. The PLIF Distractor distracts on one side while the PLIF Spacer is inserted on the contralateral side. The PLIF Trial Spacer ensures accurate sizing of the PLIF Spacer. There are 5 sizes ranging from 9-17 mm, in 2 mm increments, which correspond to implant geometry. The Quick Release T-Handle is an accessory designed for use with the PLIF Trial Spacer. The PLIF Trial Spacer distracts on one side while the PLIF Spacer is inserted on the contralateral side.

Once the site has been prepared for device insertion the PLIF Distractor blades are placed into the disc space lateral to the dura. The curve on the neck of the distractor should be oriented toward the midline. The distractor blades are inserted completely into the disc space so that the ridges at the end of the blades rest on the vertebral body. Fluoroscopy can assist in confirming that the distractor blades are parallel to the endplates. Correct placement will angle the handles of the distractor cranially, particularly at L5-S1. An appropriately sized PLIF Trial Spacer is connected to the Quick Release T-Handle and inserted into the contralateral disc space with gentle impaction. Fluoroscopy and tactile judgment can assist in confirming the fit of the trial spacer. If the trial spacer is too loose or too tight, the next larger or smaller size is used until a secure fit is achieved. The implant is selected according to the correct trial spacer. The trial spacer can then be removed. The selected implant is held using the PLIF Implant Holder within the slots of the implant. The biological implant is introduced, in the correct orientation, into the contralateral disc space. Slight impaction is often necessary using the PLIF Impactor. The implant holder is removed once the desired position is achieved. Autogenous cancellous bone or a bone substitute is also placed in the anterior and medial aspect of the vertebral disc space prior to placement of the second implant. It is desired to recess the implants 2-4 mm beyond the posterior rim of the vertebral body.

For surgical technique utilizing the PLIF Trial Spacer, it is necessary to begin with the trial spacer determined during preoperative planning. The trial spacer is inserted with the contoured sides facing inferior-superior into the disc space. The trial spacer may also be inserted horizontally and turned vertically to size and distract the disc space. Slight impaction may be necessary. Fluoroscopy and tactile judgment can assist in confirming the fit of the trial spacer. If the trial spacer is too loose or too tight, the next larger or smaller size is used until a secure fit is achieved. The implant corresponding to the correct trial spacer is chosen. The implant is then introduced, in the correct orientation, into the contralateral disc space. Slight impaction may be necessary. The trial spacer is removed and the second implant, of the same height, is inserted into the space using gentle impaction. It is suggested to recess the implant 2-4 mm beyond the posterior rim of the vertebral body. Additional posterior instrumentation can be performed to enhance the fusion rate and decrease the risk of anterior column allograft migration.

The FRA Spacer Instruments are designed for use with this "biological cage" for a straight anterior or anterolateral approach. The preoperative planner is designed as an aid in determining the anterior height, posterior height, depth and lordosis. This is performed by comparing the lateral view on the radiographic planner with the adjacent intervertebral discs on a lateral radiograph. The implant should be firmly seated with a tight fit between the end-plates where the segment is fully distracted.

The midline of the intervertebral disc is exposed and the disc is evacuated with removal of the superficial layers of the cartilaginous end-plates to expose bleeding bone. Adequate preparation of the endplates is essential to facilitate vascular supply to the biological cage. Distraction is performed for the segment to restore disc height, open the neural foramen, and stabilize the biological cage. The distractor blades are inserted into the disc space. Once the desired distraction is achieved the implant size is determined utilizing a series of trial spacers. The implant corresponding to the correct trial spacer is then prepared. The biological cage is packed with bone graft material and inserted in an anterior posterior direction with contact of the adjacent end-plates and restoration of lordosis.

For anterolateral insertion, the center of the implant and the distractor will sit 30° offset from the anterior vertebral midline. This approach is commonly used at the L2-L5 vertebral segments. The anterior longitudinal ligament need not be resected during the anterolateral approach. The disc is evacuated and the end-plates prepared similar to the direct anterior approach. The trial size and biological cage are inserted at a 30° offset from the direct anterior approach which requires less soft tissue dissection and less mobilization of the vascular midline structures. It is recommended that additional bone graft material be inserted into the hole of the biological implant and circumferentially in contact with the end-plates.

One hundred and twenty three biological cages were utilized for anterior reconstruction in 90 patients from March 1998-July 1999. 48 patients were male and 42 female with an average age of 43 (19-72). The most common preoperative diagnosis included internal disc disruption with disc resorbtive syndrome (51 patients), instability/spondylolisthesis (28 patients), recurrent disc herniation with instability (12 patients), degenerative scoliosis (7 patients), and vertebral osteomyletis (2 patients). The majority of patients' (59) received 1 biological FRA Spacer while 29 patients were managed with 2-level biological cages, and only 2 patients received 3-level implants. The majority of patient's (35) were managed with additional posterior segmental pedicular screw fixation. Anterior "stand alone" biological cages were utilized in 30 patients and additional posterior translaminar screw fixation was utilized in 25 patients. This is an early clinical experience of utilizing this biological implant for anterior column reconstruction. The longest follow-up in this series of patients is 17 months with an average follow-up of 8 months. Up to this time, there has been no evidence of graft migration, infection or subsidence. Two patients that were managed solely with an anterior approach have required additional posterior surgery for suspected pseudoarthrosis. Only one patient that had been managed with an anterior column reconstruction and posterior translaminar screw fixation required additional surgery. None of the 35 patients that were treated with additional posterior segmental instrumentation required further surgery. Fracture of the FRA Spacer was noted, upon insertion, in 3 patients that required removal of the fractured biological cage and replacement at the time of the initial surgical procedure.

The PLIF Spacer has been utilized for approximately 6 months (beginning January 1999). 10 patients received implantation of this biological cage. Twenty-four implants were utilized in 3 males and 7 females. All patients were treated with additional posterior segmental instrumentation to include either translaminar screw fixation (3 patients) or posterior segmental pedicular screw fixation (7 patients). The indications for surgical implantation of these 10 patients included recurrent disc herniation (5 patients), spondylolisthesis without foraminal stenosis and instability (5 patients). Early clinical experience with this device is promising without evidence of migration, dislodgment, infection, pseudoarthrosis or iatrogenic instability.

The FRA Spacer is a wedge shaped femoral ring designed for both direct anterior and anterolateral insertion. The insertion can be performed with simultaneous distraction. Migration is decreased with the pyramidal teeth on both surfaces. The PLIF Spacer is a contoured, wedge shaped allograft that can be inserted with a minimally invasive foraminotomy. The five sizes permit preservation of the facets and minimal nerve root retraction. The design allows distraction and insertion with the saw-tooth pattern surface.

The FRA and PLIF biological cages have been designed along with a set of instruments that allow the surgeon to perform these surgeries with a minimally invasive approach. Both of these implants (for both an anterior and posterior approach) facilitate the preservation of the vertebral end-plates and allow anatomical restoration of the sagittal alignment to provide the best "biologic" environment to obtain a stable intervertebral segment and a subsequent arthrodesis. The PLIF Spacer and FRA Spacer are designed by and available through Synthes-Stratec Spine. FIG. 16 shows additional prior art devices for intervertebral fusion familiar to those familiar with the art.

Figure 17:
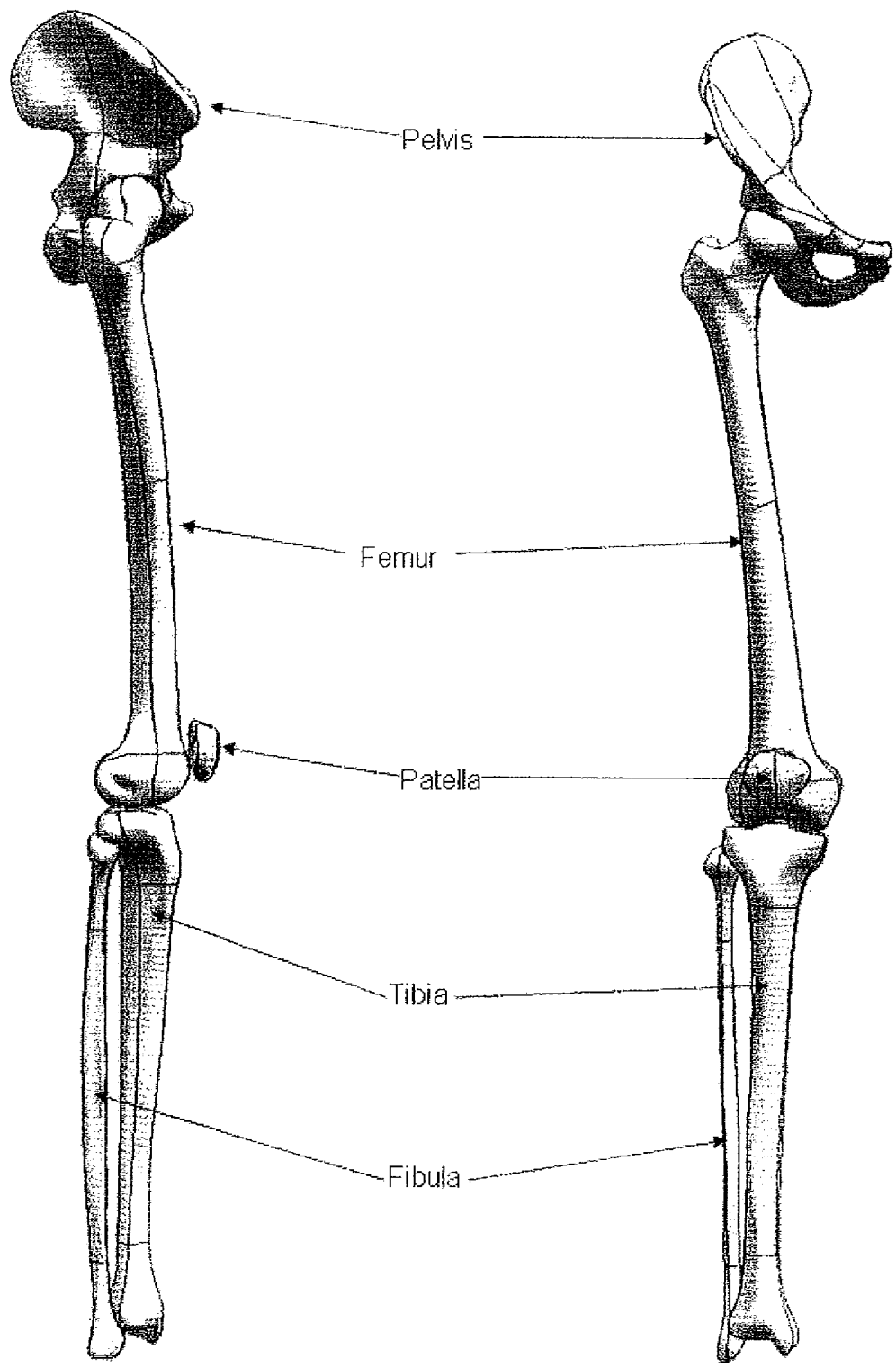
Figure 18:
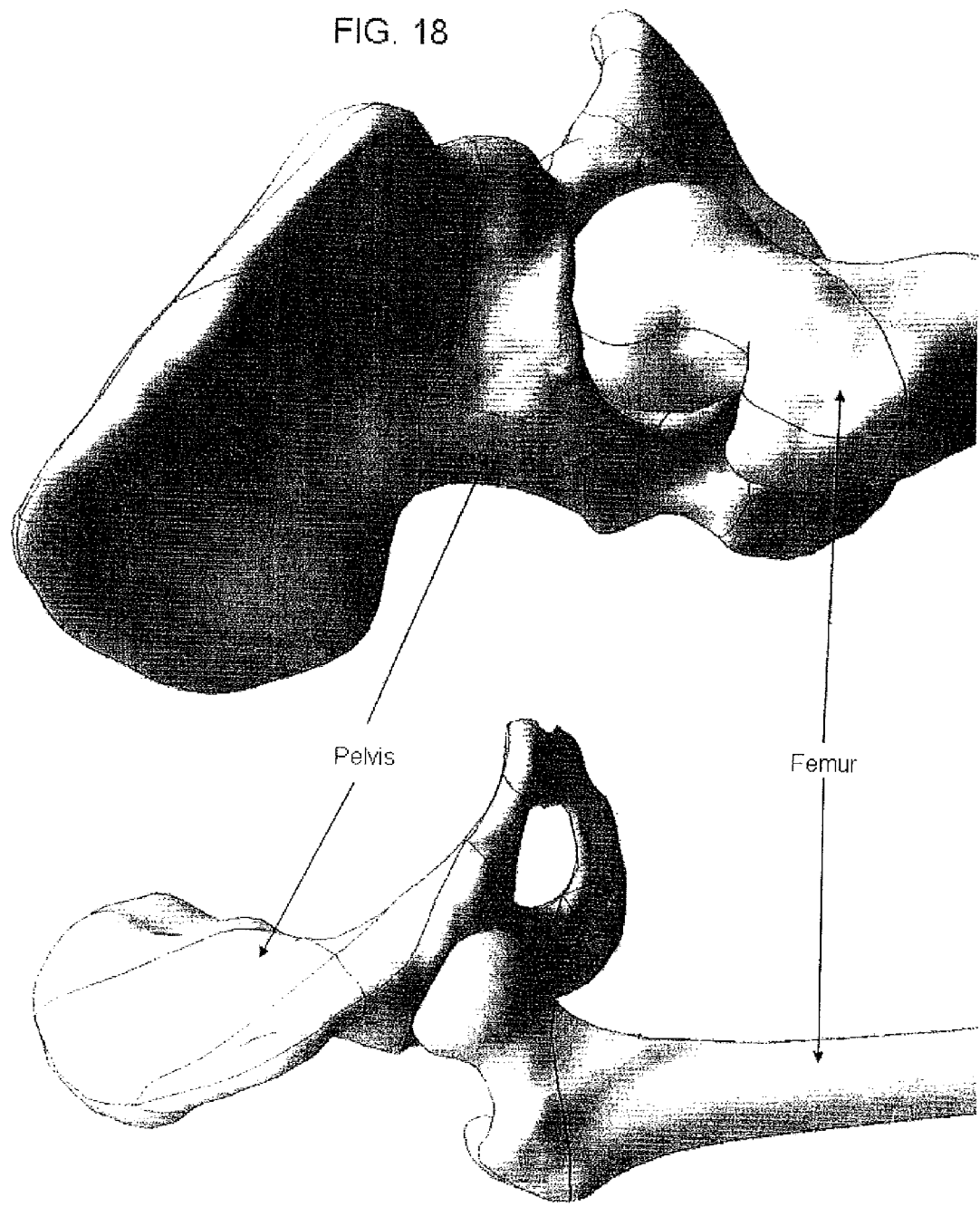
Figure 19:
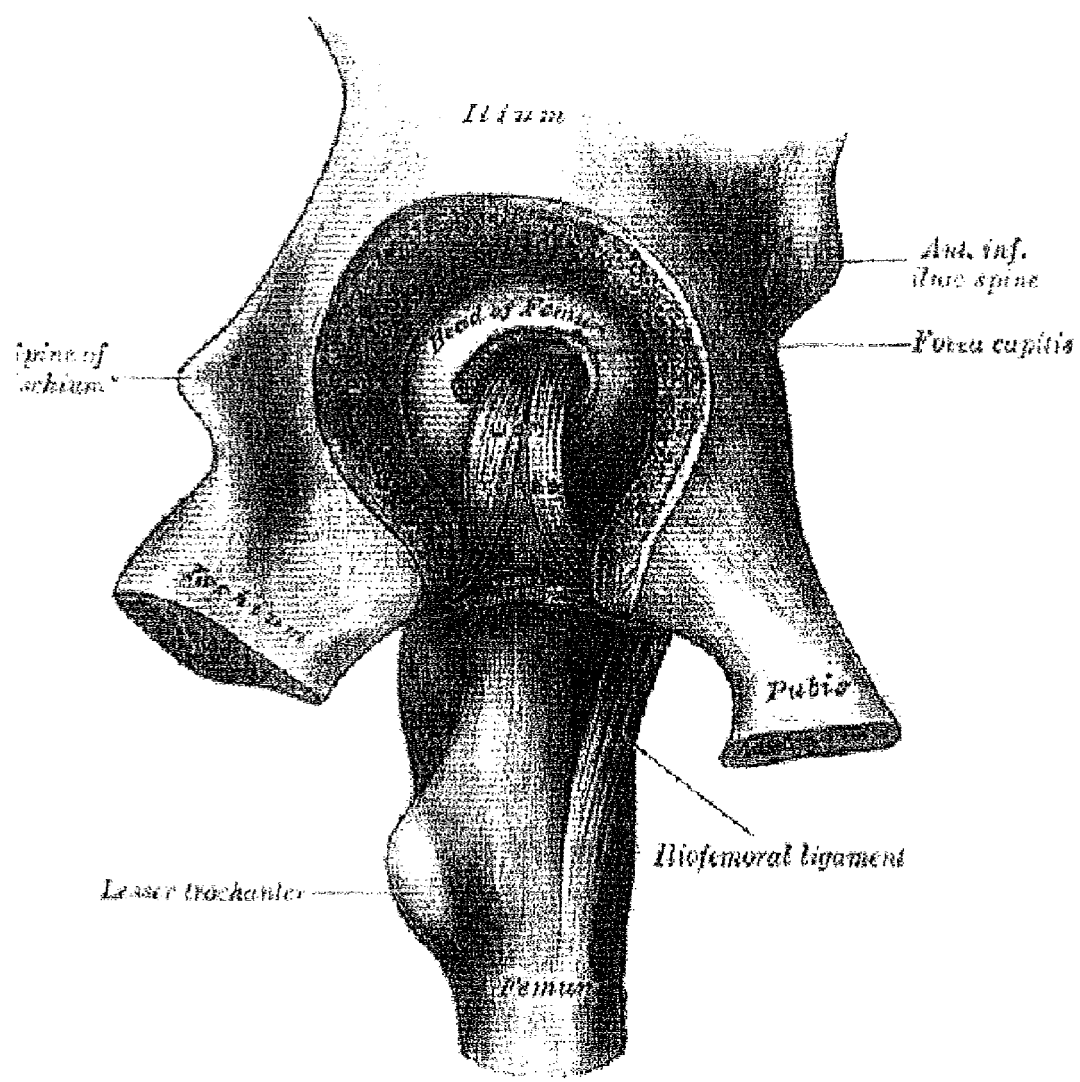
Figure 47:
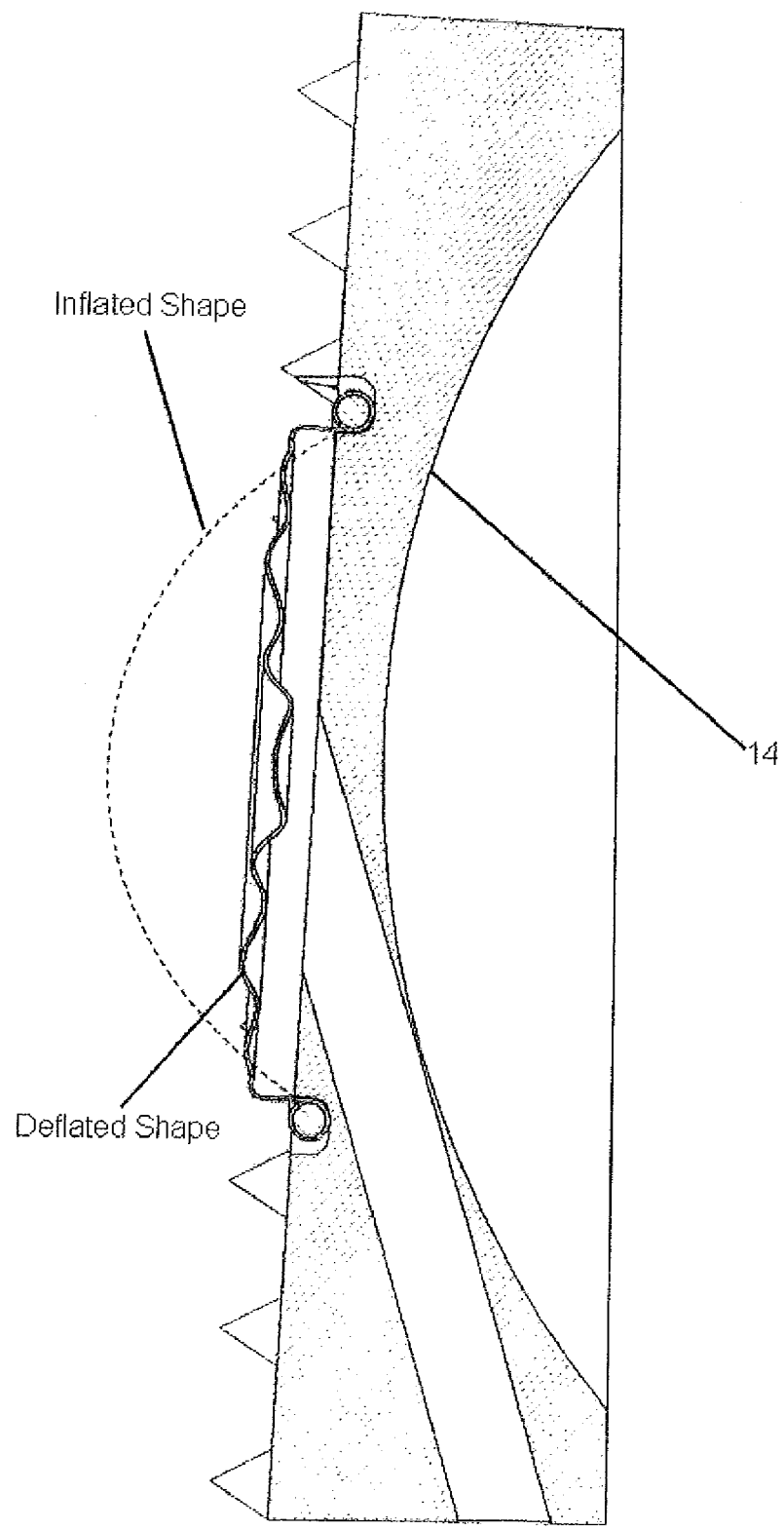

Various embodiments of the present invention will now be described. FIGS. 17, 18, and 19 show various depictions of the human hip joint. FIG. 19 is a view of the human hip joint obtained by opening the floor of the acetabulum from within the pelvis revealing the cartilage bearing surfaces of the femoral head, the teres ligament (labeled LIGT TERES), and other anatomic structures of the pelvis and hip joint. The thickness of cartilage on the femoral head is known to range between 3 mm to 6 mm and the thickness of cartilage on the acetabulum is also known to range generally between 3 mm to 6 mm. The human hip joint exhibits fascinating micro- and macro-scopic behavior, the recognition of which inspired the embodiments of the present invention. First, the hip joint articulates polyaxially (3 degrees of rotational freedom about 3 mutually perpendicular axes) while simultaneously allowing, in a constrained and shock-absorbing manner, translation along the same 3 mutually perpendicular axes due to the viscoelastic properties of the cartilage integrally formed between adjacent bone surfaces. Furthermore, the cartilaginous material possesses profound shock absorbing capabilities as is well understood in the scientific literature regarding the kinematics and physiological performance of human joints. Furthermore, the bone material underlying the respective cartilage surfaces of the adjacent joints is an extraordinarily complex composite structure "biologically optimized" to handle the physiological loading of the joint with minimal degradation of performance over time in the absence of mechanical or physiological disease processes to the contrary. Simply put, the hip joint, or other articular joints of the human body, may provide the basic "pre-production materials" for a far more "optimized disc replacement design" than mankind is capable of generating by commercial or artificial means. The use of the hip joint as the basis of the majority of the figures herein is illustrative only. As noted in regard to FIGS. 47 and 48, any cartilage and/or disc bearing joint in the human body (including the spine itself) serving as the basis for an allograft dynamic disc replacement product is within the scope of the embodiments of the present invention.

Figure 20:
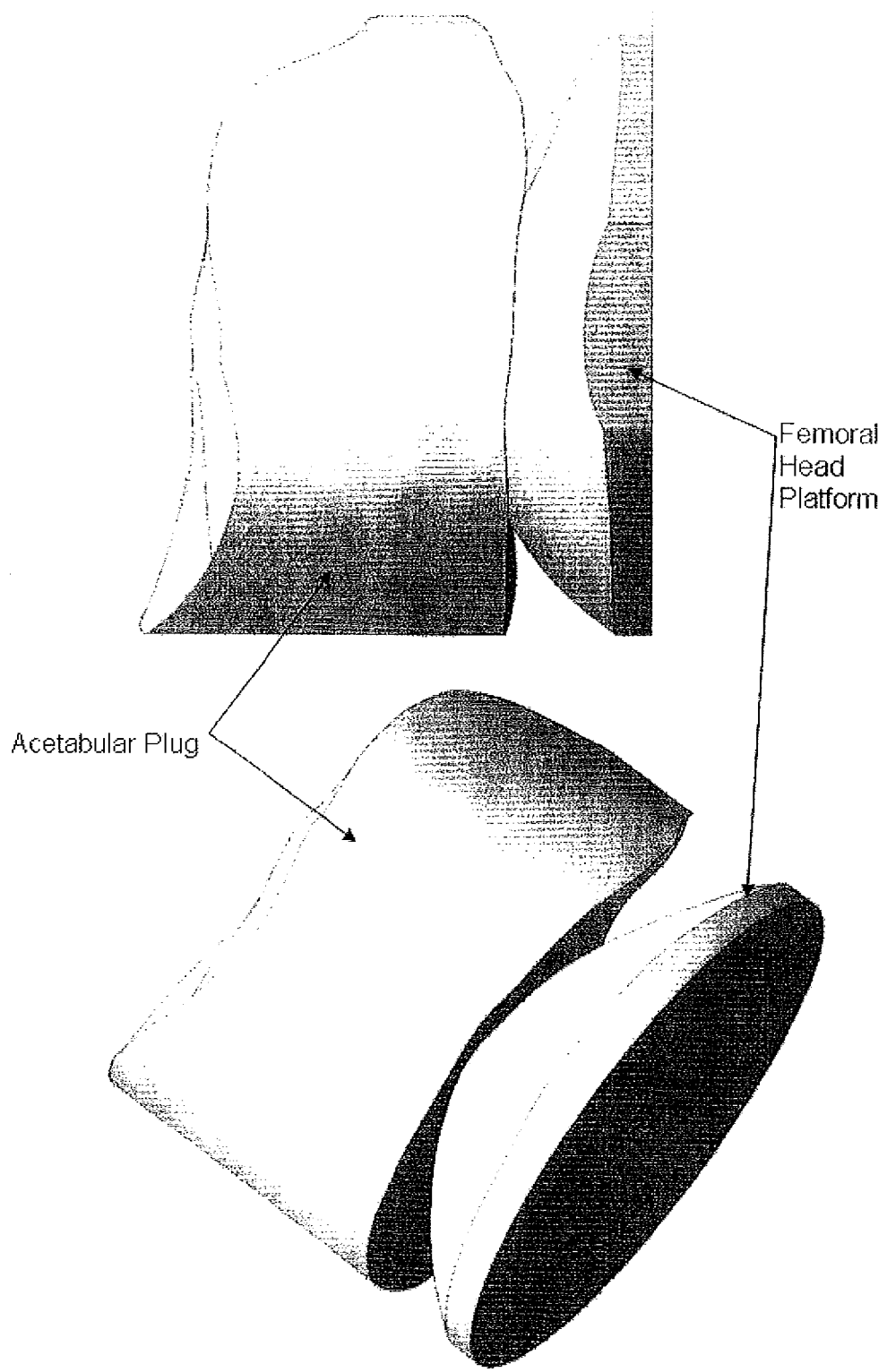
Figure 21:
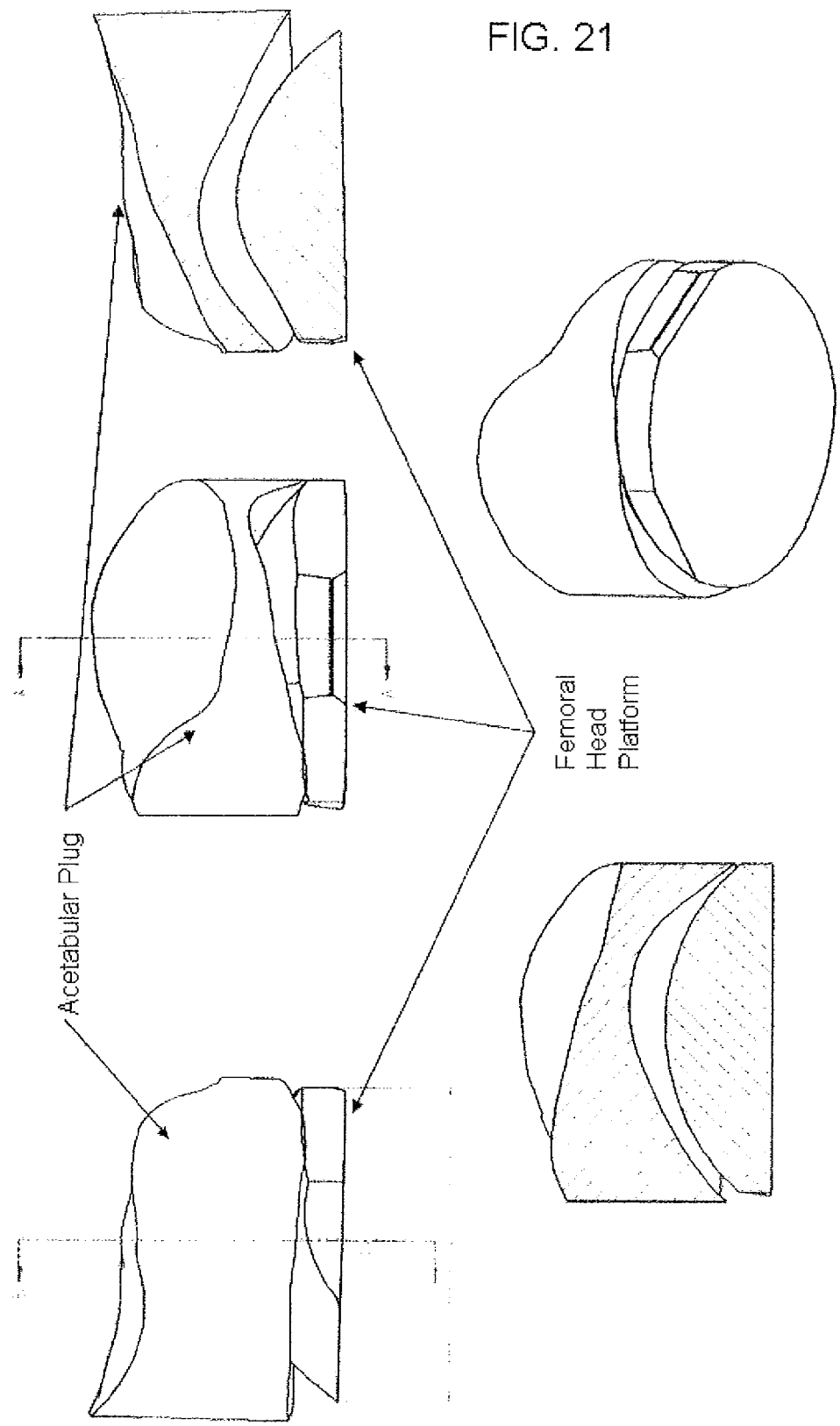

FIGS. 20 and 21 shows a generally cylindrical section taken from both the femoral head and acetabulum (and/or pelvis) to form an acetabular plug, and femoral head platform as noted in FIGS. 20 and 21. This section may be obtained by machining tools such as chisels, saws, punches, WirePlasty, PinPlasty, Profile Based Resection, Ultrasonic Cutters, and/or coring saws (similar to the "hollow drills" used to cut cylindrical holes in a door to accept a door knob). It should be noted that the naturally occurring cartilage found between these bones is preserved in their generally natural states to facilitate the articular and physiological processes upon which the embodiments of the present invention rely. Furthermore, the teres ligament (not shown in figures subsequent to FIG. 19 for the sake of clarity), and/or its attachments to the acetabulum and/or femur may be preserved (and/or separated and subsequently re-fixed or re-attached to bone) to serve as a constraint feature of the embodiments of the present invention to mitigate or eliminate the potential for dislocation and/or excessive translation and/or rotation of the embodiments of the present invention in a manner somewhat similar to the function of the teres ligament in the human hip which limits adduction and/or rotational degrees of freedom potentially harmful to the human body. The provision of a constraint feature may be understood by laymen to be analogous to an RPM, torque, speed, or power limiter as is known in the engine industry—i.e.; going fast or accelerating quickly are good performance characteristics, but if the car/dynamic disc explodes or flips over or has pistons shooting through the hood, it is fair to consider the event a "very bad thing".

Figure 22:
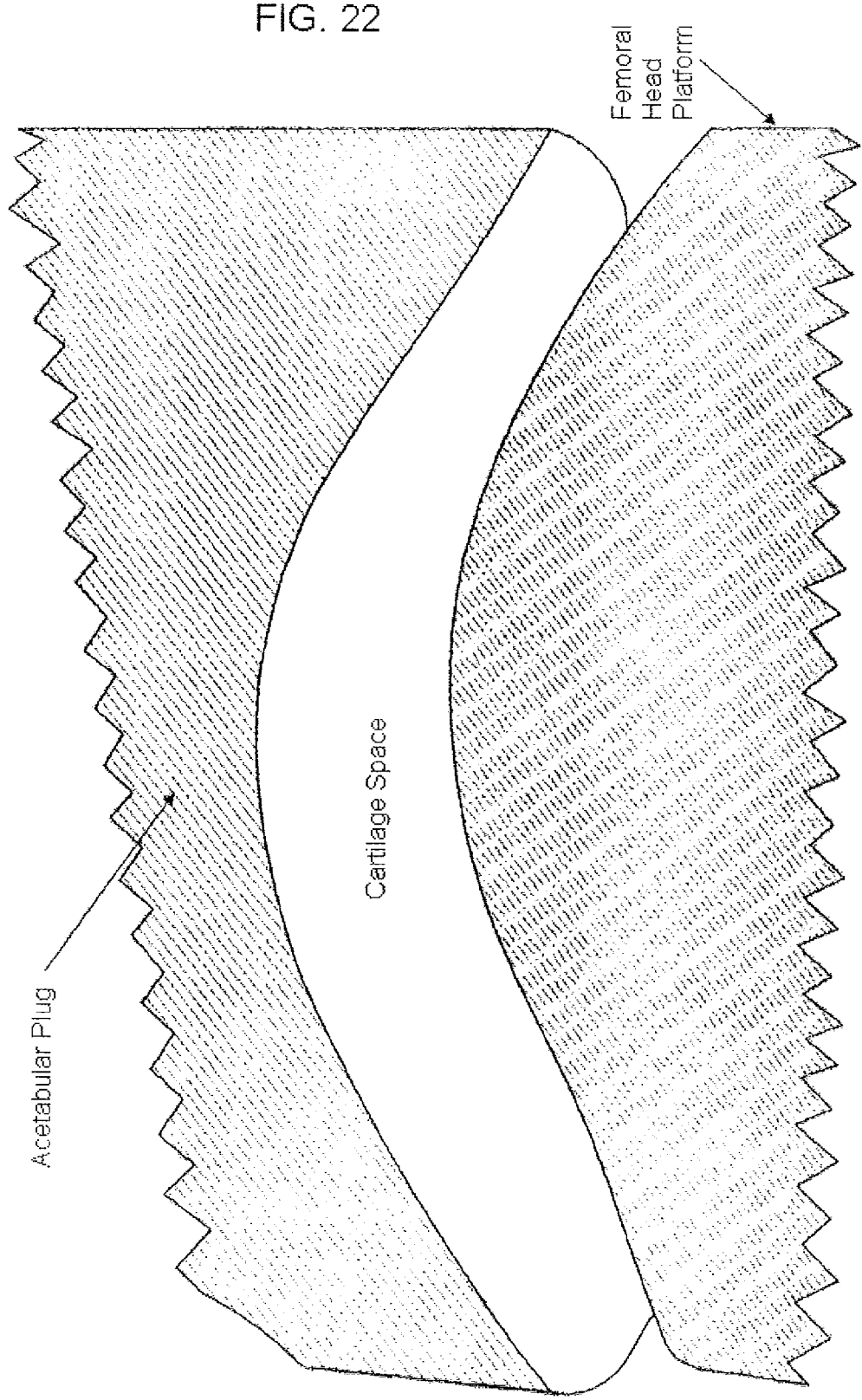
Figure 23:
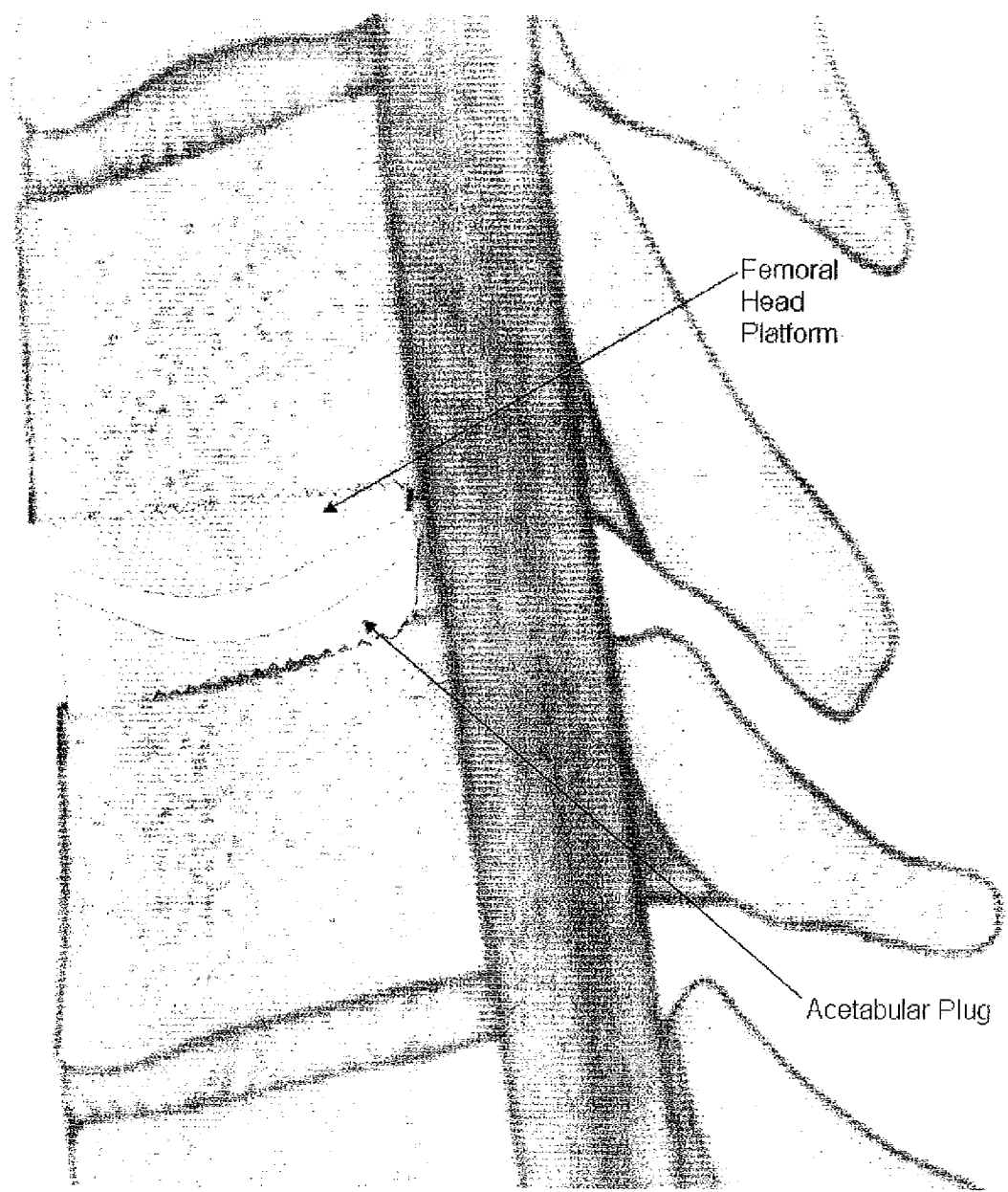

Having obtained the articular sections from a human of xenograft donor and/or synthetically derived source, the sections will then generally be delivered to a tissue processing facility, such as Musculoskeletal Transplant Foundation, where additional machining, osteobiologic, disease testing, thermal, and packaging processes will be performed to ensure the performance of the dynamic disc and/or facet arthroplasty devices. FIG. 22 shows a simplistic cross-sectional drawing of an embodiment of the present invention wherein the articular cartilage of the donor hip is not shown, but rather the location for which is generally indicated by the label 'cartilage space', for the sake of clarity. The generally serrated, or 'saw tooth' profile surfaces shown on the acetabular plug and femoral head platform are machined features implemented in this and other embodiments of the present invention to minimized micromotion, motion, and/or migration of the implant surfaces to facilitate short and long term fixation and/or incorporation of the device with and/or to the living patient bone tissue. FIG. 23 shows this embodiment of the present invention having been surgically implanted between the resected endplate surfaces of adjacent vertebral bodies in manner similar to the FRA apparatus and methods described above (FIGS. 6 through 16 in general, FIGS. 6, 9, 10 and 12 in particular). One of ordinary skill in the art will recognize the anatomic features of the spine and their relative locations with respect to the device of this embodiment of the present invention.

Augmented Implant Fixation Embodiments—In most patients requiring intervertebral surgical intervention, the simplistic embodiment of the present invention shown in FIGS. 22 & 23 will perform excellently while relying on existing surgical techniques and surgical instrumentation to implant the dynamic spinal implant of the present invention. However, there are many pathologies that require more robust fixation and/or intervention to address the progress of the disease or the extent of the traumatic event leading to surgery. These include osteoporosis, crones disease, vertebral body compression fracture, and a host of other causes. To extend the range of indications for the dynamic spinal implant of the present invention, certain of the following alternate embodiments are eminently suitable.

Figure 24:
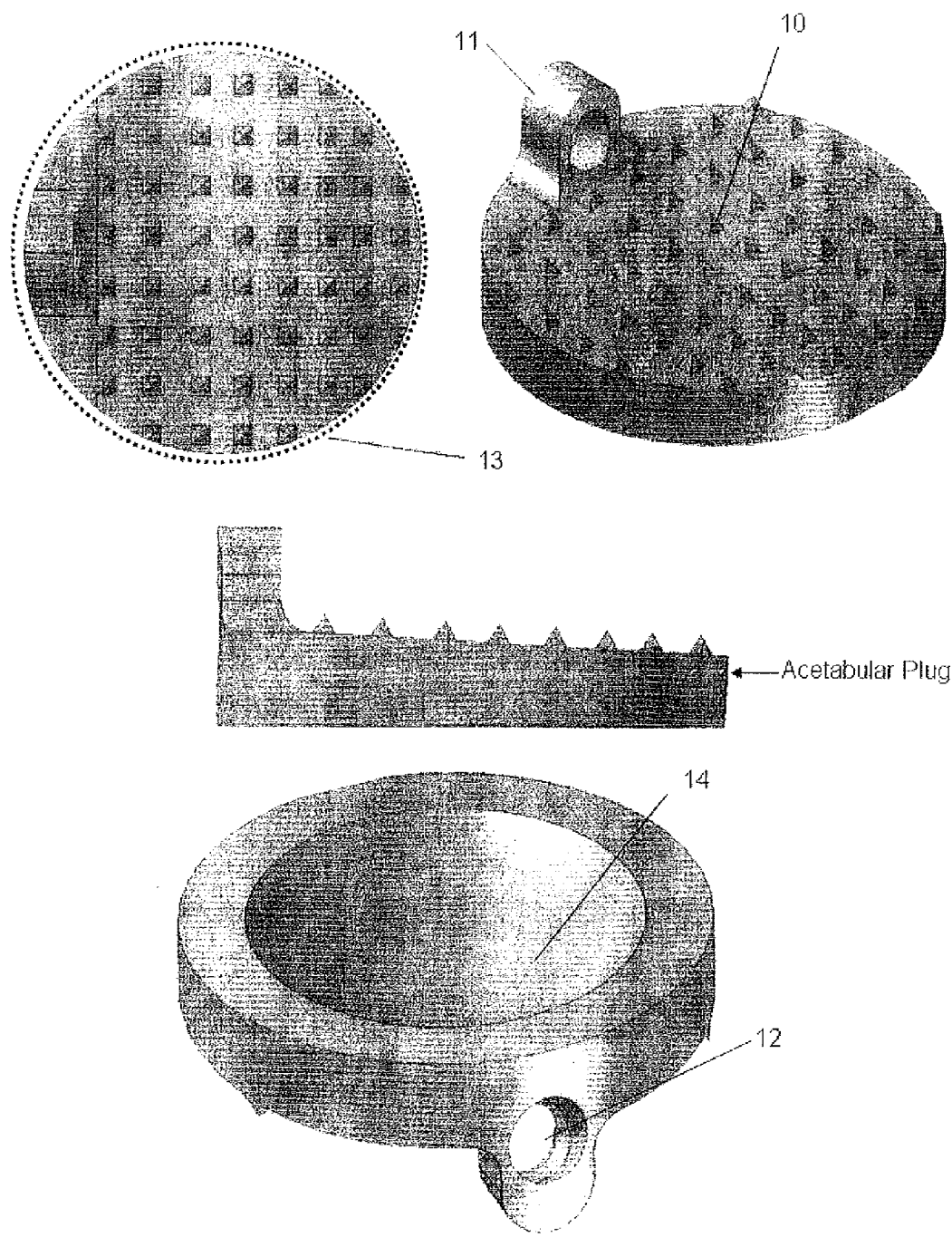

Another embodiment of the present invention is shown in FIGS. 24-26 and 34-40. This embodiment of the present invention includes keying feature 11 noted in FIGS. 24, 25, and 26 in an anterior only or posterior only embodiment generally which may be seated against the anterior cortex of the vertebral body or within an aperture or opening formed in the anterior cortex of the anterior corpus of the vertebral body. This keying feature allows for the inclusion and additional fixation by secondary fixation element 40 shown in FIGS. 29 through 34, which may be generally described as a bone screw, or in another embodiment, a cannulated, fenestrated cortical allograft bone screw, which will be further described later herein. Other features of this embodiment of the present invention include textured surface 10, footprint 13, cartilage bearing bone surface 14, and secondary fixation element 12 (also described herein as bone screw aperture 12). Textured surface 10 in FIG. 24 is similar to the textured surface 10P on Synthes Femoral Ring Allograft ALIF device shown in FIGS. 11 and 12 for mitigation of migration, subsidence, expulsion, and/or micromotion. Cartilage bearing bone surface 14 is the naturally occurring bone surface supporting cartilage 15 as shown in FIG. 26. It should be noted that the transition from bone to cartilage is not nearly as 'cleanly' defined as the demarcation between the two would lead one to believe. In fact, the transition is highly variegated and microscopically gradual. Histologists wrestle to define the exact description of these transitional tissues, a discussion which is best left beyond the scope of this patent application for sake of brevity.

Embodiments of the present invention including keying features or abutment features which contact the anterior, or anterolateral faces of the corpus and extend anteriorly or anterolaterally therefrom are eminently feasible, as demonstrated by the clinical performance of both the Bristol and Bryan devices shown in FIGS. 4, 9, 10 and FIGS. 5-8, respectively, which rely at least partially on such features for fixation to living bone. It is strongly recommended that intervertebral, and in fact any spinal implant whether it be anterior column or posterior column based, be essentially "foot print neutral" to avoid the potential irritation or damage to soft tissues surrounding and supporting the physiological functions of tissues surrounding the spinal column. The term "foot print" is used herein to describe the profile of the implants of the present invention with respect to the geometry or profile of the periphery of the endplates of the cervical, thoracic, lumbar, and/or sacral vertebra (as viewed from a generally superior to a generally inferior direction, or more generally from a generally upper to a generally lower direction or a generally lower to an generally upper direction) as generally indicated by cylindrical foot print profile 13 shown in FIG. 24, or modified cylindrical foot print profile 23 or anatomic foot print profile 93 both of which are shown in FIG. 25.

One of the things of particular interest to note is that different vertebrae have different endplate profiles clearly calling for variations in the implant's foot print profile and one of ordinary skill in the art will easily recognize viable variations to the foot print profile(s) shown herein and all such variations thereof and their impact on implant geometry. All such variations are to be considered within the scope of the present invention. It will be apparent that rubbing up against the aorta is rarely a good thing no matter how smoothly finished an implant may be. Preferably, the implant of the present invention is positioned entirely within the endplate space and is therefore generally less likely to bring the device into damaging contact with blood vessels or nervous structures than a device which is already in contact with them before a catastrophic event. In the spine, a couple of millimeters (mm) can quite literally mean the difference between life or death in a "fender bender", much less a high impact vehicular event, and providing an implant which buys the patient as much leeway and/or chance of survival as possible under extreme circumstances/the event of post-operative trauma is certainly an object to be pursued.

Figure 25:
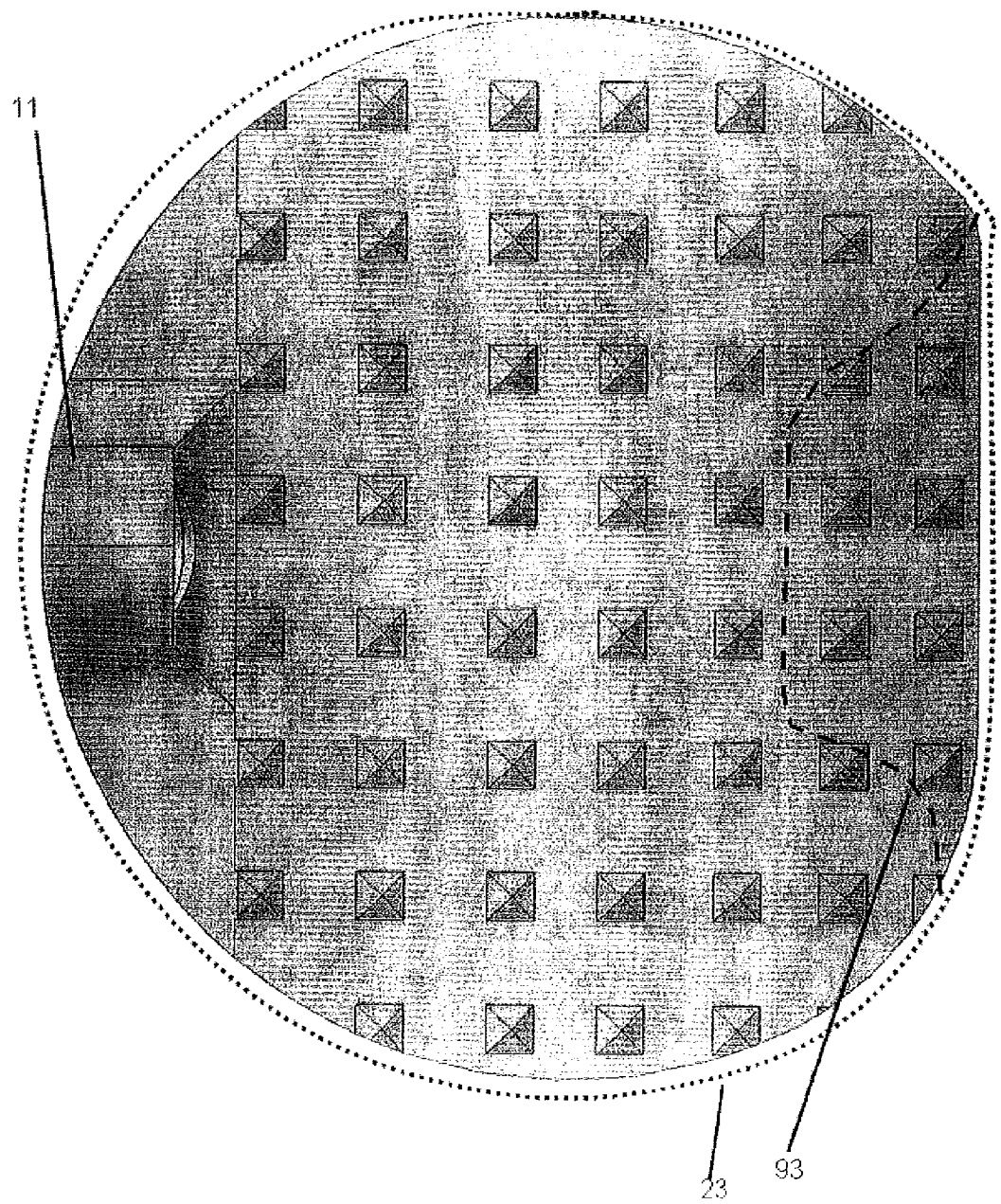

As shown in FIG. 24, the keying feature 11 noted in FIGS. 24-26 is preferably seated in a recess in the vertebral body prepared by an appropriate surgical cutting tool. Although the keying feature 11 could be used independently of secondary fixation elements or bone screws 40, the use of bone screw aperture 12 in FIGS. 24 and 26 enabling insertion of and mechanical fixation to bone screws 40 to both the implant and the vertebral body to affect robust fixation and stabilization of the resulting construct.

Figure 27:
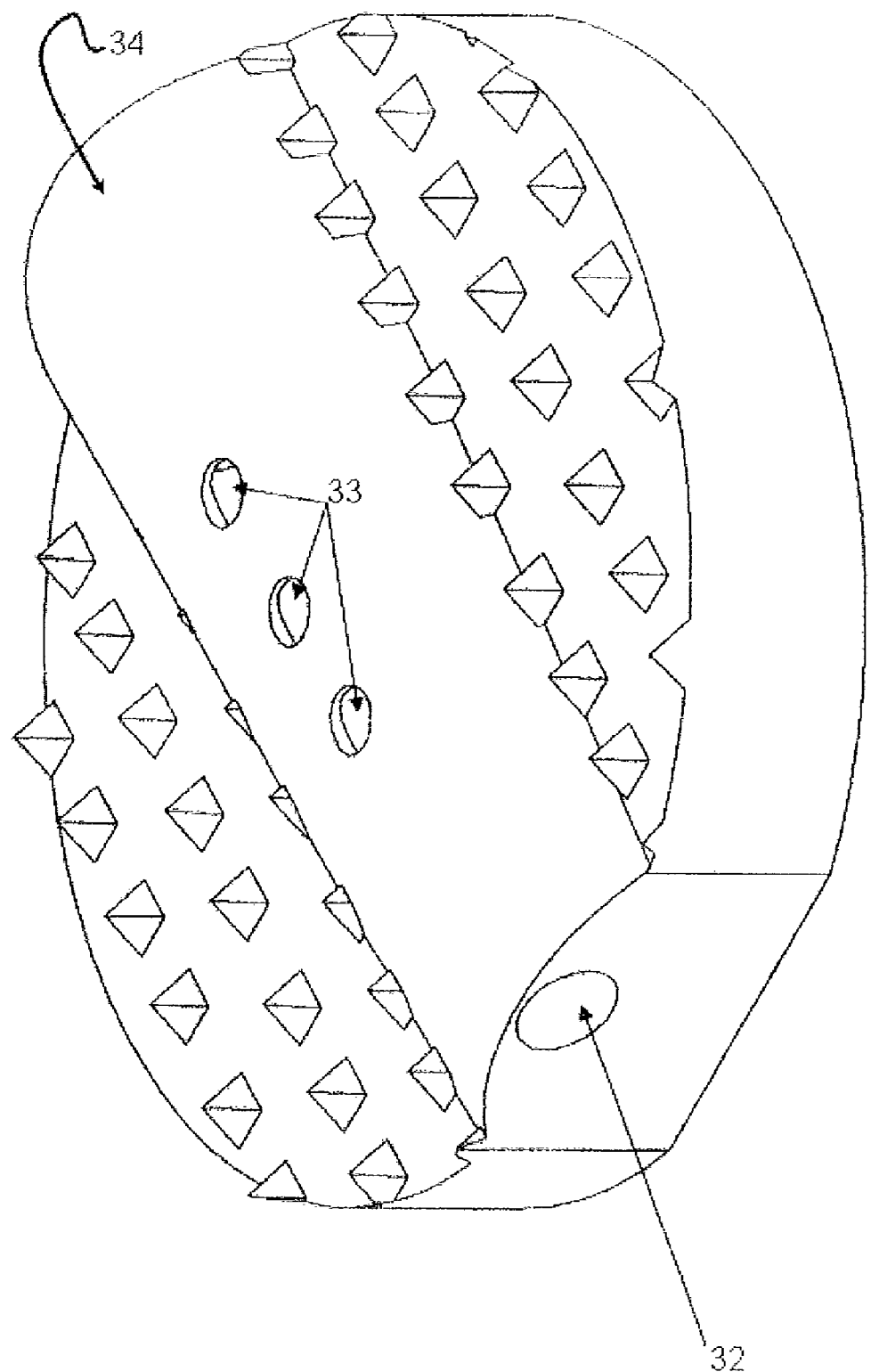

FIGS. 27 and 28 show an alternative embodiment of the present invention. This embodiment demonstrates certain principals of operation intended to facilitate improved interfacial load transfer characteristics by and/or between the device and patient bone tissue both intraoperatively and post-operatively during the healing and incorporation processes. This embodiment includes flowable injection aperture 32 with injection aperture end 36, flowable interdigitation aperture(s) 33, and/or keying feature 34. Keying feature 34 serves to facilitate mechanical interference between the bone/implant interface to prevent or mitigate subsidence, rotation, and/or migration of the implant with respect to the bone(s) to which it is attached. The curvilinear nature of the keying feature geometries shown facilitates beneficial physiological response to both implant geometry and interfacial loading conditions to, in essence, give the body every "reason" to be happy with respond quickly and favorably to the presence of the implant. The skeletal system (and in fact almost the entirety of the human body) reacts in profoundly different ways based upon the geometry of that which contacts it as well as the stiffness, elastic limit, chemical and/or biological composition, and porosity of the materials that contact it. For instance, Cobalt-Chrome and titanium materials are commonly consider "biocompatible", yet if they are formed into a shape sharp features similar to a splinter and implanted into the human body (skin, soft tissue, or bone) they would be rejected, isolated, and eventually ejected from the human body much in the way the a splinter of glass or aluminum will gradually be ejected.

In one embodiment, the flowable injection aperture 32 is intended to operably interconnect with a nozzle-like feature of a PMMA (commonly referred to as "bone cement") injection and/or mixing and/or delivery system device(s) (not shown). Other materials may be delivered through a feature of this kind including other flowable materials such as morselized graft bones osteobiologic slurry, ceramic materials, antibiotic compounds, PLA and/or PGA based composition, or combination of the aforementioned. As shown in FIG. 27 (and in a different embodiment, FIG. 48), the flowable material is injected into and at least partially within the implant by way of injection aperture 32 until it emerges from flowable interdigitation aperture(s) 33 and into contact with patient bone. Subsequent injection of additional flowable material will cause the flowable material to both contact and penetrate the porous surfaces of the patient bone and/or allograft device in a reproducible manner to achieve mechanical interdigitation of the resultant implant/flowable material/patient bone construct.

This injection technique provides for excellent interdigitation between flowable material, implant devices, and patient bone tissue, and in the case of dynamic disc replacement, it will be beneficial to limit and/or control the amount of flowable material introduced in this fashion to avoid excessive extravasation of the flowable material. Especially in the case of materials that harden or which will negatively impact the ability of the implant/flowable material/patient bone construct to incorporate with living patient tissue (such as acting as a profound barrier to angiogenesis or blood vessel formation across the bone-implant interface), it is important that the injection of flowable material be controlled. In the case of bone cement, or slurries including PMMA, the thermal, mechanical, and/or chemical processes of curing, and/or the mechanical and/or clinical consequences of extravasation of curable compounds can be clinically catastrophic. If fingers of cured bone cement encapsulating a section of or contact a surface of, for instance, the spinal cord, for example, and the vertebrae adjacent the implant of the present invention moving through their respective ranges of motion, thus causing the fingers to harm the anatomic feature. One of ordinary skill in the art will recognize uncontrolled extravasation of flowable material from flowable interdigitation apertures 33 as a potentially catastrophic clinical event to be avoided. Furthermore, injection of flowable material into or adjacent the cartilage space may profoundly impact the durability of the present invention in a manner similar to "third body wear" as it is commonly referred to in the field of long bone joint replacement (TKA, THA, TAA, Shoulder Arthroplasty, etc. . . . ).

Simply put, failing to control the volume, pressure, flow rate, and/or viscosity of the flowable material introduced into 32 may result in events analogous to throwing a big old handful of sand into your car's oil pan while driving at top speed—not a good thing.

Another event to avoid by way of controlled extravasion is, in one embodiment of the present invention, the complete isolation of the graft material of the present invention from vascularization by patient tissue thus inhibiting or preventing what is commonly referred to as 'graft incorporation', or, perhaps less commonly as 'creeping substitution'. Graft incorporation and creeping substitution both refer to what could be loosely described as gradual colonization of graft material by living patient tissue. As patient cells begin to fill the porous surfaces of the graft material, they also make those graft materials, especially the inorganic structures comprised of such materials as hydroxyapatite, tricalcium phosphate, collogen, and others available to the patient's body as 'raw material' for absorbtion by the body and subsequent 'rebuilding' of new bone whose physical and physiological structures are specifically dictated by the response of the patient's body to the presence of the implant and the patient's physical environment and activities in general. It should be noted that a chisel, or any other cutting tool referred to herein, could be used to create complementary resected endplate and/or anterior column bone resected surfaces to the implant geometries of the embodiments of the present invention, such as a simple modification to the chisel or "punch" based instrumentation of the Synthes FRA based product described herein. Indicated by 36 in FIG. 28, the injection aperture 32 may terminate in the surface 36, or may be angled or curved to emerge from keying feature 34 as a feature analogous to feature 33.

It should be noted that in this embodiment it is important that material injected into 32 not invade or penetrate, or traverse the cartilage bearing surface 34 for fear of harming the articular surfaces optimally provided by leaving the cartilage in its generally natural form. It is within the scope of the present invention to provide an alternate embodiment which is introduced through a generally anterior approach, yet feature 32 is located posteriorly or posteriolaterally for injection of material through a posterior or posteriolateral incision through which a facet arthroplasty device is implanted. Further, a balloon or mesh may be provided in conjunction with the embodiments of the present invention, similar to that indicated in FIGS. 41-48, which limits flowable extravasion for purposes of either facilitating implant fixation or restoring vertebral body height and mechanical integrity in a manner recognizable as similar to Kyphoplasty techniques currently available (this could be highly beneficial as corpus or vertebral body collapse due to degenerative or traumatic causes is often associated with disc compromise calling for dynamic disc replacement). The embodiment of the present invention shown in FIGS. 41-48 will be discussed in greater detail later in this specification.

Yet another embodiment of the present invention implements secondary fixation element 40 (also described herein as bone screw 40) shown in FIGS. 29 through 40. Bone screws have been used in the prior art extensively, but certain features of the bone screw 40 of the present invention provide additional and unanticipated clinical benefit. First, many screw designs have been proposed to affect preload between or across fracture and/or bone/implant interfaces, but few have been proven to be clinically successful as living bone tissue is subject to a phenomenon sometimes referred to as viscoelastic stress relaxation. This term describes an incredibly complex chain of mechanically impacted physiological events that, although partially quantified in the literature, is not truly and emphatically embraced in the realm of orthopedics. For more detailed exploration of this phenomenon, reference is made to U.S. Pat. No. 4,959,064 by John Engelhardt, and an article in the literature entitled "Size Effects in the Elasticity and Viscoelasticity of Bone" (Biomechan Model Mechanobiol 1 (2003) 295-301 © Springer-Verlag 2003, both of which are included herein in their entirety by reference. Simply put, if bone is subject to stress exceeding a poorly understood limit, sometimes referred to as the viscoelastic limit, bone will resorb away from that which is transmitting that stress to the bone causing "relaxation" of the loads which induced the stress. On the other hand, preloading implants into contact with bone surfaces to facilitate ingrowth or incorporation is a commonly pursued goal, as is preloading of fractured bone surfaces in efforts to fix fractures with screws oriented generally, even vaguely, across said fracture. For the most part these efforts fail to optimally maintain the desired preload for more than a few days postoperatively as the desired preload combined with the bone/implant interfacial geometries or bone/bone screw interfacial geometries induced stresses in excess of those tolerated by bone. Knowing that stress is a function of among other things, force and surface area, it is reasonable to expect that if the surface area about or across which preload is applied is significantly increased, that the preload will not be lost to viscoelastic relaxation. The embodiments of bone screws of the present invention cures this deficiency by enabling a tremendous increase in effective surface area per unit preload by way of providing interdigitation of flowable materials, such as pre-polymerized PMMA/bone cements, into, between, and/or about a bone screw or fixation element and surrounding porous living bone, or semi-porous living bone, or non-porous living bone, or allograft cancellous or cortical bone, than would otherwise be afforded by contact between a screw or other fixation element in the absence of flowable material based interdigitation. As indicated in FIGS. 29-40, the bone screws/fixation elements of this embodiment of the present invention includes several features, and alternative embodiments of those features.

Figure 29:
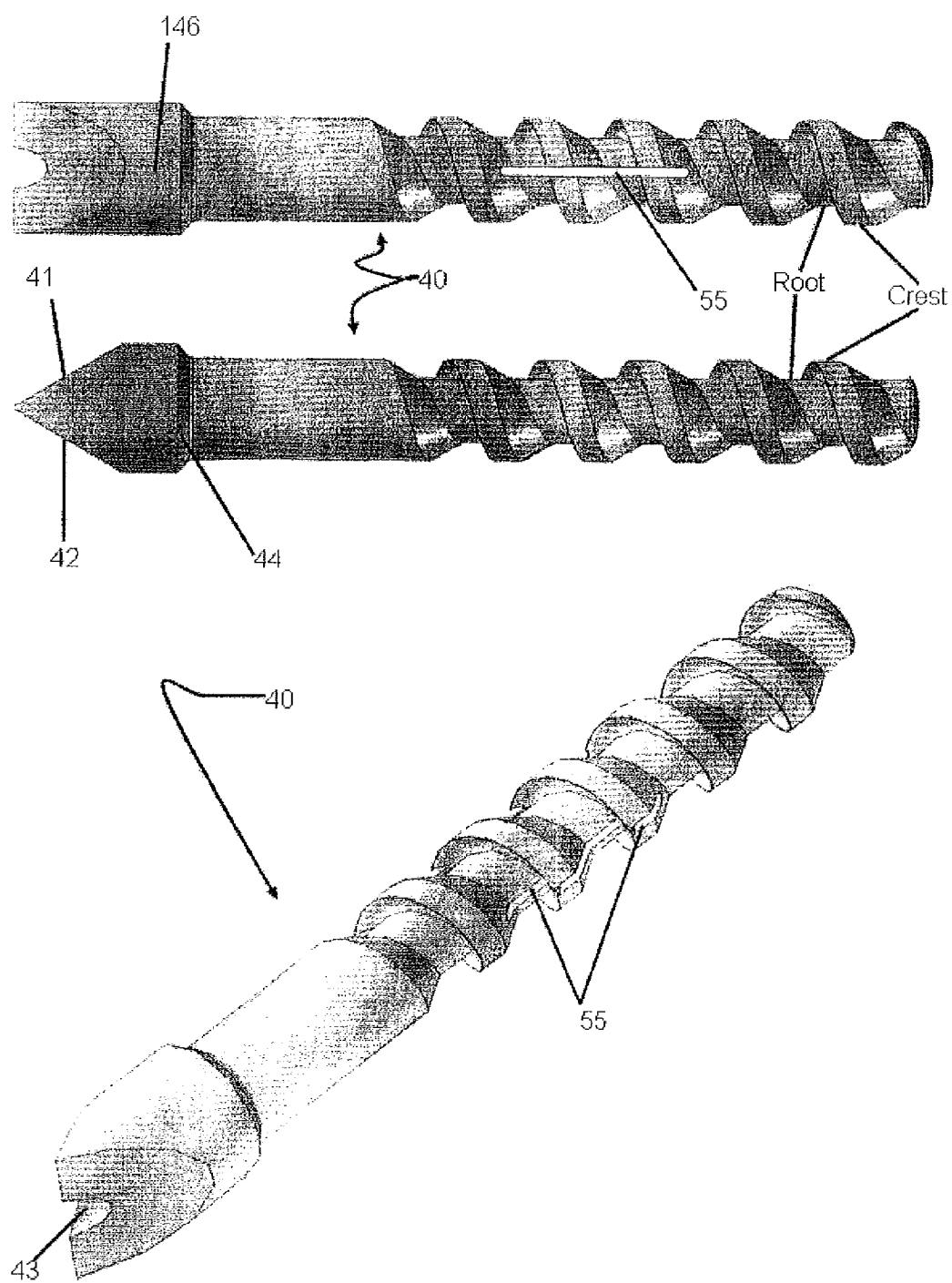

FIG. 29 shows an embodiment of the secondary fixation element 40 or bone screw 40 of the present invention. Bone screw 40 possesses driver mating feature defined by drive surfaces 41 and 42 (the driver mating feature herein, and many other features of the bone screw of the present invention, is/are described in U.S. Pat. Nos. 6,162,225, 6,099,529 and 6,506,192, by the inventor of the present invention, to a degree making it redundant to re-describe them herein, and so, for the sake of brevity in this specification, all of the contents of these patents are herein included by reference in their entirety, and features noted therein may without prejudice be interchanged with the features described herein), compression face feature 44 (for contact and/or mating with the implants of the present invention), flowable injection feature 43, flowable interdigitation aperture(s) 55 (feature 55 in FIG. 29 is in a slot-like in configuration and is interchangeable in most applications to flowable interdigitation aperture(s) 45 in FIG. 30 which are for lack of a more elegant term "cylinder-like" as shown in FIG. 32 in greater detail), and root and crest features directly indicated. FIG. 31 further shows the direction (generally indicated as 143) into which flowable materials may be injected into flowable injection aperture 43.

Figure 30:
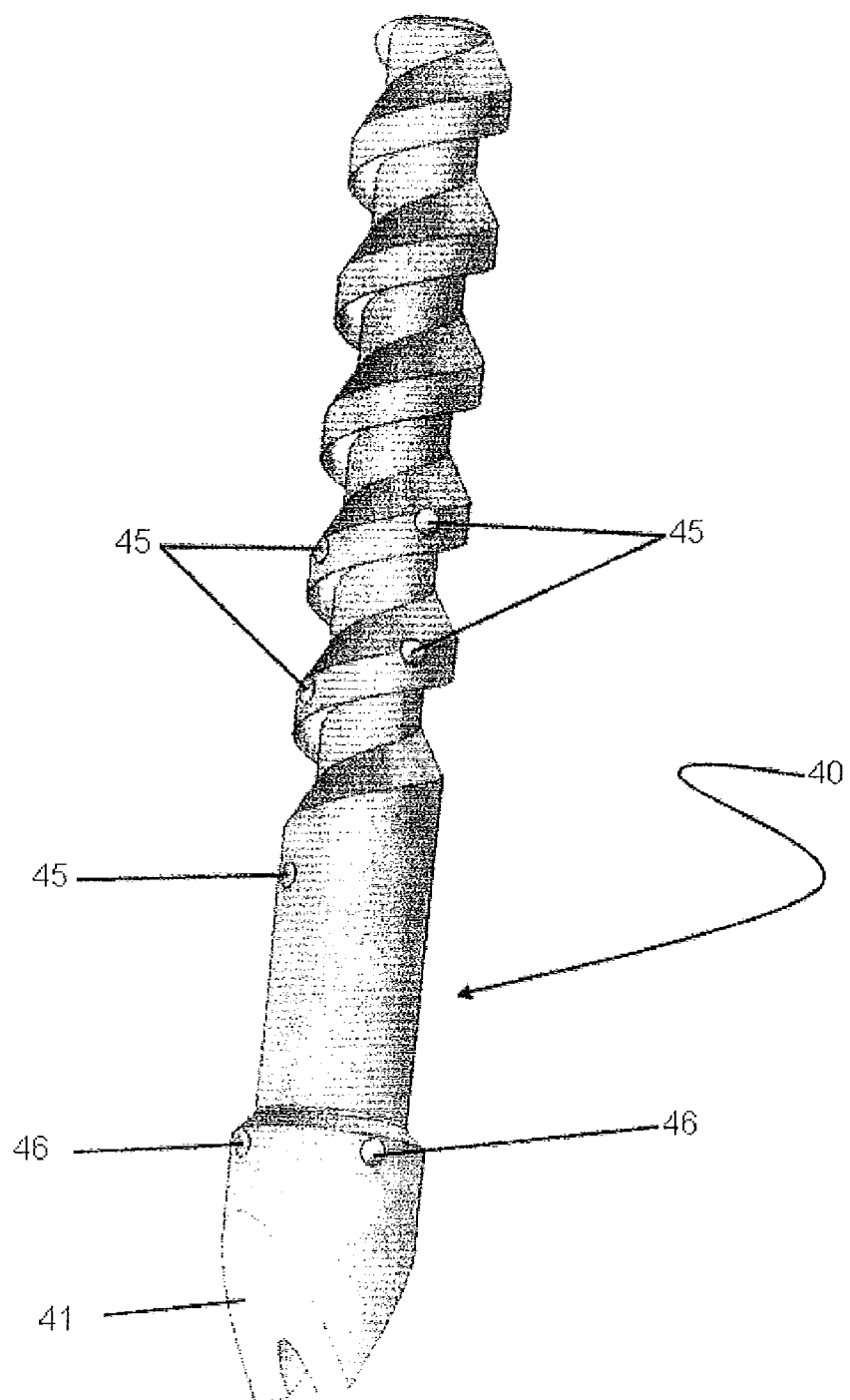
Figure 31:
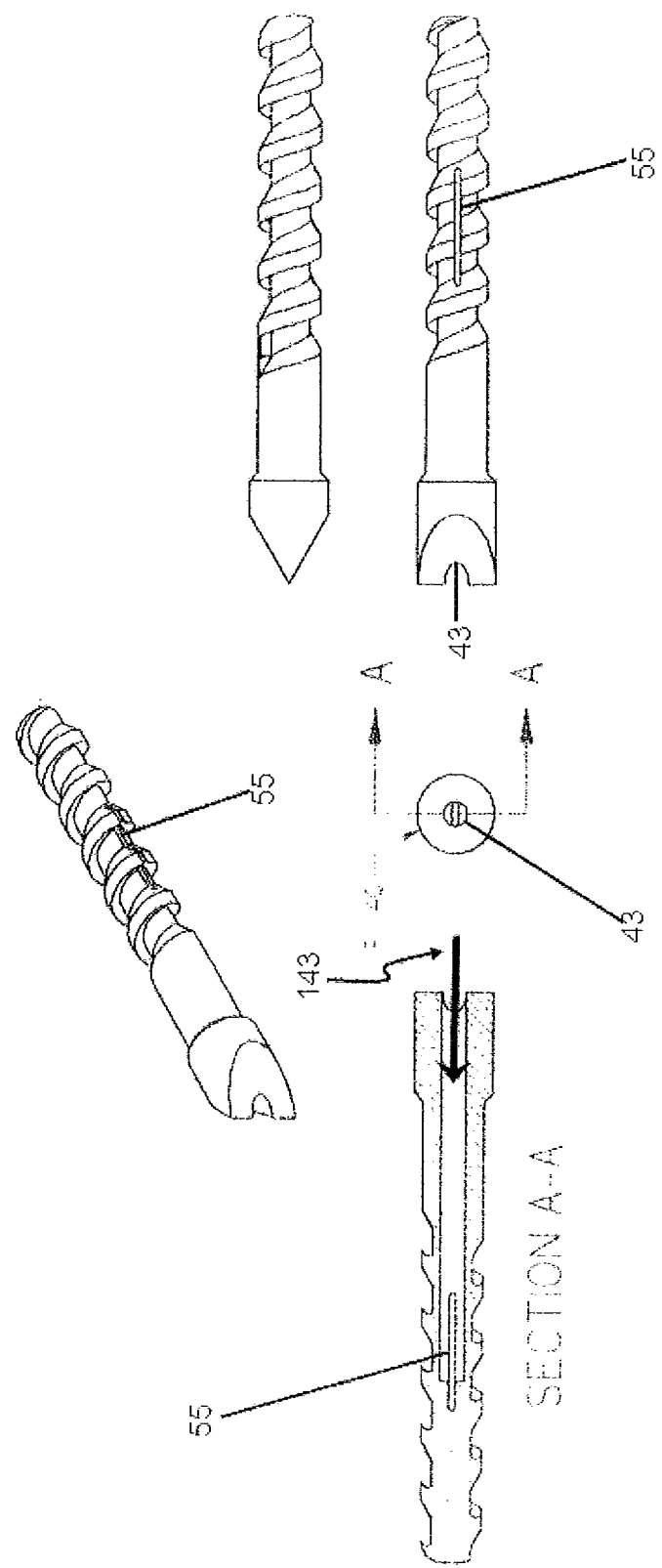
Figure 34:
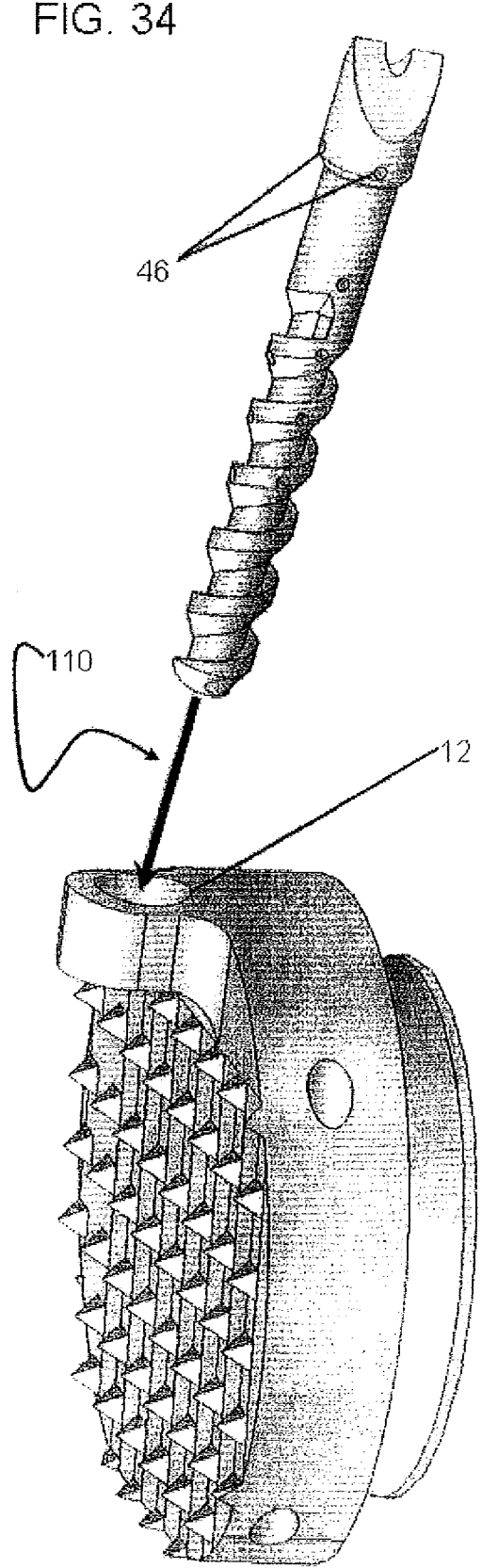
Figure 36:
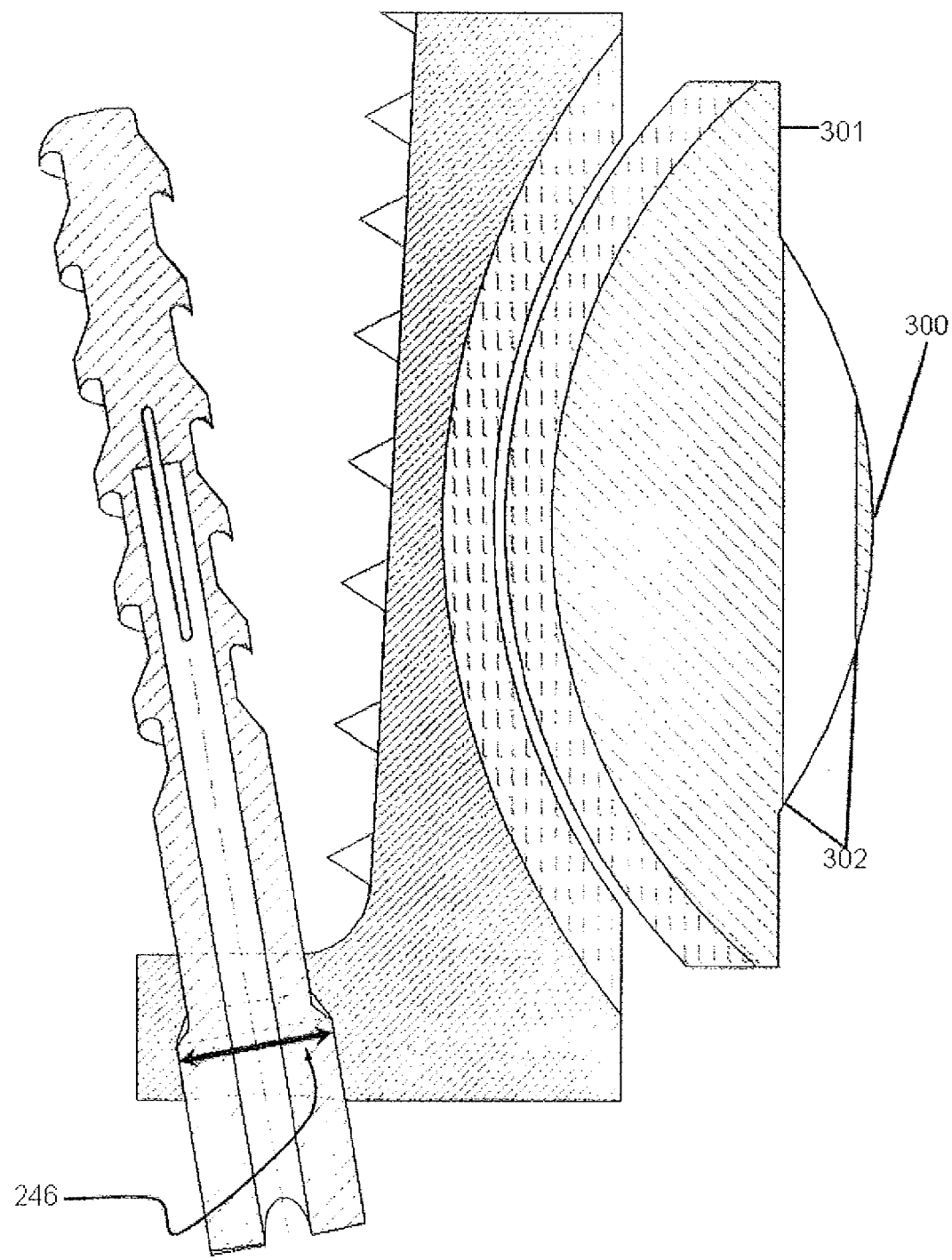

FIGS. 30, 32, and 33 show another embodiment of the bone screw 40 of the present invention in which additional features are disclosed. Flowable interdigitation apertures(s) 45, previous described, are modified in the form of implant interdigitation features 46 which extends from the flowable injection aperture 43 to the surface 146 (which is operably surrounded by 12 to enable the flowable material to emerge from feature(s) 46 and interdigitate with the allograft tissue of the acetabular plug, and thereby facilitate the fixation by and between the bone screw and the interior surfaces of 12, when the two are fixed with respect to each other as generally shown in FIG. 34 and FIG. 36. It should be noted that the flowable material would emerge through 46 to contact the interior surface of 12 by flowing in the general direction generally indicated as 246 in FIG. 36 to effectively interdigitate with the porous or semi porous interior surface of 12). The purpose of this additional level of fixation by way of flowable material interdigitation between implant, bone screw, and patient bone is to effectively preload the resulting composite structure and to effectively strengthen the screw, implant, and bone to enable the composite structure to better survive the loads experienced by it and thereby facilitate incorporation and longevity.

Figure 35:
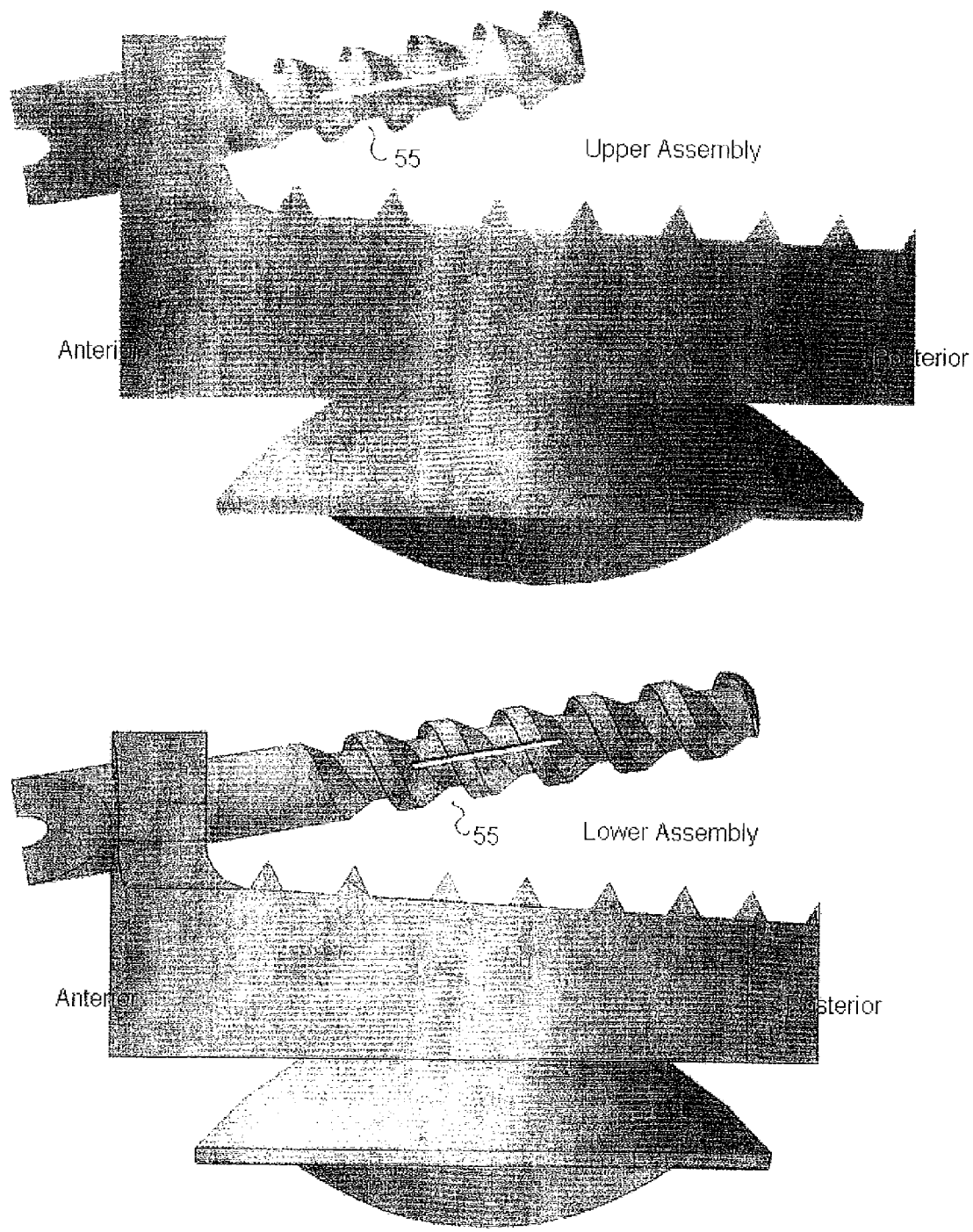

In severely osteoporotic patients the bone in the center of the vertebral body is often extraordinarily soft and thereby ill suited to support the implants of the present invention without additional structural reinforcement. Flowable interdigitation apertures 45 or 55 enable the injected flowable material to extrude and flow into this soft, porous bone to not only increase the effective surface area about which a preload may be maintained (as previously discussed), but also to significantly improve the strength of the vertebral body itself. Two pictures of assemblies of the present invention are shown in FIG. 35 to make it clear that the bone screw may come in various lengths and/or diameters, and that the flowable interdigitation apertures may be located at different locations along the bone screw 40 to enable interdigitation and augmented fixation in different locations along the screw and therefore within the vertebral body. The configuration shown in the upper assembly would facilitate fixation between the implants and the interior and more anterior surfaces of the vertebral body while the lower assembly would facilitate fixation between the implants and the interior and more central surfaces of the vertebral body by way of changes in the location of 55 or 45. Although not shown, features 45 or 55 could be located at the leading end of the screw to facilitate interdigitation with the vertebral body at the posterior most face of the interior of the vertebral body.

Figure 38:
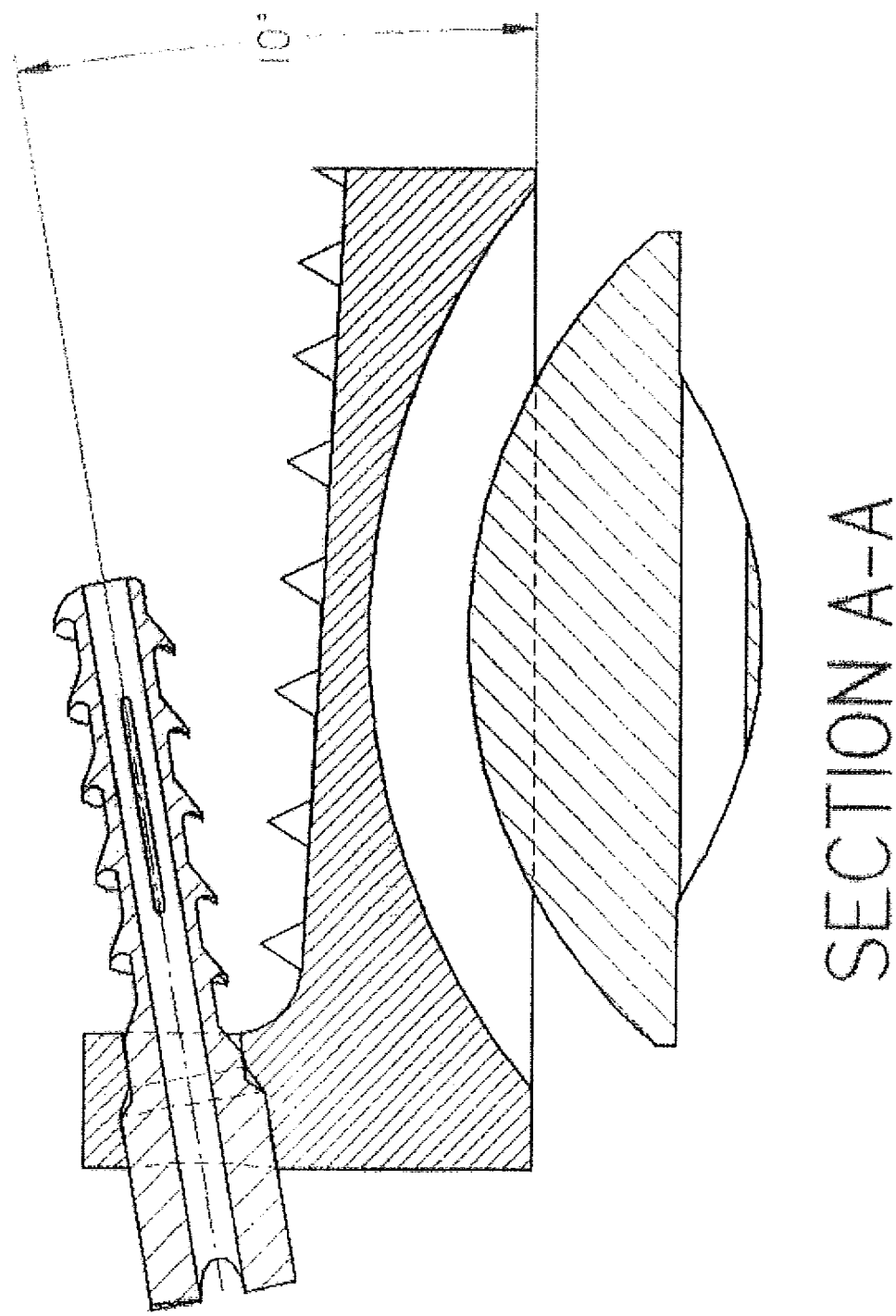
Figure 39:
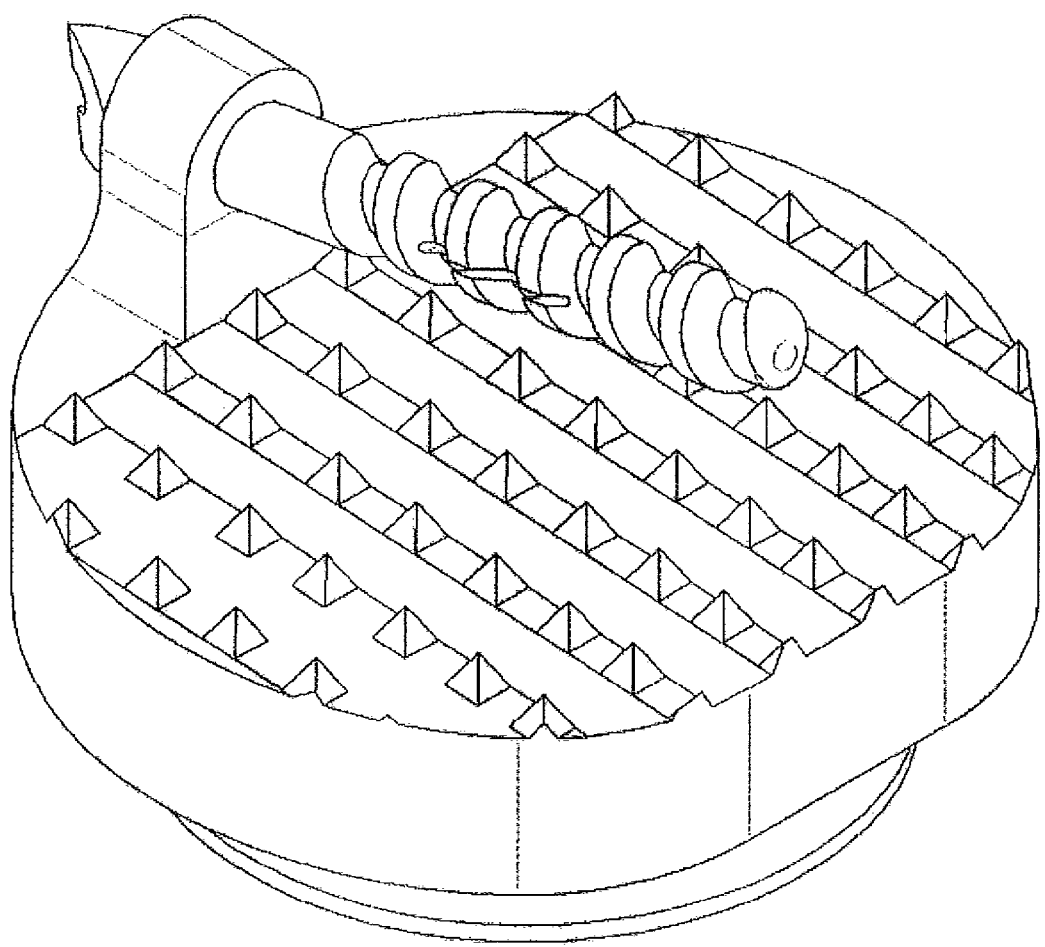
Figure 40:
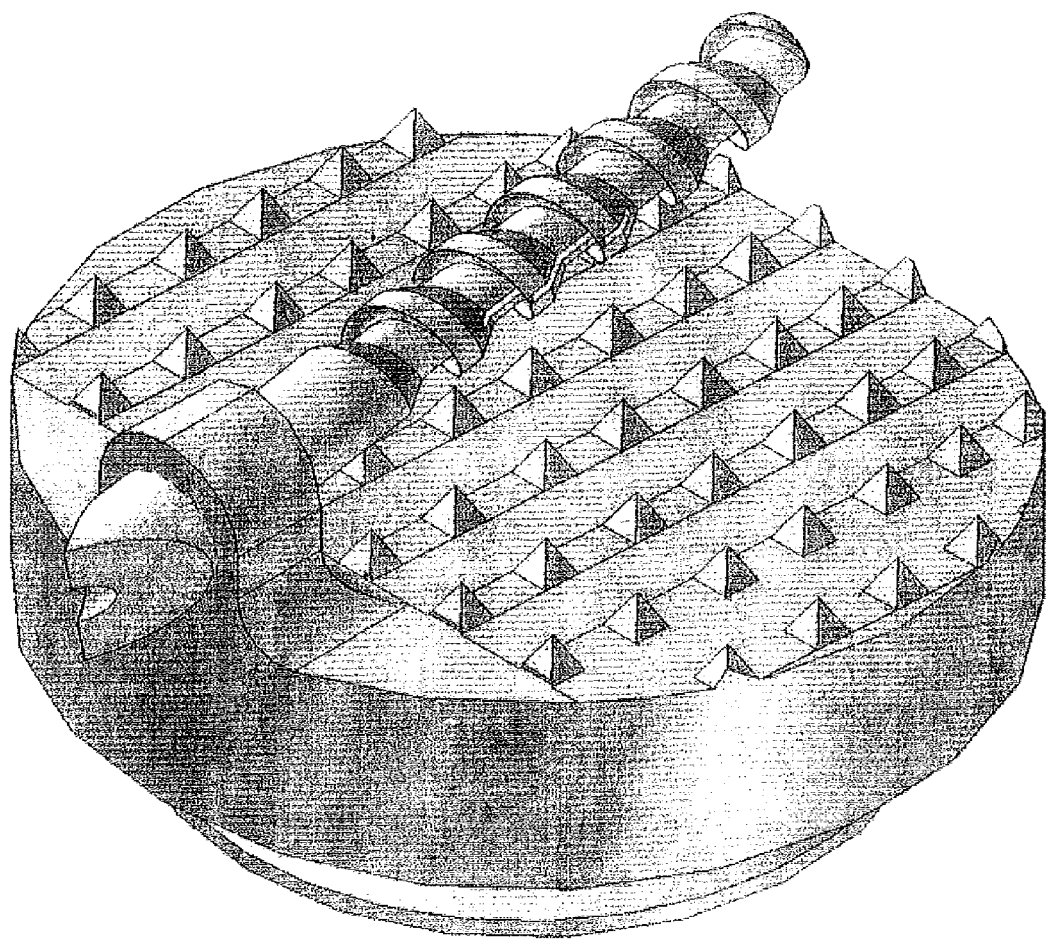
Figure 41:
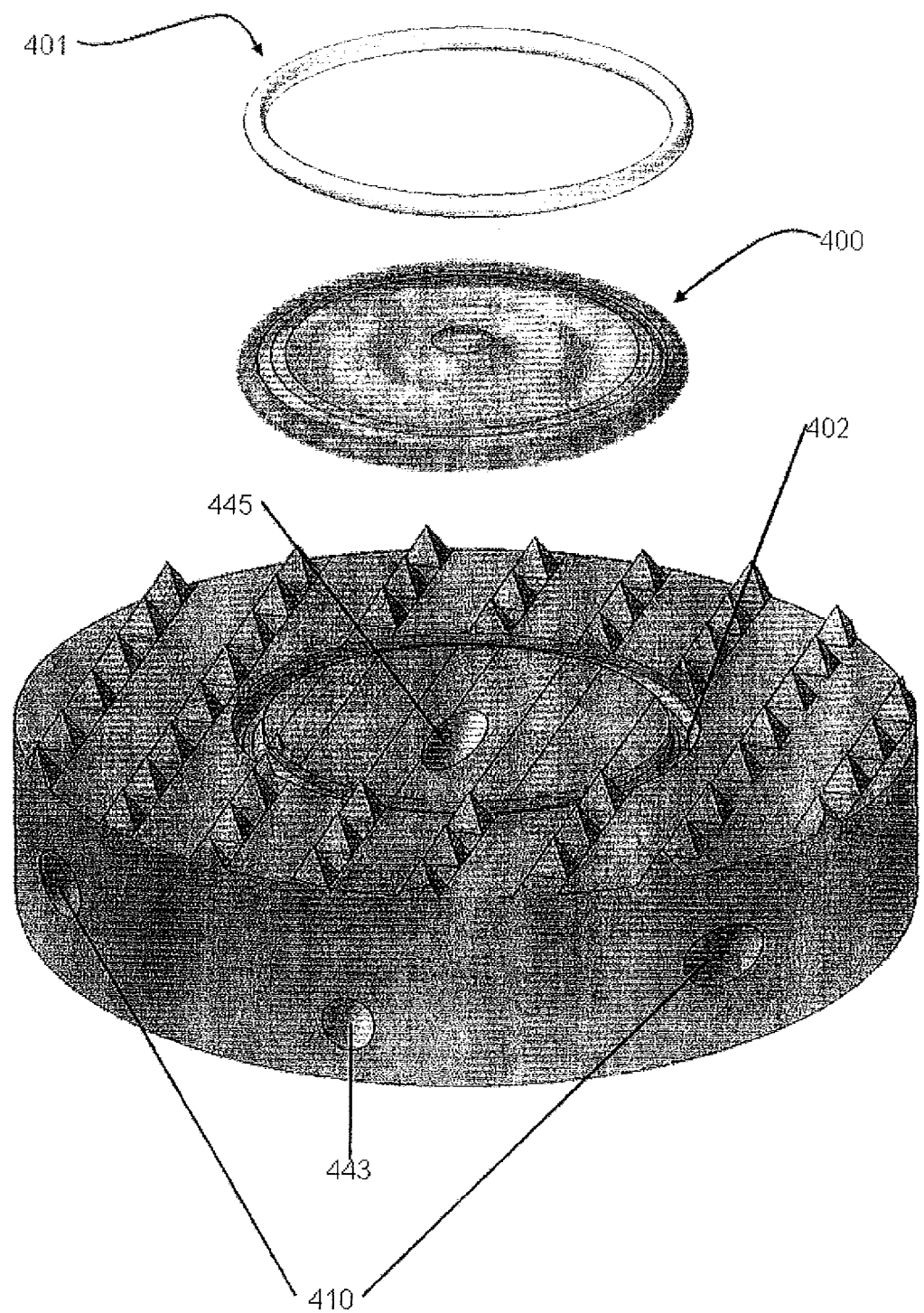

As shown in FIG. 38, the flowable injection aperture 43 may extend completely through bone screw 40 to facilitate interdigitation both peripherally through 45 or 55 and longitudinally through the leading end of the screw 40. The bone screw 40 has additional features to facilitate fixation with living bone. As shown in FIG. 33, the flowable injection aperture 43 may extend substantially along nearly the entirety of the bone screw 40 length even though the flowable interdigitation apertures 45 or 55 are located more centrally. This embodiment of the bone screw of the present invention is especially useful when the bone screw is constructed of human cortical allograft bone, or cortical xenograft, as the injection of a flowable material such as PMMA or 'bone cement' will significantly increase the strength of the screw itself without interfering substantially with the postoperative incorporation of the screw within the vertebral body.

Another unique feature of the bone screw 40 is shown clearly in detail B of FIG. 33 where an undercut 70 is formed between the crest and root of the thread form to effectively 'cup' the bone which is in contact with the screw such that the bone in contact with the undercut is loaded substantially in compression in a direction generally parallel with the axis of the screw as viewed in at least one plane as opposed to the load state created by traditional thread forms which include significant shear and radially oriented compressive force components. A ball mill, modified ball mill, or modified single point bit may be used to create the undercut by manufacturing methodologies well understood in the machining art. It should also be noted that the flowable injection aperture may terminate in a flat bottom, curved bottom, or 118 degree tapered drill tip bottom as generally indicated in Detail B of FIG. 33.

Figure 37:
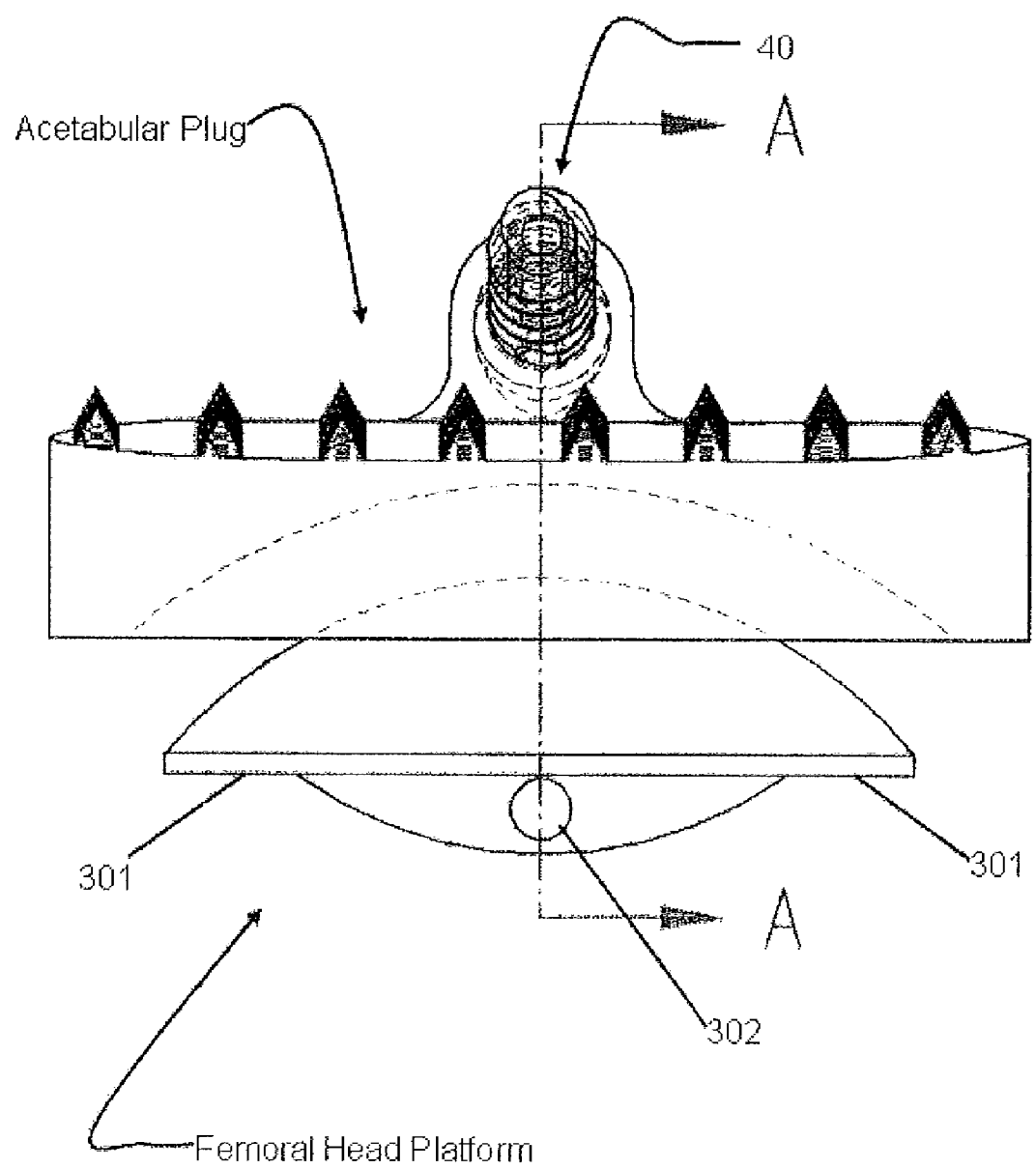

Yet another embodiment of the present invention is shown in detail in FIGS. 36 and 37. This shows a hemispherical protrusion formed in the implant-bone interface surrounded by a substantially flat area. The flat area of the implant-bone interface coincides with a substantially flat cut made on the endplate surface while the hemispherical protrusion coincides with a substantially hemispherical cut in the central portion of the endplate. Preparation of the endplate surfaces may be performed in a manner similar to the instrumentation available for the Bryan™ Cervical Disc or any other means or methods known in the art. Additional fixation may optionally be provided by providing a form of XPin™ based fixation. XPin™ fixation is a method and apparatus first proposed to facilitate preload, or to maintain preload already attained between resected bone surfaces and implant fixation surfaces, and is described in U.S. patent application Ser. No. 11/075, 840, which is incorporated by reference in their entirety. In this embodiment of the present invention, an aperture is formed in the vertebral body which is generally coaxial with the XPin aperture 302, or, alternatively, intersecting XPin aperture 302, or, alternatively, extends into the vertebral body on the far side of 302. Upon completion of the cut(s) coinciding with 301 and 300, the implant is inserted between the resected endplates and contacted with the resected surfaces. The implant may then be preloaded by instrumented means into preloaded contact with the resected surfaces with the aperture formed in the vertebral body properly aligned with 302. In this preloaded state, bone cement, or other flowable material which hardens over time, may be injected into the aperture formed in the vertebral body, through 302, and into the vertebral body on the opposite side of 300 through 302. Upon hardening of the flowable material, the instrumentation which induced preload may be removed and the preload maintained by the XP in composite structure thus created. This is another application of the present inventions wherein careful control of the total volume of flowable material into the vertebral body must be exercised to avoid either deleterious extravasation or retardation of incorporation. Simply offering, for instance, a pre-packaged, pre-measured amount of flowable material in an "injection gun" is the simplest way to achieve this objective.

Figure 43:
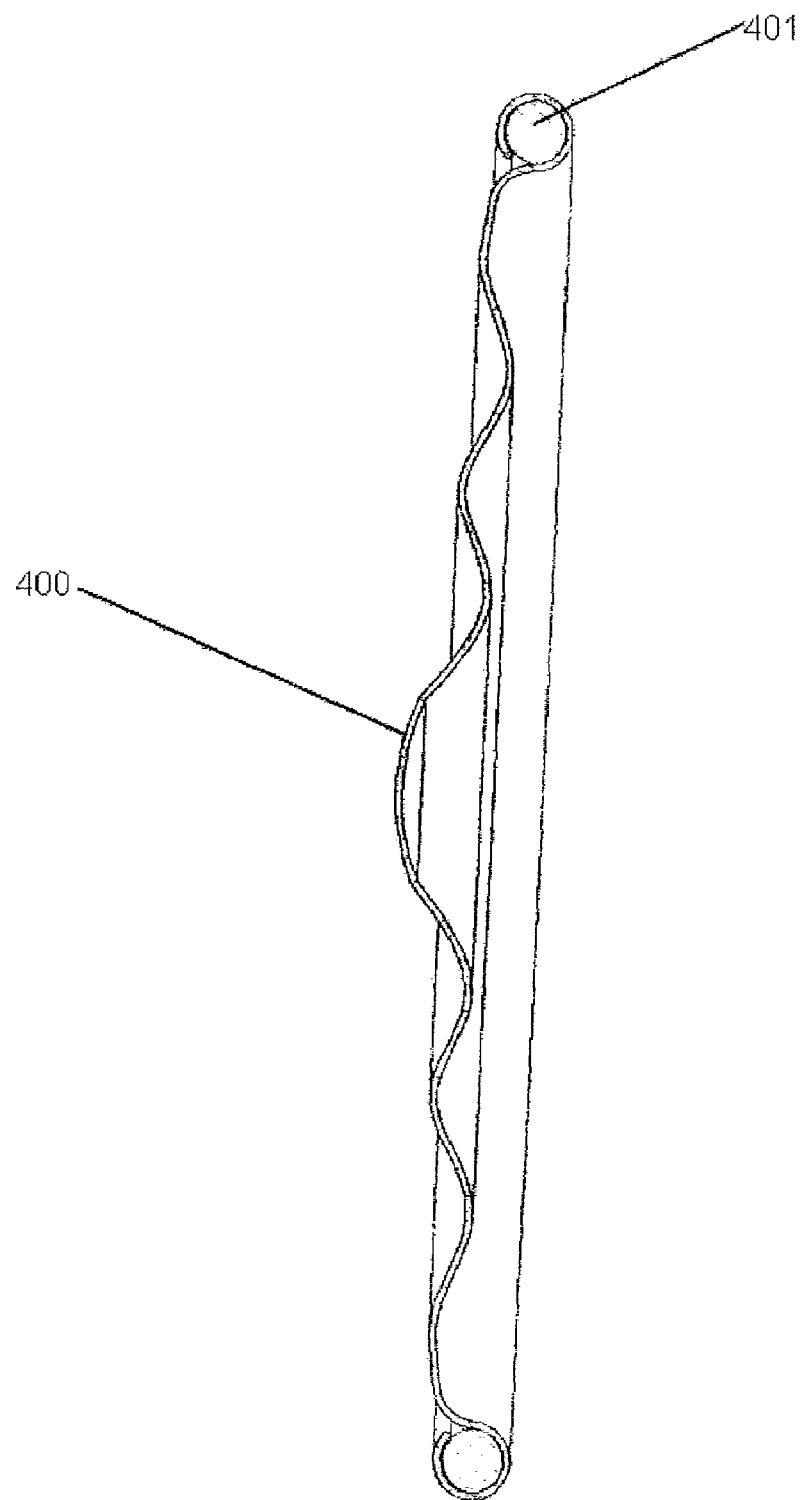
Figure 44:
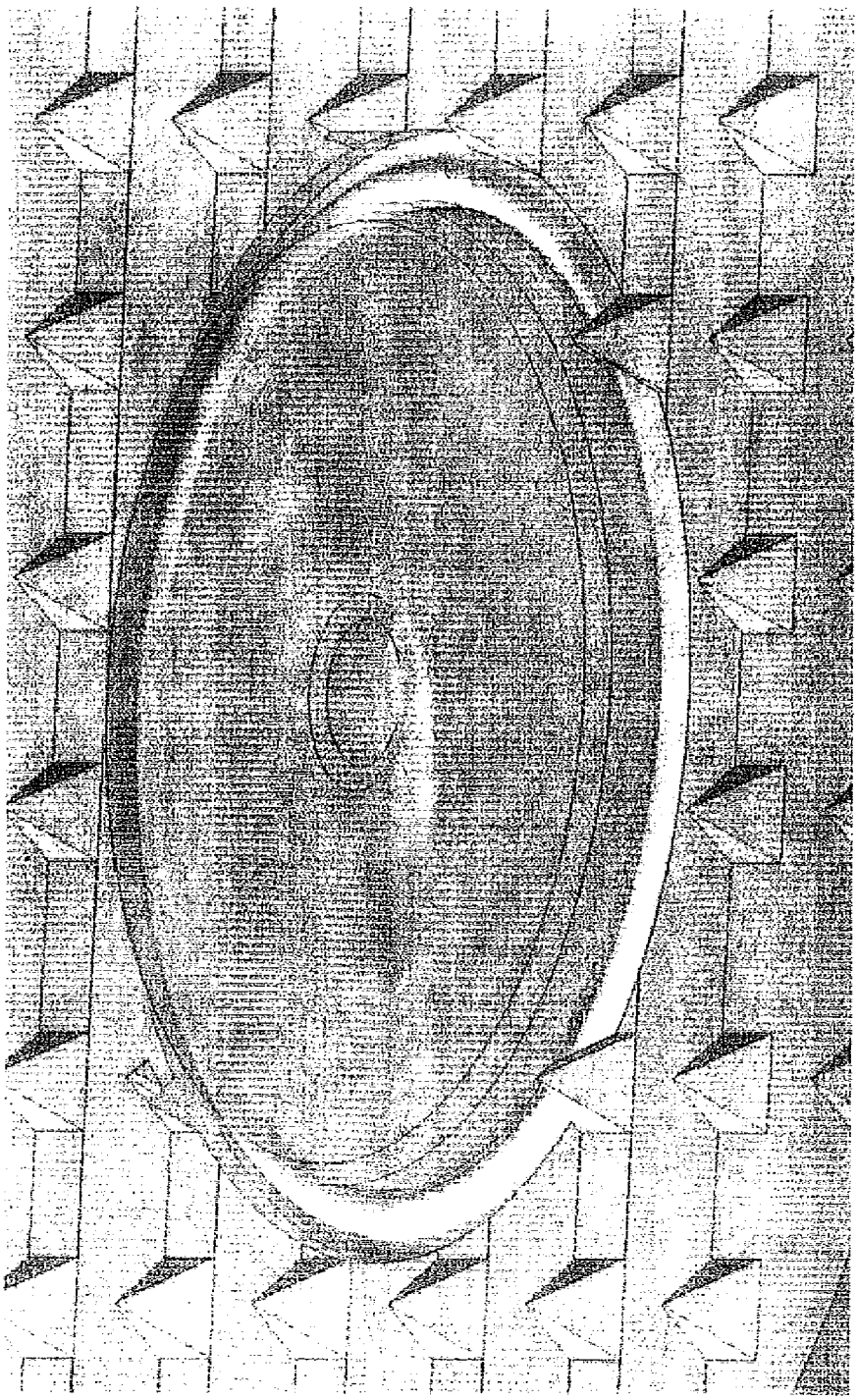
Figure 46:
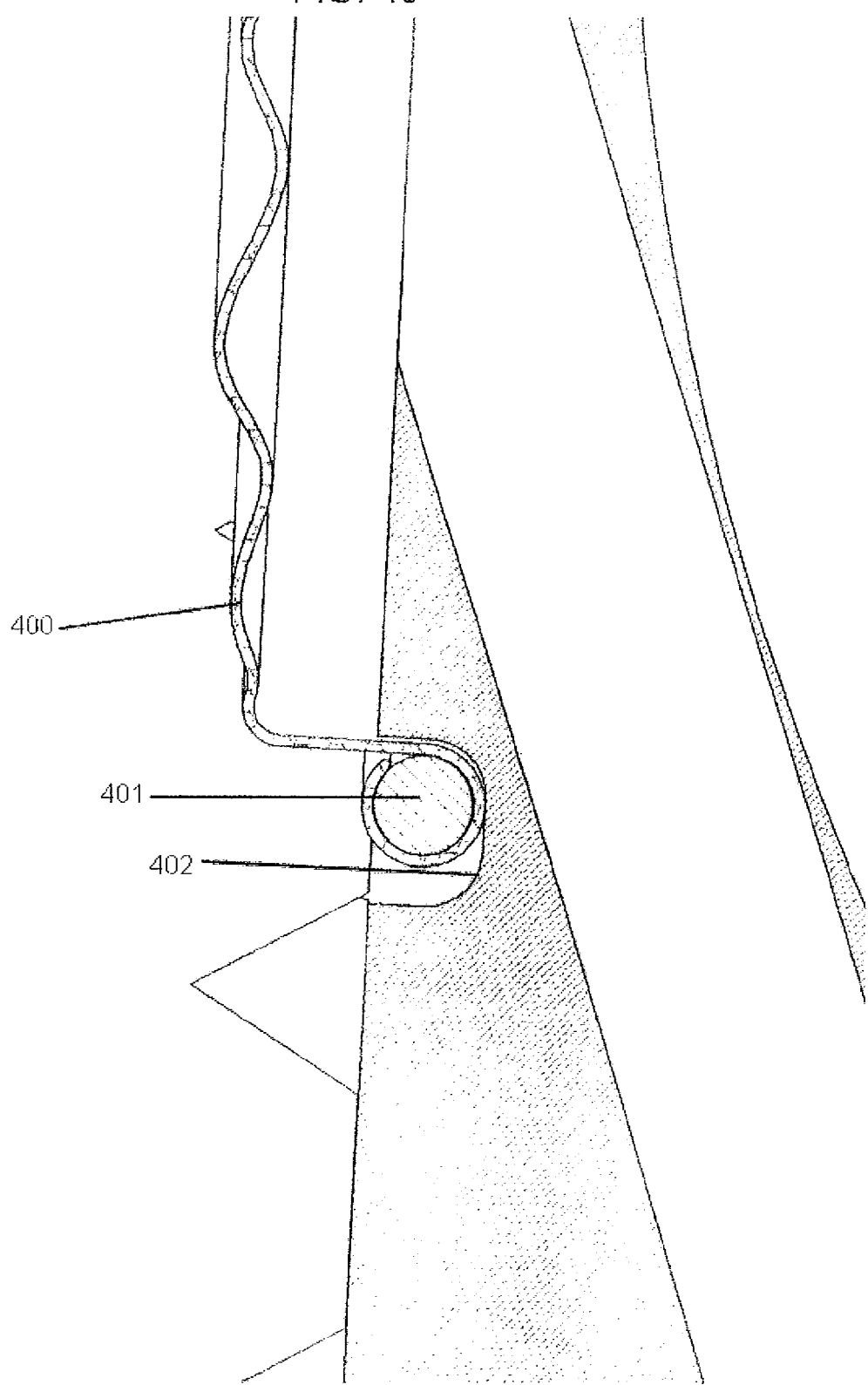

FIGS. 41-48 show yet another embodiment of the present invention. The components of this embodiment include ring 401, mesh 400, ring retaining feature 402, flowable injection aperture 443, and flowable interdigitation aperture 445. Instrument preload feature(s) 410 are also shown. Ring 401, and mesh 400 may be preassembled as indicated in FIGS. 42-43, and then attached to ring retaining feature 402 of the implant. One method of assembly would be to apply a coating of adhesive into the surfaces of ring retaining feature 402 into which the ring 401, and mesh 400 would be inserted to affect adhesive and/or mechanical bonding. Furthermore, an undercut in 402 may be provided for mating with a split ring embodiment of ring 402 as is well known in the mechanical arts. The resulting assembly of 400, 401 and Acetabular plug is shown in FIGS. 44-48. Intraoperatively, the implant would be inserted between the prepared or resected endplate surfaces, including a resected surface to intimately mate with the "inflated shape" of the mesh 400 (see FIG. 47 for a comparison of inflated versus uninflated shapes for mesh 400), optionally preloaded into contact with the endplate, a flowable injection nozzle engaged to 443, and flowable material injected from the nozzle, through 443, and "up under" mesh 400 (as shown by the juxtaposition of the mesh 400 over 445 in FIG. 44) by way of flowable interdigitation aperture 445.

Figure 48:
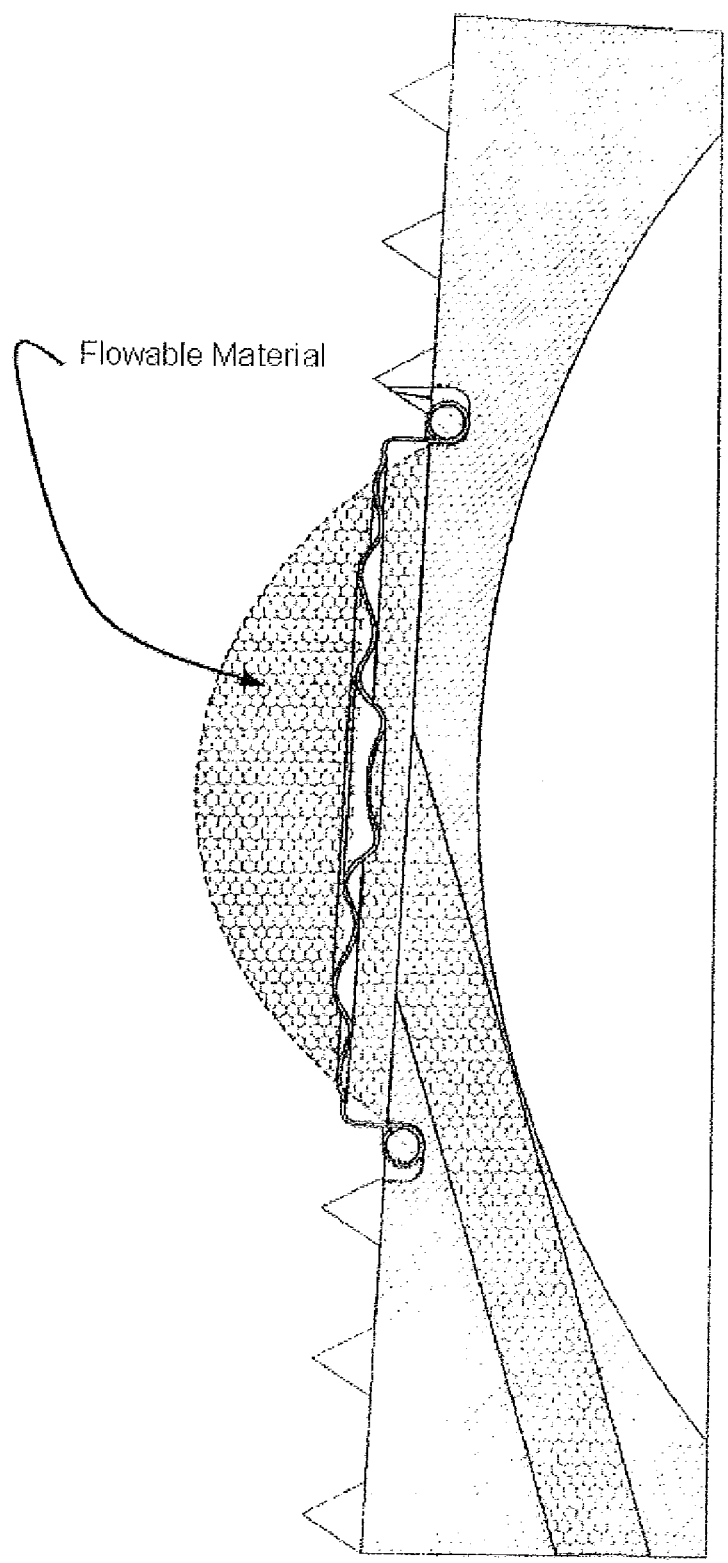

Additional injection of flowable material will 'inflate' the mesh to a nominal shape determined by both the mesh 400 and the coinciding resected surface to the mesh as generally shown in FIG. 48. It should be noted that the mesh may be highly porous to allow for extravasion of the flowable material through the pores of the mesh (such as when used with bone cement), or the pores could be configured for use with morselized cancellous or cortical allograft or autograft wherein the graft material would essentially "poke out" of the mesh a bit to allow contact between the graft and the surrounding living bone to effect intimate contact between the graft and the mesh, as well as intimate contact between the mesh and the living bone. The teachings of this mesh methodology are similar to the work by Kuslich, et al. as described, for example, in U.S. Pat. No. 5,549,679. The teachings of Kuslich et al are improved upon by providing the means and methods to provide for improved implant fixation by way of mesh inflation in dynamic disc replacement. This embodiment of the present invention also serves to increase the effective bone-implant contact surface area of an implant surface by at least 30% compared to comparable non-mesh designs. This embodiment of the present invention also provides for significant resistance to expulsion of the intervertebral implants of the present invention out from between the endplates of the vertebral bodies by way of interference between the inflated mesh and the coinciding resected surface(s)

Figure 49:
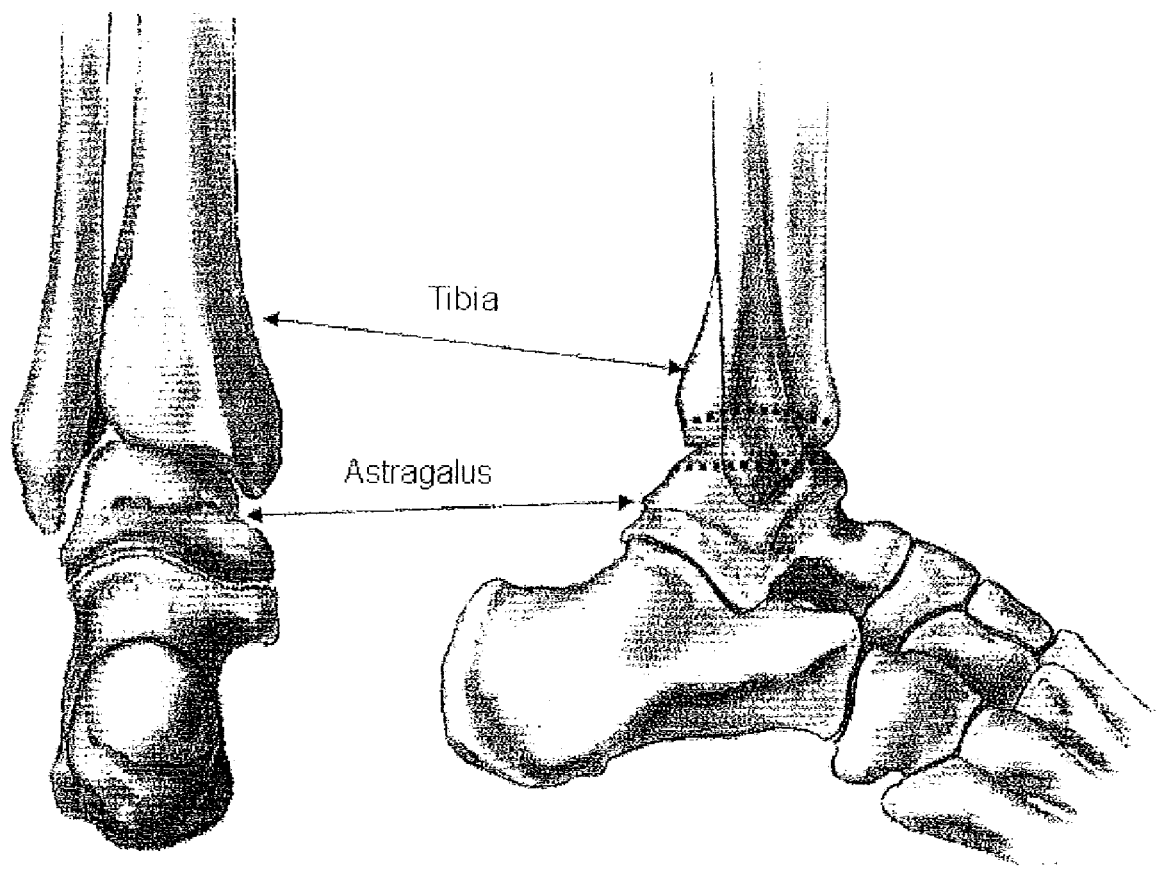
Figure 50:
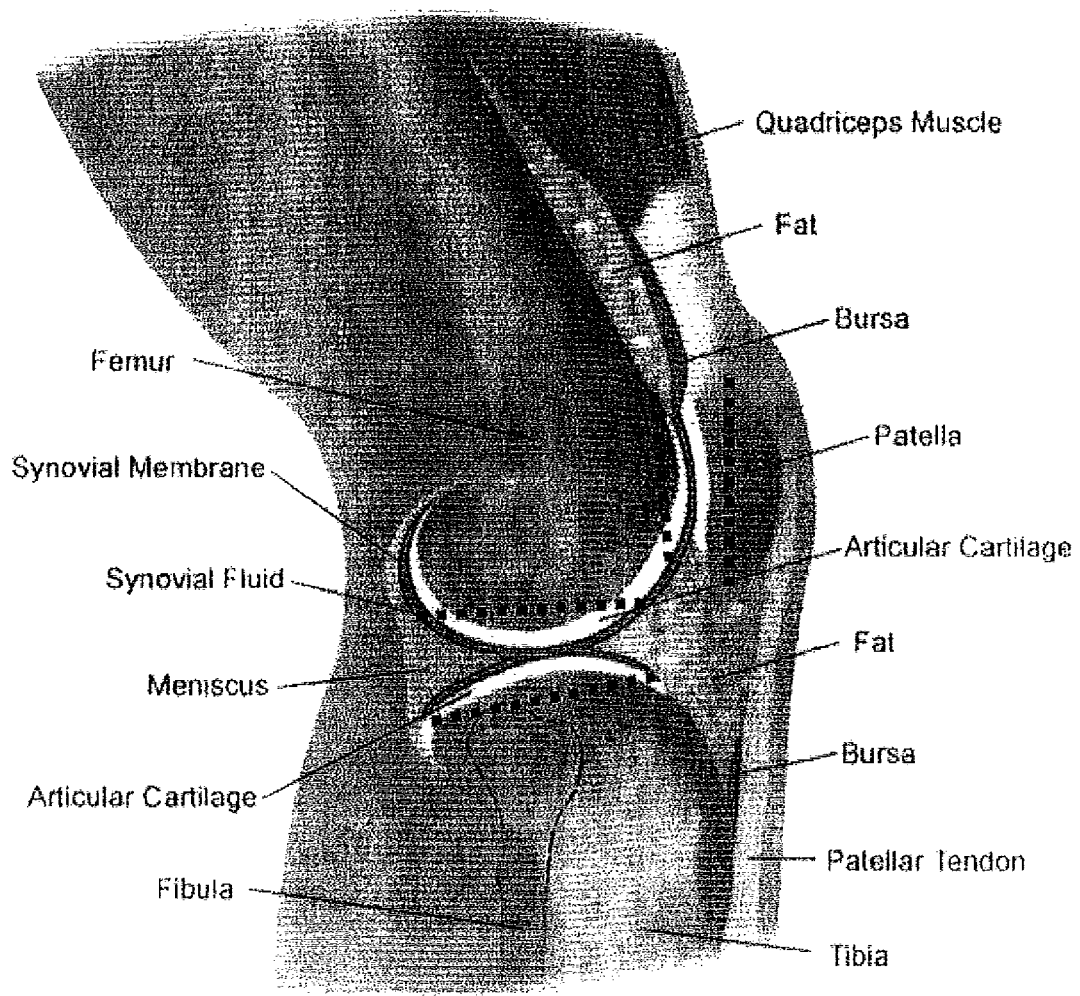

Alternate Articular Allograft Sources—The embodiments of the dynamic disc replacement implant of the present invention are shown as having been derived from a human hip joint. It is to be understood that this is for illustrative purposes only and that the implant may be derived from any joint including the knee (as shown in FIG. 50 this could be derived of tibiofemoral articular surfaces or patellofemoral surfaces as shown generally by dashed lines), or the ankle (as shown in FIG. 49 by the dashed lines) wherein the cuts made to remove the articular grafts are generally indicated by dashed lines. Other joints suitable as sources for HipAllo implants include the elbow, wrist, shoulder, and the spine itself.

Another family of embodiments of the present invention include removing intact intervertebral discs still bearing vertebral body bone on upper and lower texture bearing surfaces similar to 10 in FIG. 24, and optionally including the Alternate Keying Features and/or fixation features hereinbefore discussed.

Simultaneous Dynamic Disc Replacement and Facet Arthroplasty—Facet Arthroplasty is a technical field currently in its infancy and being pioneered by Archus Orthopaedics, Inc. of Seattle, Wash., for example. Numerous reports in the literature indicate that the majority of patients who have degenerative disc conditions calling for dynamic disc replacement cannot receive dynamic disc implants alone due to degeneration of the facets. Simply put, if you are going to use a dynamic disc as a treatment alternative to fusion, you will almost always need to replace the facet articular surfaces as well. It is within the scope of the present invention to provide allograft based facet arthroplasty implants derived from spinal facet tissue or other cartilage bearing articular joint tissue as per the teachings of the embodiments of the present invention. It is also within the scope of the present invention to mechanically fix the facet arthroplasty devices to both the vertebral body and the dynamic disc replacement implants of the present invention to stabilize and fix them with respect to each other and the spinal body.

As previously discussed, dynamic or static simultaneous balancing of the posterior and anterior column articulations of the spine may be implemented to ensure the accurate placement of the facet arthroplasty implants and dynamic disc replacement implants with respect to each other given the kinematics of the patients spine. Critical elements of both dynamic and static balancing techniques include distraction of the facing endplate surfaces to an extent corresponding to the size of the dynamic disc replacement device to be implanted therebetween, distraction of the facing degenerated facet surfaces to an extent corresponding to the size of the facet arthroplasty device to be implanted therebetween, and observing the appropriateness of the resulting anterior column and posterior column balance. Dynamic balancing techniques would include the additional step of moving one vertebral body through its range of motion with respect to the adjacent vertebral body to enable verification of the balance attained between the anterior column and posterior column throughout the range of motion of one vertebral body with respect to the other.

Additional Techniques—Several techniques in addition to the ones noted above are within the scope of the present invention. These include the following:

A method for implanting an allograft derived dynamic disc replacement implant comprising the steps of: removing facing cartilage bearing bone surfaces from a mammalian joint; shaping surfaces of the bone surfaces in a shape to mate with resected vertebral body endplate surfaces; resecting the endplate surfaces of adjacent vertebral bodies, the step of resecting the endplate surfaces resulting in resected endplate surfaces to mate with the bone surfaces; and inserting the bone surfaces between the resected endplate surfaces. This method can further include secondary fixation features implemented to augment fixation of the bone surfaces to the resected endplate surfaces. The method can also include a flowable material which is introduced between the bone surfaces and the resected endplate surfaces, the flowable material comprising one of an osteobiologic agent, bone cement, antibiotic, morselized bone, biocompatible ceramic beads or particles, compounds including hydroxyapatite, tricalcium phosphate, or other osteoconductive or osteoinductive compositions, including, but not limited to bone morphagenic proteins (BMPs) or other recombinant technology derived substance, or which flowable material is a combination of any or all of the aforementioned.

In another embodiment of the present invention, a synovial tissue construct is used in conjunction with the embodiments of the present invention. Synovial membranes generate synovial fluid which is present in normal, healthy long bone joints and acts as a lubricant therefore. Although it is likely that a pseudoarthrosis may form about the implants of the present invention by way of normal healing processes, it is within the scope of the present invention to encapsulate the adjacent articular surfaces of the present invention with a synovial bearing tissue construct to generate synovial fluid and therefore provide lubrication for the devices. Such synovial tissue may be derived from donor tissue, or patient tissue, and may be cultured and/or "grown" as known in the art of recombinant DNA based technologies.

The following patents and patent applications describing various surgical navigation system and alignment and guide systems that may be utilized in whole or in part with this embodiment of the present invention are hereby incorporated by reference:

U.S. 2004/0122436, U.S. 2003/0069591, U.S. 2004/0039396, U.S. 2004/0153083, U.S. Pat. No. 5,810,827, U.S. Pat. No. 6,595,997, U.S. 2003/0069585, U.S. 2003/0028196, JP74214-2002, U.S. 2003/0208122, U.S. Pat. No. 6,725,080, U.S. 2004/0122305, U.S. Pat. No. 6,685,711, U.S. 2004/0153085, U.S. 2004/0152970, U.S. Pat. No. 6,694,168, WO04100758, WO04070580, WO04069036, U.S. Pat. No. 5,799,055, U.S. Pat. No. 6,236,875, U.S. Pat. No. 6,285,902, U.S. Pat. No. 6,340,363, U.S. Pat. No. 6,348,058, U.S. Pat. No. 6,430,434, U.S. Pat. No. 6,470,207, U.S. Pat. No. 6,477,400, U.S. Pat. No. 6,491,699, U.S. Pat. No. 6,697,664, U.S. Pat. No. 6,701,174, U.S. Pat. No. 6,711,432, U.S. Pat. No. 6,725,080, U.S. Pat. No. 6,796,988, and U.S. Pat. No. 6,827,723.

The following patents and patent applications, also by the inventor of the present invention, describe various surgical alignment guides, drill guides, and/or cutting guides and methods therefore, and implant fixation apparatus and/or methods that may be utilized in whole or in part with the embodiment of the present invention are hereby incorporated by reference:

U.S. Pat. Nos. 5,514,139, 5,597,379, 5,643,272, 5,810,827, and U.S. Publ. No. US2002-0029038 A1, US2006-0015109, US2006-0015115, US2006-0015116, US2006-0015117.

Benefit will also be found in an embodiment of the present invention where a bracket is positioned and fixed to the side of the vertebra wherein the bracket is configured to receive cutting guide surfaces as illustrated in U.S. Pat. No. 6,695,848 (which is herein incorporated by reference) FIGS. 13A through 15C by Haines.

It should be noted that the individual embodiments of the present invention are shown to be illustrative, not limiting to the scope of the present invention. Specifically, any individual features described herein may be combined with any other features herein or known in the art while being within the scope of the present invention. Furthermore, the majority of the embodiments shown herein are described to be implanted by way of an anterior approach to the spine, but one of ordinary skill in the art will readily recognize those modifications enabling the embodiments of the present invention to be implanted from any orientation with respect to the spine including, but not limited to, anterolateral, posterior, posterolateral, superiorly and/or inferiorly; All such methods and/or modified embodiments of the present invention are within the scope of the present invention. It is an object of one embodiment of this invention to provide methods and apparatus for dynamic disc replacement in conjunction with facet arthroplasty. Methods and apparatus for dynamic disc replacement and facet arthroplasty wherein the dynamic disc replacement is operably interconnected and/or mechanically fixed with respect to facet arthroplasty implants.

It is an objective of one embodiment of the present invention to provide methods and apparatus for disc replacement without articular materials where debris generation may lead to osteolysis or other forms of foreign body reaction or inflammatory response.

It is an additional object of one embodiment of the present invention to provide methods and apparatus for dynamic disc replacement which implement preloaded bone implant interfaces for a prolonged postoperative preload of said interfaces by increasing the surface area against which the preload is attained by the injection of a fluid or slurry which subsequently polymerizes or hardens between implant and bone interfaces.

It is also an object of one embodiment of the present invention to provide methods and apparatus for dynamic disc replacement which enable 6 degrees of freedom of motion between adjacent vertebrae including 3 degrees of rotational freedom and 3 degrees of translational freedom, all of which degrees of freedom occurring about or along 3 mutually perpendicular axes.

It is another object of one embodiment of the present invention to provide methods and apparatus for dynamic disc replacement wherein translational degrees of freedom about 3 mutually perpendicular axes are constrained by a shock absorbing viscoelastic material intimately adhered to material whose modulus of elasticity is within +/−30% of the modulus of elasticity of living bone tissue to which the implant is attached.

It is a further object of one embodiment of the present invention to provide methods and apparatus for dynamic disc replacement where all inorganic materials of the implants are comprised of materials indigenous to mammalian bodies with the optional exceptions of bone cement, antibiotics, and/or osteobiologic agents.

It is an additional object of one embodiment of the present invention to provide methods and apparatus for dynamic disc replacement wherein the clinical performance of the disc implant is relatively insensitive to variations in surgical technique.

It is another object of one embodiment of the present invention to provide methods and apparatus for dynamic disc replacement which, when implanted by way of an anterior approach, may be revised by a posterior approach fusion or revision dynamic disc.

It is yet an additional object of one embodiment of the present invention to provide methods and apparatus for dynamic disc replacement wherein the disc implant and/or the endplate contacting components of the disc implant is/are inserted between the adjacent endplates simultaneously.

These objects and others are met by the methods and apparatus for dynamic disc replacement and/or facet arthroplasty of the present invention. It is an often repeated rule of thumb for orthopedic surgeons that a "Well placed, but poorly designed implant will perform well clinically, while a poorly placed, well designed implant will perform poorly clinically." A corollary to this statement is that the best possible implant design is one whose performance is most independent of variations in surgical technique. The present invention provides an apparatus inherently less sensitive to variations in technique by use of constructs derived from human joints. In addition, many of the embodiments shown have unique applicability to minimally invasive surgical (MIS) procedures and/or for use in conjunction with Surgical Navigation, Image Guided Surgery, or Computer Aided Surgery systems.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. An apparatus for dynamic spinal arthroplasty comprising:
   an implant for placement between two adjacent vertebral bodies which replaces tissue damaged by trauma or disease wherein said implant possesses at least two hyaline cartilage bearing surfaces, each bearing surface having an outer side adapted to be interfaced with a bone surface of one of the two adjacent vertebral bodies and having an inner side that includes a smooth hyaline cartilage layer over at least a portion of the inner side that interfaces with the smooth hyaline cartilage layer of another one of the at least two bearing surfaces to enable physiological loading and movement of the two adjacent vertebral bodies with respect to one another.

2. The implant of claim 1 wherein one of the at least two bearing surfaces is connected to an other of the at least two bearing surfaces by ligament material.

3. The implant of claim 1 wherein an outer surface of at least one of the at least two bearing surfaces includes augmented implantation structures defined thereon.

4. The implant of claim 3 wherein the augmented implantation structures include features machined on the outer surface.

5. A method for dynamic spinal arthroplasty for a patient comprising:
   providing an implant having at least two hyaline cartilage bearing surfaces, each bearing surface having an outer side adapted to be interfaced with a bone surface of one of two adjacent vertebral bodies and having an inner side that includes a smooth hyaline cartilage layer over at least a portion of the inner side that interfaces with the smooth hyaline cartilage layer of another one of the at least two bearing surfaces; and
   providing instructions for performing a dynamic spinal arthroplasty procedure, the instructions including:
      removing material from between two adjacent vertebral bodies of the patient; and
      inserting the implant between the two adjacent vertebral bodies in the patient such that the at least two hyaline cartilage surfaces enable physiological loading and movement of the two adjacent vertebral bodies with respect to one another.

* * * * *

UNITED STATES PATENT AND TRADEMARK OFFICE
CERTIFICATE OF CORRECTION

| | | |
|---|---|---|
| PATENT NO. | : 7,662,183 B2 | Page 1 of 1 |
| APPLICATION NO. | : 11/626634 | |
| DATED | : February 16, 2010 | |
| INVENTOR(S) | : Timothy Haines | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 168 days.

Signed and Sealed this

Thirtieth Day of November, 2010

David J. Kappos
*Director of the United States Patent and Trademark Office*